(12) United States Patent
Harberd et al.

(10) Patent No.: US 6,762,348 B1
(45) Date of Patent: Jul. 13, 2004

(54) GENETIC CONTROL OF PLANT GROWTH AND DEVELOPMENT

(75) Inventors: Nicholas P. Harberd, Norwich (GB); Donald E. Richards, Great Ellingham (GB); Jinrong Peng, Singapore (SG)

(73) Assignee: Pioneer Hi-Bred International, Inc., Johnston, IA (US)

( * ) Notice: Subject to any disclaimer, the term of this patent is extended or adjusted under 35 U.S.C. 154(b) by 0 days.

(21) Appl. No.: 09/485,529

(22) PCT Filed: Aug. 7, 1998

(86) PCT No.: PCT/GB98/02383

§ 371 (c)(1),
(2), (4) Date: Mar. 1, 2000

(87) PCT Pub. No.: WO99/09174

PCT Pub. Date: Feb. 25, 1999

(30) Foreign Application Priority Data

Aug. 13, 1997 (GB) .............................................. 9717192

(51) Int. Cl.[7] .......................... C12N 15/09; C12N 15/29; C12N 15/82; A01H 5/00; A01H 5/10
(52) U.S. Cl. ........................ 800/290; 800/278; 800/298; 800/295; 435/419; 435/468; 435/320.1; 435/430; 536/23.6; 536/24.1
(58) Field of Search ................................. 800/290, 278, 800/298, 295, 286, 320, 320.3; 435/320.1, 419, 468, 430, 430.1, 69.1, 320.2; 536/23.6, 24.1, 24.5

(56) References Cited

FOREIGN PATENT DOCUMENTS

| WO | WO 95/02060 | 1/1995 |
|----|-------------|--------|
| WO | WO 96/05317 | 2/1996 |
| WO | WO 97/29123 | 8/1997 |
| WO | WO 97/41152 | 11/1997 |
| WO | WO 97/43419 | 11/1997 |

OTHER PUBLICATIONS

Lazar et al, "Transforming Growth Factor x: Mutatyion of . . . Different Biological Activities", Mar. 1988, Molecular and Cellular Biology, pp. 1247–1252.*
Chory et al, "A role for Cytokinins in De–Etiolation in Arabidopsis", 1994, Plant Physiol vol. 104, pp. 339–347.*
Sandler et al, "Inhibition of gene expression in transformed plants by antisense RNA", 1988, Plant Molecular Biology vol. 11, pp. 301–310.*
Bird et al, "Manipulation of Plant Gene Expression by Antisense RNA", Dec., 1991, Biotechnology and Genetic Engineering Reviews, vol. 9, pp. 207–227.*
Smith et al, "Antisense RNA inhibition of polygalacturonase gene expression in transgenic tomatoes", Aug. 1998, Nature vol.334, pp. 724–726.*
Napoli et al., Introduction of a Chimeric Chalcone Synthase Gene into Petunia Results in . . . Homologous Genes in trans, Apr. 1990, The Plant Cell, vol. 2, pp. 279–289.*
Broun et al, "Catalytic Plasticity of Fatty Acid Modification Enzymes Underlying Chemical Diversity of Plant Lipids", Nov. 1998, Science vol. 282, pp. 1315–1317.*
Truong et al, "Sequence and characterization of two *Arabidopsis thaliana* cDNAs isolated by functional complementation of a yeast gln3 gdh1 mutant", FEBS Letters 410:213–218 (1997).
Sasaki et al, "Rice cDNA, partial sequence (S0803_1A)", EMBL Accession No. D39460, Nov. 13, 1994, XP–002088385.
Sasaki et al, "Rice cDNA, partial sequence (C51976_1A)", EMBL Accession No. C27475, Aug. 6, 19974, XP–002088386.
Peng and Harberd, "Derivative Alleles of the Arabidopsis Gibberellin–Insensitive (gai) Mutation Confer a Wild–Type Phenotype", The Plant Cell 5:351–360 (1993).
Harberd and Freeling, "Genetics of Dominant Gibberellin–Insensitive Dwarfism in Maize", Genetics 121(4):827–838 (1989).
Hooley, "Gibberllins: perception, transduction and responses", Plant Molecular Biology 26:1529–1555 (1994).
Jacobsen et al, "SPINDLY, a tetratricopeptide repeat protein involved in gibberllin signal transduction in *Arabidopsis*", Proc. Natl. Acad. Sci. USA 93(17):9292–9296 (1996).
Di Laurenzio et al, "The SCARECROW Gene Regulates an Asymmetric Cell Division That Is Essential for Generating the Radial Organization of the Arabidopsis Root", Cell 86:423–433 (1996).
Wilson and Somerville, "Phenotypic Suppression of the Gibberllin–Insensitive Mutant (gai) of Arabidopsis", Plant Physiol. 108:495–502.

* cited by examiner

Primary Examiner—Elizabeth F. McElwain
Assistant Examiner—Medina A. Ibrahim
(74) Attorney, Agent, or Firm—Nixon & Vanderhye PC

(57) ABSTRACT

The wheat Rht gene and homologues from other species including rice and maize (the D8 gene), useful for modification of growth and/or development characteristics of plants. Transgenic plants and methods for their production.

31 Claims, 22 Drawing Sheets

Figure 1

```
Gal   . . .MKRD HHHHHQDRKKT MMMNEEDDGN GMDELLAVLG YKVRSSEMAD VAQKLEQLEV 54
0803  EAGGSSGGGS SADMGSCKDK VEAGAXGEEE XVDELLAALG YKVRSSDMAD VAQKLEQLEM 60

Gal   MSNVQEDDL SQLATETVHY NPAELYTWLD
0803  AEGMGGVTPP AQRMTGSCRT WPRTKFI. . .
```

Figure 2a

CCCCGACGGTCGCGGCCGCGGCCAACGCGACGCCCGCGCTGCCGGTCGTCGTGG
TCGACACGCAGGAGGCCGGGATTCGGCTGGTGCACGCGCTGCTGGCGTGCGCGG
AGGCCGTGCAGCAGGAGAACCTCTCCGCCGCGGAGGCGCTGGTGAAGCAGATAC
CCTTGCTGGCCGCGTCCCAGGGCGGCGCGATGCGCAAGGTCGCCGCCTACTTCGG
CGAGGCCCTCGCCCGCCGCGTCTTCCGCTTCCGCCCGCAGCCGGACAGCTCCCTC
CTCGACGCCGCCTTCGCCGACCTCCTCCACGCGCACTTCTACGAGTCCTGCCCCTA
CCTCAAGTTCGCGCACTTCACCGCCAACCAGGCCATCCTGGAGGCGTTCGCCGGC
TGCCGCCGCGTGCACGTCGTCGACTTCGGCATCAAGCAGGGGATGCAGTGGCCC
GCACTTCTCCAGGCCCTCGCCCTCCGTCCCGGCGGCCCTCCCTCGTTCCGCCTCAC
CGGCGTCGGCCCCCGCAGCCGGACGAGACCGACGCCCTGCAGCAGGTGGGCTG
GAAGCTCGCCCAGTTCGCGCACACCATCCGCGTCGACTTCCAGTACCGCGGCC
TCGTCGCCGCCACGCTCGCGGACCTGGAGCCGTTCATGCTGCAGCCGGAGGGCG
AGGAGGACCCGAACGAAGANCCCGANGTAATCGCCGTCAACTCAGTCTTCGAGA
TGCACCGGCTGCTCGCGCAGCCCGGCGCCCTGGAAAAGGTTCTTGGGCACCGTGC
GCCCCGTGCGGCCCAGAATTCNTCACCGTGGTGGAAACAGGAGGCAAATCACA
ACTCCGGCACATTCCTGGACCGCTTCACCGAGTCTCTGCACTACTACTCCACCAT
GTTCGATTCCCTCGAGGGCGGCAGCTCCGGCGGCGGCCCATCCGAAGTCTCATCG
GGGGCTGCTGCTGCTCCTGCCGCCGCCGGCACGGACCAGGTCATNTCCGAGGTGT
ACCTCGGCCGGCAGATCTGCAACGTGGTGGCCTGCGAGGGGGCGGAACGCACAG
ANCGCCACGAGACGCTGGGCCAGTGGCGGAACCGGCTGGGCAACGCCGGGTTCG
AGACCGTCCACCTGGGCTCCAATGCCTACAAGCAGGCGANCACGCTGCTGGCGC
TCTTCGCCGGCGGCGAACGGCTACANGTGGAAGAAAAGGAAGGCTGCCTGACGC
TGGGGTTGCACACNCCCCCCTGATTGCCACCTCGGCATGGCGCCTGGCCGGGCCG
TGATCTCGCGAGTTTTGAACGCTGTAAGTACACATCGTGAGCATGGAGGACAACA
CAGCCCCGGCGGCCGCCCCGGCTCTCCGGCGAACGCACGCACGCACGCACTTGA
AGAAGAAGAAGCTAAATGTCATGTCAGTGAGCGCTGAATTGCAGCGACCGGCTA
CGATCGATCGGGCTACGGGTGGTTCCGTCCGTCTGGCGTGAAGAGGTGGATGGA
CGACGAACTCCGAGCCGACCACCACCGGCATGTAGTAATGTAATCCCTTCTTCGT
TCCCAGTTCTCCACCGCCTCCATGATCACCCGTAAAACTCCTAAGCCCTATTATTA
CTACTATTATGTTTAAATGTCTATTATTGCTATGTGTAATTCCTCCAACCGCTCAT
ATCAAAATAAGCACGGGCCGGAAAAAAAAAAAAAAAAAAAAAAAAAAAAAAAA
AAAAAAAAAAAAAAAAAAAAAAAAAAAAAAAAAAAAAAAAAAAAAAAAAAAAA
AAAAAA

Figure 2b(1)

CGCGCAATGCTTAAGGTCNCCGCCTACTTCGGNGCAGGCCCTCGCCCGCCGCGTC
TTCCGCTTCCGCCCGCAGCCGGACAGCTCCCTCCTCGACGCCGCCTTCGCCGACCT
CCTCCACGCGCACTTCTACNAGTCCTGCCCCTACCTCAAGTTCGCGCACTTCACCG
CCAATTAGGCCATCCTGGAGGCGTTCGCCGGCTGCCGCCGCGTGCACGTCGTCGA
CTTCGGCATCAAGCAGGGGATGCAGTGGCCCGCACTTCTCCAGGCCCTCGCCCTC
CGTCCCGGCGGCCCTCCCTCGTTCCGCCTCACCGGCGTCGGCCCCCCGCAGCCGG

Figure 2b(2)

ACCTCCTTCGTCGTCTNTNNGGTGGGGGCGCCAGGAGCTTATGTGGTGGAGGNTG
GCCCCNCCGGTCGCGACCGCGNCCTACGNGACGCCCGCGCTGCCGGTCGTCGTGG
TCGACACGCAGGAGGCCGGGATTCGGNTGGTNCACGCGCTGCTGGNGTGCGNGG
AGNCCGTGCAGCAGGAGAACCTCTCCGCCGCGGAGGCGCTNGTGAAGNAGATAC
CCNTGCTGGCCGAGTCCCAGGGCGGCGAGATGNGCAAGGTNGCAGCTTACTTNG
NAGANGCCCTCGCCCGCNGAGTGATTCCACTTANCGCCTGCAGCCGGANAGCTCC
GTCCTCGAANCCGCNTTNGCCGACCTCCTCCACGNGCACNTNTACGAGTC

Figure 2b(3)

TANTAGTCTCTCGGTGGGGGCGCCAGGAGCTCTNTGGTGGAGGCNGCCCCGCCG
GTCGCGGCCGCGGCCAACGCGACGCCCGCGCTGCCGGTCGTCGTGGTCGACACG
CAGGAGGCCGGGATTCGGATGGTGCACGCGCTGNTGGCGTGCGCGGAGGCCGTG
AAACAGTTGAAGGNCCNCGCCTNNNNNNCNCACAANNTGAAAGCCCCGNG

Figure 2b(4)

GGCTNCCNCCNCGTGCACGTCGTCGACTTCGGCATCAAGCATGGGATGCANTGGC
NCGNACTTCTCCANGCCCTCGCCCTCCGTCCCGGCGGCCCTCCCTCGTTCCGCCTC
ACCGGCGTCGGCCCCCCGCAGCCGGACGAGACCGACGCCCTGCANCAGGTGGGC
TGGAAGCTCGCCCAGTTCGCGCACACCATCCGCGTCGACTTCCANTACCGTGGCC
TCGTCGCCGCCACGCTCGCGGACCTGGAGCCGTTCATGCTGCANCCGGAGGGCGA
GGAGGACCCGAACGACGGAGCCCGAGGTAATCGCCGTCAACTCAGTCTTCGAGA
TGCACCGGGCTGCTCNCGCANCCCGGCGACNCTGGAANAA

Figure 2b(5)

CAAGANGCTAATCACAACTCCGGCACATTCCTGGACCGCTTCACCGAGTCTCTGC
ANTACTACTCCACCATGTTCGATTCCCTCGAGGGCGGCAGCTCCGGCGGCGGCCC
ATCCGAAGTCTCATCGGGGGCTGCTGCTGCTCCTGCCGCCGCCGGCACGGACCAT
GTCATGTCCGAXGTGTACCTCGGCCGGCAGATCTGCAACGTGGTGGCCTGCGAGG
GGGCGGAGCGCACANTANCGCCACGCAGACNCTGGGCCAGTGGCGTGAACCGGC
TGGGCAACGCCNGGTTCANNNNCCGTCCACCTGGGCTCCAATGCCTACAATCAN
GCNNNCACGCTGCTGGCGCCTCTTCGCCC

Figure 2b(6)

TCGCCANTCGGCATGGNGCCTGGCCGGGCCGTGATCTCGCGAGTTTTGAACGCTG
TAAGTACACATCGTGAGCATGGAGGACAACACAGCCCCGGCGGCCGCCCCGGCT
CTCCGGCGAACGCACGCACGCACGCACTTGGAAGAAGAANAAGCTAAATGTCAT
GTCAGTGAGCGCTGAATTGCAACGACCGGCTACGATCGATCGGGCTACGGGTGG
TTCCGTCCGTCTGGCGTGAAGAGGTGGATGGACGACGAACTCCGANCCGACCAC
CACCGGCATGTAGTAATGTAATCCCTTCTTCGTTCCCAGTTCTCCACCGCCTCCAT
GGATCACCCGTAAAACTCCTAAGCCCTAATTATNNACTAACTAATTATGTTTTAA
AATGTTCTAATTAATTGGCTATGTTGTAATNCCTCCAAACCGGCTCATTTTCAAA
NATTAAGCCACGGGCCCGGAACTTTGGTTTAACAACCTCCCNATTGNAAAATTNA
AATNGAAATTTTTGGTTNC

Figure 2b(7)

GTTGGTGGNGGCGATTTGGGTACAAGGTGCGCGCCTCCGACATGGNGGANGTGG
GGCAGAAGCTGGAGCAGNTCGAGATGGCCATGGGGATGGGNGGCGTGGGCGCT
GGCGCCGCCCCTGACGACAGGTTNGCCACCCGCNGGCCGCGGACACNGTGCANT
ACAACCCCACNGACNTGTCGTCTTGGGTCGAGAGCATGCTGTCGGAGCTAAANG
AGCCGCNGCCGCCCCTCCCGCCCGCCCCGCAGCTCAACGCCTCCACCTCCTCCAC
CGTCACGGGCAGCGGCGGCTACTTCGATAACCCTCCCTG

Figure 2b(8)

TGATGGNGGGAGNTTANGGGTTANAAATGTGGGGGANTTCCGAANNGGTGAGG
ANATATNNTCAGAAGTTGGAGCAGATGAGAGATNGCTGATGGGGATAGGGTAGG
NGTGGGTGCCGGTGCNGCCCCNAGGANAGATTGGCCACCCACTTAGCAAGTGG
ANACCGTGGATTACNACCCCACAGACCTGTCGTGGTTGGGTTTGAGAGCGTGGTG
TGGGAGCTGAACGGGCNGCGGCGTGCCCTCCCGCCCGCCCCGCAGCTCAACGCC
TCCACCTCCTCCACCGTACACGGGCAGCGGCGGCTAGTTCGATCTCCCGCCCTCC
GTCGACTCCTCCAGCAGCATNTANGCGCTGCGGCCGATCCCCTNCCCAAGCNNGC
GNGGNCCGAGCCGTGTAN

Figure 2b(9)

TTTCANTTTCNTCCTTTTTTCTTCTTTTTCCAACCCCCGGCCCCCNGACCCTTGGAT
CCAAATCCCGAACCCGCCCCCAGAACCNGGAACCGAGGCCAAGCAAAAGNTTTG
CGCCAATTATTGGCCAGAGATAGATAGAGAGGCGAGGTAGCTCGCGGATCATGA
AGCGGGAGTACCAGGACGCCGGAGGGAGCGGCGGCGGCGGTGGCGGCATGGGT
TCGTCCGAGGACAAGATGATGGTGTCGGCGGCGGCGGGGGAGGGGGAGGAGGT
GGACGAGCTGCTGGCGGCGCTCGGGTACAAGGTGCGCGCCTCCGACATGGCGGA
CGTGGCGCAGAAGCTGGAGCAGCTCGAGATGGCCATGGGGATGGGCGGCGTGGG
CGCCGGCGCCGCCCCCGACGACAGCTTCGCCACCCACCTCGCCACGGACACCGTG
CAGTACAACCNCCCNGACC

Figure 2b(10)

GGACGACGACCTCCGAGCCGACCACCACCGGCATGTAGTAATGTAATCCCTTCTT
CNTTCCCAGTNCTCCACCGCCTCCATGATCACCCGTAAAACTCCTAAGCCCTATT
ATTACTACTATTATGTNTAANTGTCTATTATTGCTANGTGTAATTCCTCCAACCGC
TCATATCAAAATAAGCACGGGCCGGACTTTGTTANCAGCTCCAATGAGAATGAA
ATGAATTTTGTACGCAAGGCACGTCCAAAACTGGGCTGAGCTTTGTTCTGTTCTG
TTATGTTCATGGTGCTCACTGCTCTGATGAACATGATGGTGCCTCCAATGGTGGC
TTTGCAATTGTTGAAACGTTTGGCTTGGGGGACTTGNGTGGGTGGGTGCATGGGG
ATGAATATTCACATCNCCGGATTAAAATTAAGCCATCCCGTTGGCCGTCCTTTGA
ATANCTTGCCCNAAACGAAATTTCCCCCNATC

Figure 2b(11)

AAANCCTANAANATATAGAGGCGATGTNGCNCCCCNATCANNAACNGGATTACN
GNAACNCCNGAAGGAGCGGCGGCGGCGGTGGCAGCATNGGCTCGTCCGATGACA
AATATCATGGTGTCGGCGGCGGCGGGGGACGGGGAGGAGGTGCACAACNTTTNG
GCGGGACTCGNGTACCACGTGNACGGTGCCGCNCTNGNGGATNTGGCCCTNGAA
GATGGGCCACCTCCAAA

Figure 2b(12)

CGGCGGCCCCGTGGCGGCATGGGCTCGTCCGAGGACNAGATGATGGTGTCGGCG
GCGGCGGGGGANGGGGATGATGTGGACTATCTGCTGGCGGCGCTCGGGTACAAG
GTGCGCGCCTCCGACAGGCGGAGCCCGCGCATAACTGGAGCCGCTCGAGATGGC
CNTGGGGATNGGCGGCNTGGGCNCCNGCGCCTCCCCCG

Figure 2b(13)

TGGNGCTCGGGTGNCCCGTGCGCGCCTCCGACATGGCGGGACGTGGCGCAGAAC
TGGAGCAGCTCGAGATGGCCATGGGGATGGGCGGCGTGGGCGCCGGCGCCGCCC
CCGACGACAGCTTCGCCACCCACCTCGCCACGGACACCGGCACACAACCCCACCG
ACCTGTCGTCTTGGGTCGAGAGCATGCTGTCGGATCTCNACGCGCCNCCGNCGCC
CCTCCCGCCCGC

Figure 2c(1)

ANNTTGTNCNNNNTACATCCCATGNGCCGCGCNATGCTNAAGGTCGCCGCCTACT
TCGGCGCAGGCCCTCGCCCGCCGCGTCTTCCGCTTCCGCCCGCAGCCGGACAGCT
CCCTCCTCGACGCCGCCTTCGCCGACCTCCTCCACGCGCACTTCTACGAGTCCTGC
CCCTACCTCAAGTTCGCGCACTTCACCGCCAACCAGGCCATCCTGGAGGCGTTCG
CCGGCTGCCGCCGCGTGCACGTCGTCGACTTCGGCATCAAGCAGGGGATGCAGT
GGCCCGCACTTCTCCAGGCCCTCGCCCTCCGTCCCGGCGGCCCTCCCTCGTTCCGC
CTCACCGGCGTTCGGCCCCCGCAGCCGGACGANAACGACGCCCTG

Figure 2c(2)

NTTCCCCGGCAGTTAAAAGCNTCCACTTCTTCCACCGTCACGGGCAGCGGCGGNT
ACTTNGATCTCCCGCCCTCAGTCGACTCCTCCAGCAGCATCTACGCGCTGCGGCC
GATCCCCTCCCCGGCCGGCGCGACGGCGCCGGCCGACCTGTCCGCCGACTCCGTG
CGGGATCCCAAGCGGATGCGCACTGGCGGGAGCAGCACCTCGTCGTCATCCTCCT
CATANTCGTCTCTCGGTGGGGCGCCAGGAGCTCTGTGGTGGAGGCNGCCCCGCC
GGTCGCGGCCGCGGCCAACGCGACGCCCGCGCTGCCGGTCGTCGTGGTCGACAC
GCAGGAGGCCGGGATTCGGATGGTGCACGCGCTGNTGGCGTGCGCGGAGGCCGT
GNAAGCAGTTNGAAGGGCCTNCGCCGTGNATNNCGCAACAANNNGGAAGNCCN

Figure 2c(3)

CANCCCGCTGNTCGCCACCTCGGCATGGCGCCTGGCCGGGCCGTGATCTCGCGAG
TTTTGAACGCTGTAAGTACACATCGTGAGCATGGAGGACAACACAGCCCCGGCG
GCCGCCCCGGCTCTCCGGCGAACGCACGCACGCACGCACTTGAAGAAGAAGAAG
CTAAATGTCATGTCAGTGAGCGCTGAATTGCANCGACCGGCTACGATCGATCGG
GCTACGGGTGGTTCCGTCCGTCTGGCGTGAAGAGGTGGATGGACGACGAACTCC
GANCCGACCACCACCGGCATGTAGTAATGTAATCCCTTCTTCGTTCCCAGTTTCTC
CACCGCCTCCATGATCACCCCGTAAAACTCCTAAGCCCTATNNNTTACTACNATT
AATGTTTTAAANTGTTCTANTAATTGCTATGNTGTTTATTNCC

Figure 2c(4)

TATCGAAGTAGCCGCCGCTGCCCNTGCACGGTGGAGGAGGTGGAGGCGTTGAGC
TGCGGGGCGGGCGGGAGGGGCGGCGGCGGCACGTTNAGCTCCGACAGCATGCTC
TCGACCCAAAACNACAGGTCGGTGGGGTTGTAGTGCACGGTGTCCGTGGCGAGG
GGGTGGCNAANCTGTCGTCAGGGGCGGCGCCNGCGCCCACNCCGCCCATCCCCA
TGGCCATCTCGANCTGCTCCAGCTTCTGCGCCACTTCCNCCATGTCNGATGCGCG
CNCCTTGTACCCGA

Figure 2c(5)

ACGGCGCGGNCCNCGCNNGCTTGGGAGGGGATCGGCCGCAGCGCNTANATGCTG
CTGGAGGAGTCGACGGAGGGCGGGAGATCGAACTAGCCGCCGCTGCCCGTGTAC
GGTGGAGGAGGTGGAGGCGTTGAGCTGCGGGGCGGGCGGGAGGGGCAGCNGCT
GCACGTTNAGCTCCCACACCACGTCTCTCAACCCAACCACGACNCGTCTGTGGGG
TNGTAATNCACGGTNTCCCTNGCTANGTGGGTGGCCAATCTNT

Figure 2c(6)

CACGGTGTCCGTGGCGAGGTGGGTGGCGAAGCTGTCGTCGGGGGCGGCGCCGGC
GCCCACGCCGCCCATCCCCATGGCCATCTCGAGCTGCTCCAGCTTCTGCGCCACG
TCCGCCATGTCGGAGGCGCGCACCTTGTACCCGAGCGCCGCCAGCAGCNCGNCC
ACCTCCTCCCCCTCCCCGCCGCCGCCGACACCATCATCTTGTCCTCGGACGANCC
CATGCCGCCACCGCCGCCGCCGCTCCCTCCGGCGTCCTGGTACTCCCGCTTCATG
ATCCGCGAGCTACCTCGCCTCTCTATCTATCTCTGGCCAATAATTGCGCA

Figure 2c(7)

GACCACCACCGGCATGTAGTAATGTAATCCCTTCTTCNTTCCCAGTTCTCCACCGC
CTCCATGATCACCCGTAAAACTCCTAAGCCCTATTATTACTACTATTATGTNTAA
ATGTCTATTATTGCTANGTGTAATTCCTCCAACCGCTCATATCAAAATAAGCACG
GGCCGGACTTTGTTAGCAGCTCCAATGAGAATGAAATGAATTTTGTACGCAAGGC
ACGTCCAAAACTGGGCTGAGCTTTGTTCTGTTCTGTTATGTTCATGGTGCTCACTG
CTCTGATGAACATGATGGTGCCTCCAATGGGTGGCTTTGCAATTGTTGAACGTTT
TGGCTTGGGGGACTTGGTGNNTGGTGCATGGGAATGAANATTCCACATCCNCNG
GAATTAAAATTAGCCCATCCCG

Figure 3a

```
TTTCANTTTCNTCCTTTTTTCTTCTTTTTCCAACCCCCGGCCCCCNGACCCTTGGATCC
AAATCCCGAACCCGCCCCCAGAACCNGGAACCGAGGCCAAGCAAAAGNTTTGCGCC
AATTATTGGCCAGAGATAGATAGAGAGGCGAGGTAGCTCGCGGATCATGAAGCGGG
AGTACCAGGACGCCGGAGGGAGCGGCGGCGGCGGTGGCGGCATGGGTTCGTCCGAG
GACAAGATGATGGTGTCGGCGGCGGCGGGGGAGGGGGAGGAGGTGGACGAGCTGC
TGGCGGCGCTCGGGTACAAGGTGCGCGCCTCCGACATGGCGGACGTGGCGCAGAAG
CTGGAGCAGCTCGAGATGGCCATGGGGATGGGCGGCGTGGGCGCTGGCGCCGCCCC
TGACGACAGGTTNGCCACCCGCNGGCCGCGGACACNGTGCANTACAACCCCACNGA
CNTGTCGTCTTGGGTCGAGAGCATGCTGTCGGAGCTAAANGAGCCGCNGCCGCCCC
TCCCGCCCGCCCCGCAGCTCAACGCCTCCACCGTCACGGGCAGCGGCGGNTACTTNG
ATCTCCCGCCCTCAGTCGACTCCTCCAGCAGCATCTACGCGCTGCGGCCGATCCCCT
CCCCGGCCGGCGCGACGGCGCCGGCCGACCTGTCCGCCGACTCCGTGCGGGATCCC
AAGCGGATGCGCACTGGCGGGAGCAGCACCTCGTCGTCATCCTCCTCATANTCGTCT
CTCGGTGGGGGCGCCAGGAGCTCTGTGGTGGAGGCNGCCCGCCGGTCGCGGCCGC
GGCCAACGCGACGCCCGCGCTGCCGGTCGTCGTGGTCGACACGCAGGAGGCCGGGA
TTCGGCTGGTGCACGCGCTGCTGGCGTGCGCGGAGGCCGTGCAGCAGGAGAACCTC
TCCGCCGCGGAGGCGCTGGTGAAGCAGATACCCTTGCTGGCCGCGTCCCAGGGCGG
CGCGATGCGCAAGGTCGCCGCCTACTTCGGCGAGGCCCTCGCCCGCCGCGTCTTCCG
CTTCCGCCCGCAGCCGGACAGCTCCCTCCTCGACGCCGCCTTCGCCGACCTCCTCCA
CGCGCACTTCTACGAGTCCTGCCCCTACCTCAAGTTCGCGCACTTCACCGCCAACCA
GGCCATCCTGGAGGCGTTCGCCGGCTGCCGCCGCGTGCACGTCGTCGACTTCGGCAT
CAAGCAGGGGATGCAGTGGCCCGCACTTCTCCAGGCCCTCGCCCTCCGTCCCGGCGG
CCCTCCCTCGTTCCGCCTCACCGGCGTCGGCCCCCCGCAGCCGGACGAGACCGACGC
CCTGCAGCAGGTGGGCTGGAAGCTCGCCCAGTTCGCGCACACCATCCGCGTCGACTT
CCAGTACCGCGGCCTCGTCGCCGCCACGCTCGCGGACCTGGAGCCGTTCATGCTGCA
GCCGGAGGGCGAGGAGGACCCGAACGAAGANCCCGANGTAATCGCCGTCAACTCA
GTCTTCGAGATGCACCGGCTGCTCGCGCAGCCCGGCGCCCTGGAAAAGGTTCTTGGG
CACCGTGCGCCCCGTGCGGCCCAGAATTCNTCACCGTGGTGGAAACAGGAGGCAA
ATCACAACTCCGGCACATTCCTGGACCGCTTCACCGAGTCTCTGCACTACTACTCCA
CCATGTTCGATTCCCTCGAGGGCGGCAGCTCCGGCGGCGGCCCATCCGAAGTCTCAT
CGGGGGCTGCTGCTGCTCCTGCCGCCGCCGGCACGGACCAGGTCATNTCCGAGGTGT
ACCTCGGCCGGCAGATCTGCAACGTGGTGGCCTGCGAGGGGGCGGAACGCACAGAN
CGCCACGAGACGCTGGGCCAGTGGCGGAACCGGCTGGGCAACGCCGGGTTCGAGAC
CGTCCACCTGGGCTCCAATGCCTACAAGCAGGCGANCACGCTGCTGGCGCTCTTCGC
CGGCGGCGAACGGCTACANGTGGAAGAAAAGGAAGGCTGCCTGACGCTGGGGTTGC
ACACNCCCCCTGATTGCCACCTCGGCATGGCGCCTGGCCGGGCCGTGATCTCGCGA
GTTTTGAACGCTGTAAGTACACATCGTGAGCATGGAGGACAACACAGCCCCGGCGG
CCGCCCCGGCTCTCCGGCGAACGCACGCACGCACGCACTTGAAGAAGAAGAAGCTA
AATGTCATGTCAGTGAGCGCTGAATTGCAGCGACCGGCTACGATCGATCGGGCTAC
GGGTGGTTCCGTCCGTCTGGCGTGAAGAGGTGGATGGACGACGAACTCCGAGCCGA
CCACCACCGGCATGTAGTAATGTAATCCCTTCTTCGTTCCCAGTTCTCCACCGCCTCC
ATGATCACCCGTAAAACTCCTAAGCCCTATTATTACTACTATTATGTTTAAATGTCTA
TTATTGCTATGTGTAATTCCTCCAACCGCTCATATCAAAATAAGCACGGGCCGGACT
TTGTTANCAGCTCCAATGAGAATGAAATGAATTTTGTACGCAAGGCACGTCCAAAA
CTGGGCTGAGCTTTGTTCTGTTCTGTTATGTTCATGGTGCTCACTGCTCTGATGAACA
TGATGGTGCCTCCAATGGTGGCTTTGCAATTGTTGAAACGTTTGGCTTGGGGGACTT
GNGTGGGTGGGTGCATGGGGATGAATATTCACATCNCCGGATTAAAATTAAGCCAT
CCCGTTGGCCGTCCTTTGAATANCTTGCCCNAAACGAAATTTCCCCCNATC
```

Figure 3b

PRETTYBOX of: My.Msf(*)  August 7, 1997 13:06:42.76

```
Gai  .....IM  KRDHHHHQ. .......D  KRTMMNEED  DGNGMDELLA  VLGYKVRSSE   41
Rht  IERRGSRIM  KREYQDAGGS  GGGGGMGSE  DRMMVSAAAG  EGEEVDELLA  ALGYKVRASD   60

Gai  HADVAQKLEQ  LEVMMS...  .NVQEDD  LSQLATBTVH  YNPAELYTML  DSMLTDLNPP   93
Rht  HADVAQKLEQ  LEMANGMGGV  GAGAAPDRQV  XHPXAADTVX  YNPTDXSSHV  ESMLSELXEP  120

Gai  XPPLPPAPQL  ...  NASTVTGSGG  .......  SNAEYDLKAH  PGDAILNQFA  IDSASSNQ.  123
Rht  XPPLPPAPQL  NASTVTGSGG  YXDLPPSVDS  SSSIVALRPI  PSPAGATAPA  DLSADSVRDP  180

Gai  ...GGGGDT  YTTNKRLKCS  NG....VVE  .......  AESTRHVVLV  DSQENGVRLV  169
Rht  KRMRTGGSST  SSSSSXSSL  GGGARSSVVE  AAPPVAAAAN  ATPALPVVV  DTOEAGIRLV  240

Gai  HALLACAEAV  QKENLTVAEA  LVKQIGFLAV  TYFAEALARR  IYRLSPSQ.  227
Rht  HALLACAEAV  OQENLSAAEA  LVKQIPLLAA  AYFGEALARR  VFRFRPQPDS  300

Gai  SPIDHSLSDT  LQMHFYETCP  YLKFAHFTAN  KRVHVIDESM  SQGLQWPALM  287
Rht  SLLDAAFADL  LHAHFYESCP  YLKFAHFTAN  RRVHVVDFGI  KOGMOWPALL  360

Gai  QALALRPGGP  PVFRLTGIGP  PAPDNFDYLH  EAIHVEFEYR  GFVANTLADL  347
Rht  QALALRPGGP  PSFRLTGVGP  POPDETDALQ  HTIRVDFQYR  GLVAATLADL  420

Gai  DASMLELRPS  EIES....V  AVNSVFELHK  LLGRPGAIDK  PEIFTVVE.Q  400
Rht  RPFMLQPEGE  EDPNEXPXVI  AVNSVFEMHR  LLAQPGALEK  PEFXTVVETQ  480

Gai  ESNHNSPIEL  DRFTESLHYY  STLFDSLEGV  PSGQ....  VLG.VVNQIK  .DKVMSEVY  442
Rht  EANHNSGTFL  DRFTESLHYY  STMFDSLEGG  SSGGGPSEVS  VLGHRAPPCG  GTDQVXSEVY  540

Gai  LGKQICNVVA  CDGPDRVERH  ETLSQORNRF  GSAGFAAAHI  GSNAFKQASM  LLALFNGGEG  502
Rht  LGROICNVVA  CBGAERTXRH  ETLGQRNRL  GNAGFETVHL  GSNAYKQAXT  LLALFAGGER  600

Gai  YRVEESDGCL  MLGWHTRPLI  ATSAWKLSTN  532
Rht  LXVEEKEGCL  TLGLHTXPLI  ATSAVRLAGP  630
```

Figure 4a

ACGCGTCCGGAAGCCGGCGGGAGCAGCGGCGGCGGGAGCAGCGCCGATATGGG
GTCGTGCAAGGACAAGGTGATGGCGGGGGCGGCGGGGGAGGAGGAGGACGTCT
ACGAGCTGCTGGCGGCGCTCGGGTACAAGGTGCGGTCGTCCGACATGGCCGACG
TCGCGCAGAANCTGGAGCAGCTGGAGATGGCCATGGGGATGGGCGGCGTGAGCG
CCCCCGGCGCCGCGGATGACGGGTTCGTGTCGCACCTGGCCACGGACACCGTGC
ACTACAACCCCTCGGACCTCTCCTCCTGGGTTCNGAGAGCATGCTTTCGGAGTTA
AAGGCGCCGTTGCCCCTTATCCCGCCAGGCGCCGCCGGGCTGCCCGCCATGCTTT
CCAACTTCGTCCACTGTCACCGGCGGCGGTGGTAGCGGCTTCTTTGAANTCCCAG
CCGCTGCCGANTCGTCGAGTAGCACNTACGCCCTCAGGCCGATCTCCTTACCGGT
GGTGGCGACGGCTGACCCGTCGGCTGCTGACTCGGCGAGGGACACCAAGCGGAT
GCGCACTGGCGGCGGCAGCACGTCGTCGTCCTCATCGTCGTCTTCCTCTCTGGGC
GGTGGGCCTCGCGGGGCTCTGTGGTGGAGGCTGCTCCGCCGGCGACGCAAGGG
GCCGCGGCGGCGAATGCGCCCGCCGTGCCGGTTGTGGTGGTTGACACGCAGGAG
GCTGGNATCGGGCCTGGTGC

GTCGACCCACGCGTCCGGAAGCCGGCGGGAGCAGCGGCGGCGGGAGCAGCGCC
GATATGGGGTCGTGCAAGGACAAGGTGATGGCGGGGGCGGCGGGGGAGGAGGA
GGACGTCGACGAGCTGCTGGCGGCGCTCGGGTACAAGGTGCGGTCGTCCGACAT
GGCCGACGTCGCGCAGAAGCTGGAGCAGCTGGAGATGGCCATGGGGATGGGCGG
CGTGAGCGCCCCCGGCGCCGCGGATGACGGGTTCGTGTCGCACCTGGCCACGGA
CACCGTGCACTACAACCCCTCGGACCTCTCCTCCTGGGTCGAGAGCATGCTTTCC
GAGCTCAACGCGCCGCTGCCCCCTATCCCGCCAGCGCCGCCGGCTGCCCGCCATG
CTTCCACCTCGTCCACTGTCACCGGCGGCGGTGGTAGCGGCTTCTTTGAACTCCC
AGCCGCTGCCGACTCGTCGAGTAGCACCTACGCCCTCAGGCCGATCTCCTTACCG
GTGGTGGCGACGGCTGACCCGTCGGCTGCTGACTCGGCGAGGGACACCAAGCGG
ATGCGCACTGGCGGCGGCAGCACGTCGTCGTCCTCATCGTCGTCTTCCTCTCTGG
GCGGTGGGGCCTCGCGGGGCTCTGTGGTGGAGGCTGCTCCGCCGGCGACGCAAG
GGGCCGCGGCGGCGAATGCGCCCGCCGTGCCGGTTGTGGTGGTTGACACGCAGG
AGGCTGGGATCCGGCTGGTGCACGCGTTGCTGGCGTGCGCGGAGGCCGTGCAGC
AGGAGAACTTC

Figure 6b

RPTRPEAGGSSGGGSSADMGSCKDKVMAGAAGEEEDVDELLAALGYKVRSSDMAD
VAQKLEQLEMAMGMGGVSAPGAADDGFVSHLATDTVHYNPSDLSSWVESMLSELN
APLPPIPPAPPAARHASTSSTVTGGGGSGFFELPAAADSSSSTYALRPISLPVVATADPS
AADSARDTKRMRTGGGSTSSSSSSSSSLGGGASRGSVVEAAPPATQGAAAANAPAVP
VVVVDTQEAGIRLVHALLACAEAVQQENF

Figure 7a

GCCAGGAGCTCTGTGGTGGAGGCTGCCCCGCCGGTCGCGGCCGCGGCCAACGCG
ACGCCCGCGCTGCCGGTCGTCGTGGTCGACACGCAGGAGGCCGGGATTCGGCTG
GTGCACGCGCTGCTGGCGTGCGCGGAGGCCGTGCAGCAGGAGAACCTCTCCGCC
GCGGAGGCGCTGGTGAAGCAGATACCCTTGCTGGCCGCGTCCCAGGGCGGCGCG
ATGCGCAAGGTCGCCGCCTACTTCGGCGAGGCCCTCGCCCGCCGCGTCTTCCGCT
TCCGCCCGCAGCCGGACAGCTCCCTCCTCGACGCCGCCTTCGCCGACCTCCTCCA
CGCGCACTTCTACGAGTCCTGCCCCTACCTCAAGTTCGCGCACTTCACCGCCAAC
CAGGCCATCCTGGAGGCGTTCGCCGGCTGCCGCCGCGTGCACGTCGTCGACTTCG
GCATCAAGCAGGGGATGCAGTGGCCCGCACTTCTCCAGGCCCTCGCCCTCCGTCC
CGGCGGCCCTCCCTCGTTCCGCCTCACCGGCGTCGGCCCCCCGCAGCCGGACGAG
ACCGACGCCCTGCAGCAGGTGGGCTGGAAGCTCGCCCAGTTCGCGCACACCATC
CGCGTCGACTTCCAGTACCGCGGCCTCGTCGCCGCCACGCTCGCGGACCTGGAGC
CGTTCATGCTGCAGCCGGAGGGCGAGGAGGACCCGAACGAGGAGCCCGAGGTAA
TCGCCGTCAACTCAGTCTTCGAGATGCACCGGCTGCTCGCGCAGCCCGGCGCCCT
GGAGAAGGTCCTGGGCACCGTGCGCGCCGTGCGGCCCAGGATCGTCACCGTGGT
GGAGCAGGAGGCGAATCACAACTCCGGCACATTCCTGGACCGCTTCACCGAGTC
TCTGCACTACTACTCCACCATGTTCGATTCCCTCGAGGGCGGCAGCTCCGGCGGC
GGCCCATCCGAAGTCTCATCGGGGGCTGCTGCTGCTCCTGCCGCCGCCGGCACGG
ACCAGGTCATGTCCGAGGTGTACCTCGGCCGGCAGATCTGCAACGTGGTGGCCTG
CGAGGGGGCGGAGCGCACAGAGCGCCACGAGACGCTGGGCCAGTGGCGGAACC
GGCTGGGCAACGCCGGGTTCGAGACCGTCCACCTGGGCTCCAATGCCTACAAGC
AGGCGAGCACGCTGCTGGCGCTCTTCGCCGGCGGCGACGGCTACAAGGTGGAGG
AGAAGGAAGGCTGCCTGACGCTGGGGTGGCACACGCGCCCGCTGATCGCCACCT
CGGCATGGCGCCTGGCCGGGCCGTGATCTCGCGAGTTTTGAACGCTGTAAGTACA
CATCGTGAGCATGGAGGACAACACAGCCCCGGCGGCCGCCCCGGCTCTCCGGCG
AACGCACGCACGCACGCACTTGAAGAAGAAGAAGCTAAATGTCATGTCAGTGAG
CGCTGAATTGCAGCGACCGGCTACGATCGATCGGGCTACGGGTGGTTCCGTCCGT
CTGGCGTGAAGAGGTGGATGGACGACGAACTCCGAGCCGACCACCACCGGCATG
TAGTAATGTAATCCCTTCTTCGTTCCCAGTTCTCCACCGCCTCCATGATCACCCGT
AAAACTCCTAAGCCCTATTATTACTACTATTATGTTTAAATGTCTATTATTGCTAT
GTGTAATTCCTCCAACCGCTCATATCAAAATAAGCACGGGCCGGAAAAAAAAAA
AAAAAAAAAAAAAAAAAAAAAAAAAAAAAAAAAAAAAAAAAAAAAAAAAAAAA
AAAAAAAAAAAAAAAAAAAAAAAAA

Figure 7b

ARSSVVEAAPPVAAAANATPALPVVVVDTQEAGIRLVHALLACAEAVQQENLSAAE
ALVKQIPLLAASQGGAMRKVAAYFGEALARRVFRFRPQPDSSLLDAAFADLLHAHF
YESCPYLKFAHFTANQAILEAFAGCRRVHVVDFGIKQGMQWPALLQALALRPGGPPS
FRLTGVGPPQPDETDALQQVGWKLAQFAHTIRVDFQYRGLVAATLADLEPFMLQPE
GEEDPNEEPEVIAVNSVFEMHRLLAQPGALEKVLGTVRAVRPRIVTVVEQEANHNSG
TFLDRFTESLHYYSTMFDSLEGGSSGGGPSEVSSGAAAAPAAAGTDQVMSEVYLGR
QICNVVACEGAERTERHETLGQWRNRLGNAGFETVHLGSNAYKQASTLLALFAGGD
GYKVEEKEGCLTLGWHTRPLIATSAWRLAGP

Figure 8a

```
ATAGAGAGGCGAGGTAGCTCGCGGATCATGAAGCGGGAGTACCAGGACGCCGG
AGGGAGCGGCGGCGGCGGTGGCGGCATGGGCTCGTCCGAGGACAAGATGATGGT
GTCGGCGGCGGCGGGGGAGGGGGAGGAGGTGGACGAGCTGCTGGCGGCGCTCG
GGTACAAGGTGCGCGCCTCCGACATGGCGGACGTGGCGCAGAAGCTGGAGCAGC
TCGAGATGGCCATGGGGATGGGCGGCGTGGGCGCCGGCGCCGCCCCCGACGACA
GCTTCGCCACCCACCTCGCCACGGACACCGTGCACTACAACCCCACCGACCTGTC
GTCTTGGGTCGAGAGCATGCTGTCGGAGCTCAACGCGCCGCCGCCGCCCCTCCCG
CCCGCCCCGCAGCTCAACGCCTCCACCTCCTCCACCGTCACGGGCAGCGGCGGCT
ACTTCGATCTCCCGCCCTCCGTCGACTCCTCCAGCAGCATCTACGCGCTGCGGCC
GATCCCCTCCCCGGCCGGCGCGACGGCGCCGGCCGACCTGTCCGCCGACTCCGTG
CGGGATCCCAAGCGGATGCGCACTGGCGGGAGCAGCACCTCGTCGTCATCCTCCT
CCTCGTCGTCTCTCGGTGGGGGCGCCAGGAGCTCTGTGGTGGAGGCTGCCCCGCC
GGTCGCGGCCGCGGCCAACGCGACGCCCGCGCTGCCGGTCGTCGTGGTCGACAC
GCAGGAGGCCGGGATTCGGCTGGTGCACGCGCTGCTGGCGTGCGCGGAGGCCGT
GCAGCAGGAGAACCTCTCCGCCGCGGAGGCGCTGGTGAAGCAGATACCCTTGCT
GGCCGCGTCCCAGGGCGGCGCGATGCGCAAGGTCGCCGCCTACTTCGGCGAGGC
CCTCGCCCGCCGCGTCTTCCGCTTCCGCCCGCAGCCGGACAGCTCCCTCCTCGAC
GCCGCCTTCGCCGACCTCCTCCACGCGCACTTCTACGAGTCCTGCCCCTACCTCAA
GTTCGCGCACTTCACCGCCAACCAGGCCATCCTGGAGGCGTTCGCCGGCTGCCGC
CGCGTGCACGTCGTCGACTTCGGCATCAAGCAGGGGATGCAGTGGCCCGCACTTC
TCCAGGCCCTCGCCCTCCGTCCCGGCGGCCCTCCCTCGTTCCGCCTCACCGGCGTC
GGCCCCCCGCAGCCGGACGAGACCGACGCCCTGCAGCAGGTGGGCTGGAAGCTC
GCCCAGTTCGCGCACACCATCCGCGTCGACTTCCAGTACCGCGGCCTCGTCGCCG
CCACGCTCGCGGACCTGGAGCCGTTCATGCTGCAGCCGGAGGGCGAGGAAGACC
CGAACGAGGAGCCCGAGGTAATCGCCGTCAACTCAGTCTTCGAGATGCACCGGC
TGCTCGCGCAGCCCGGCGCCCTGGAGAAGGTCCTGGGCACCGTGCGCGCCGTGC
GGCCCAGGATCGTCACCGTGGTGGAGCAGGAGGCGAATCACAACTCCGGCACAT
TCCTGGACCGCTTCACCGAGTCTCTGCACTACTACTCCACCATGTTCGATTCCCTC
GAGGGCGGCAGCTCCGGCGGCGGCCCATCCGAAGTCTCATCGGGGGCTGCTGCT
GCTCCTGCCGCCGCCGGCACGGACCAGGTCATGTCCGAGGTGTACCTCGGCCGGC
AGATCTGCAACGTGGTGGCCTGCGAGGGGGCGGAGCGCACAGAGCGCCACGAGA
CGCTGGGCCAGTGGCGGAACCGGCTGGGCAACGCCGGGTTCGAGACCGTCCACC
TGGGCTCCAATGCCTACAAGCAGGCGAGCACGCTGCTGGCGCTCTTCGCCGGCGG
CGACGGCTACAAGGTGGAGGAGAAGGAAGGCTGCCTGACGCTGGGGTGGCACAC
GCGCCCGCTGATCGCCACCTCGGCATGGCGCCTGGCCGGGCCGTGATCTCGCGAG
TTTTGAACGCTGTAAGTACACATCGTGAGCATGGAGGACAACACAGCCCCGGCG
GCCGCCCCGGCTCTCCGGCGAACGCACGCACGCACGCACTTGAAGAAGAAGAAG
CTAAATGTCATGTCAGTGAGCGCTGAATTGCAGCGACCGGCTACGATCGATCGGG
CTACGGGTGGTTCCGTCCGTCTGGCGTGAAGAGGTGGATGGACGACGAACTCCG
```

Figure 8b

```
MKREYQDAGGSGGGGGGMGSSEDKMMVSAAAGEGEEVDELLAALGYKVRASDM
ADVAQKLEQLEMAMGMGGVGAGAAPDDSFATHLATDTVHYNPTDLSSWVESMLS
ELNAPPPPLPPAPQLNASTSSTVTGSGGYFDLPPSVDSSSSIYALRPIPSPAGATAPADL
SADSVRDPKRMRTGGSSTSSSSSSSSSLGGGARSSVVEAAPPVAAAANATPALPVVV
VDTQEAGIRLVHALLACAEAVQQENLSAAEALVKQIPLLAASQGGAMRKVAAYFGE
ALARRVFRFRPQPDSSLLDAAFADLLHAHFYESCPYLKFAHFTANQAILEAFAGCRR
VHVVDFGIKQGMQWPALLQALALRPGGPPSFRLTGVGPPQPDETDALQQVGWKLA
QFAHTIRVDFQYRGLVAATLADLEPFMLQPEGEEDPNEEPEVIAVNSVFEMHRLLAQ
PGALEKVLGTVRAVRPRIVTVVEQEANHNSGTFLDRFTESLHYYSTMFDSLEGGSSG
GGPSEVSSGAAAAPAAAGTDQVMSEVYLGRQICNVVACEGAERTERHETLGQWRN
RLGNAGFETVHLGSNAYKQASTLLALFAGGDGYKVEEKEGCLTLGWHTRPLIATSA
WRLAGP
```

Figure 9a

TTTCGCCTGCCGCTGCTATTAATAATTGCCTTCTTGGTTTCCCCGTTTTCGCCCCAG
CCGCTTCCCCCCTCCCCTACCCTTTCCTTCCCCACTCGCACTTCCCAACCCTGGAT
CCAAATCCCAAGCTATCCCAGAACCGAAACCGAGGCGCGCAAGCCATTATTAGC
TGGCTAGCTAGGCCTGTAGCTCCGAAATCATGAAGCGCGAGTACCAAGACGCCG
GCGGGAGTGGCGGCGACATGGGCTCCTCCAAGGACAAGATGATGGCGGCGGCGG
CGGGAGCAGGGGAACAGGAGGAGGAGGACGTGGATGAGCTGCTGGCCGCGCTC
GGGTACAAGGTGCGTTCGTCGGATATGGCGGACGTCGCGCAGAAGCTGGAGCAG
CTCGAGATGGCCATGGGGATGGGCGGCGTGGGCGGCGCCGGCGCTACCGCTGAT
GACGGGTTCGTGTCGCACCTCGCCACGGACACCGTGCACTACAATCCCTCCGACC
TGTCGTCCTGGGTCGAGAGCATGCTGTCCGAGCTCAACGCGCCCCAGCGCCGCT
CCCGCCCGCGACGCCGGCCCCAAGGCTCGCGTCCACATCGTCCACCGTCACAAGT
GGCGCCGCCGCCGGTGCTGGCTACTTCGATCTCCCGCCCGCCGTGGACTCGTCCA
GCAGTACCTACGCTCTGAAGCCGATCCCCTCGCCGGTGGCGGCGCCGTCGGCCGA
CCCGTCCACGGACTCGGCGCGGGAGCCCAAGCGGATGAGGACTGGCGGCGGCAG
CACGTCGTCCTCCTCTTCCTCGTCGTCATCCATGGATGGCGGTCGCACTAGGAGCT
CCGTGGTCGAAGCTGCGCCGCCGGCGACGCAAGCATCCGCGGCGGCCAACGGGC
CCGCGGTGCCGGTGGTGGTGGTGGACACGCAGGAGGCCGGGATCCGGCTCGTGC
ACGCGCTGCTGGCGTGCGCGGAGGCCGTGCAGCAGGAGAACTTCTCTGCGGCGG
AGGCGCTGGTCAAGCAGATCCCCATGCTGGCCTCGTCGCAGGGCGGTGCCATGC
GCAAGGTCGCCGCCTACTTCGGCGAGGCGCTTGCCCGCCGCGTGTATCGCTTCCG
CCCGCCACCGGACAGCTCCCTCCTCGACGCCGCCTTCGCCGACCTCTTGCACGCG
CACTTCTACGAGTCCTGCCCCTACCTGAAGTTCGCCCACTTCACCGCGAACCAGG
CCATCCTCGAGGCCTTCGCCGGCTGCCGCCGCGTCCACGTCGTCGACTTCGGCAT
CAAGCAGGGGATGCAGTGGCCGGCTCTTCTCCAGGCCCTCGCCCTCCGCCCTGGC
GGCCCCCCGTCGTTCCGGCTCACCGGCGTCGGGCCGCCGCAGCCCGACGAGACC
GACGCCTTGCAGCAGGTGGGCTGGAAACTTGCCCAGTTCGCGCACACCATCCGCG
TGGACTTCCAGTACCGTGGCCTCGTCGCGGCCACGCTCGCCGACCTGGAGCCGTT
CATGCTGCAACCGGAGGGCGATGACACGGATGACGAGCCCGAGGTGATCGCCGT
GAACTCCGTGTTCGAGCTGCACCGGCTTCTTGCGCAGCCCGGTGCCCTCGAGAAG
GTCCTGGGCACGGTGCGCGCGGTGCGGCCGAGGATCGTGACCGTGGTCGAGCAG
GAGGCCAACCACAACTCCGGCACGTTCCTCGACCGCTTCACCGAGTCGCTGCACT
ACTACTCCACCATGTTCGATTCTCTCGAGGGCGCCGGCGCCGGCTCCGGCCAGTC
CACCGACGCCTCCCCGGCCGCGGCCGGCGGCACGGACCAGGTCATGTCGGAGGT
GTACCTCGGCCGGCAGATCTGCAACGTGGTGGCGTGCGAGGGCGCGGAGCGCAC
GGAGCGCCACGAGACGCTGGGCCAGTGGCGCAGCCGCCTCGGCGGCTCCGGGTT
CGCGCCCGTGCACCTGGGCTCCAATGCCTACAAGCAGGCGAGCACGCTGCTGGC
GCTCTTCGCCGGCGGCGACGGGTACAGGGTGGAGGAGAAGGACGGGTGCCTGAC
CCTGGGGTGGCATACGCGCCCGCTCATCGCCACCTCGGCGTGGCGCGTCGCCGCC
GCCGCCGCTCCGTGATCAGGGAGGGGTGGTTGGGCTTCTGGACGCCGATCAAG
GCACACGTACGTCCCCTGGCATGGCGCACCCTCCCTCGAGCTCGCCGGCACGGGT
GAAGCTACCCGGGGGATCCACTAATTCTAAAACGGCCCCACCGCGGTGGAACTC
CACCTTTTGTTCCCTTTA

Figure 9b

MKREYQDAGGSGGDMGSSKDKMMAAAAGAGEQEEEDVDELLAALGYKVRSSDM
ADVAQKLEQLEMAMGMGGVGGAGATADDGFVSHLATDTVHYNPSDLSSWVESML
SELNAPPAPLPPATPAPRLASTSSTVTSGAAAGAGYFDLPPAVDSSSSTYALKPIPSPV
AAPSADPSTDSAREPKRMRTGGGSTSSSSSSSSSMDGGRTRSSVVEAAPPATQASAAA
NGPAVPVVVVDTQEAGIRLVHALLACAEAVQQENFSAAEALVKQIPMLASSQGGAM
RKVAAYFGEALARRVYRFRPPPDSSLLDAAFADLLHAHFYESCPYLKFAHFTANQAI
LEAFAGCRRVHVVDFGIKQGMQWPALLQALALRPGGPPSFRLTGVGPPQPDETDAL
QQVGWKLAQFAHTIRVDFQYRGLVAATLADLEPFMLQPEGDDTDDEPEVIAVNSVF
ELHRLLAQPGALEKVLGTVRAVRPRIVTVVEQEANHNSGTFLDRFTESLHYYSTMFD
SLEGAGAGSGQSTDASPAAAGGTDQVMSEVYLGRQICNVVACEGAERTERHETLGQ
WRSRLGGSGFAPVHLGSNAYKQASTLLALFAGGDGYRVEEKDGCLTLGWHTRPLIA
TSAWRVAAAAAP

TACCAAGACGCCGGCGGGAGTGGCGGCGACATGGGCTCCTCCAAGGACAAGATG
ATGGCGGCGGCGGCGGGAGCAGGGGAACAGGAGGAGGAGGACGTGGATGAGCT
GCTGGCCGCGCTCGGGTACAAGGTGCGTTCGTCGGATATGGCGGGGCTGGAGCA
GCTCGAGATGGCCATGGGGATGGGCGGCGTGGGCGGCGCCGGCGCTACCGCTGA
TGACGGGTTCGTGTCGCACCTCGCCACGGACACCGTGCACTACAATCCCTCCGAC
CTGTCGTCCTGGGTCGAGAGCATGCTGTCCGA

Figure 11b

YQDAGGSGGDMGSSKDKMMAAAAGAGEQEEEDVDELLAALGYKVRSSDMAGLEQ
LEMAMGMGGVGGAGATADDGFVSHLATDTVHYNPSDLSSWVESMLS

Figure 11c

TCCTCCAAGGACAAGATGATGGCGGCGGCGGCGGGAGCAGGGGAACAGGAGGA
GGAGGACGTGGATGAGCTGCTGGCCGCGCTCGGGTACAAGGTGCGTTCGTCGGA
TATGGCGGACGTCGCGCAGAAGCTGGAGCAGCTCGAGATGGCCATGGGGATGGG
CGGCGTGGGCGGCGCCGGCGCTACCGCTGATGACGGGTTCGTGTCGCACCTGTCG
TCCTGGGTCGAGAGCATGCTGTCCGAGCTCAACGCGCCCCAGCGCCGCTCCCGC
CCGCGACGCCGGCCCCAAGGCTCGCGTCCACATCGTCCACCGTCACAAGTGGCGC
CGCCGCCGGTGCTGGCTACTTCGATCTCCCGCCCGCCGTGGACTC

Figure 11d

SSKDKMMAAAAGAGEQEEEDVDELLAALGYKVRSSDMADVAQKLEQLEMAMGM
GGVGGAGATADDGFVSHLSSWVESMLSELNAPPAPLPPATPAPRLASTSSTVTSGAA
AGAGYFDLPPAVD

Figure 12a

GCGGCGCTCGGGTACAAGGTGCGCGCCTCCGACATGGCGGACGTGGCGCAGAAG
CTGGAGCAGCTCGAGATGGCCATGGGGATGGGCGGCGTGGGCGCCGGCGCCGCC
CCCGACGACAGCTTCGCCACCCACCTCGCCACGGACACCGTGCACTACAACCCCA
CCGACCTGTCGTCTTGGGTCGAGAGCATGCTGTCGGAGCTCAACGCCTCCACCTC
CTCCACCGTCACGGGCAGCGGCGGCTACTTCGATCTCCCGCCCTCCGTCGACTCC
TCCAGCAGCATCTACGCGCTGCGGCCGATCCCCTCCCCGGCCGGCGCGACGGCGC
CGGCCGACCTGTCCGCCGACTCCGTGCGGGATCCCAAGCGGATGCGCACTGGCG
GGAGCAGCACCTCGTCGTCATCCTCCTCCTCGTC

Figure 12b

AALGYKVRASDMADVAQKLEQLEMAMGMGGVGAGAAPDDSFATHLATDTVHYN
PTDLSSWVESMLSELNASTSSTVTGSGGYFDLPPSVDSSSSIYALRPIPSPAGATAPAD
LSADSVRDPKRMRTGGSSTSSSSSSS

SEQUENCE LISTING

<160> NUMBER OF SEQ ID NOS: 108

<210> SEQ ID NO 1
<211> LENGTH: 630
<212> TYPE: PRT
<213> ORGANISM: Triticum aestivum
<220> FEATURE:
<221> NAME/KEY: SITE
<222> LOCATION: (91)
<223> OTHER INFORMATION: Xaa is unknown or other amino acid
<221> NAME/KEY: SITE
<222> LOCATION: (94)
<223> OTHER INFORMATION: Xaa is unknown or other amino acid
<221> NAME/KEY: SITE
<222> LOCATION: (100)
<223> OTHER INFORMATION: Xaa is unknown or other amino acid
<221> NAME/KEY: SITE
<222> LOCATION: (106)
<223> OTHER INFORMATION: Xaa is unknown or other amino acid
<221> NAME/KEY: SITE
<222> LOCATION: (118)
<223> OTHER INFORMATION: Xaa is unknown or other amino acid
<221> NAME/KEY: SITE
<222> LOCATION: (121)
<223> OTHER INFORMATION: Xaa is unknown or other amino acid
<221> NAME/KEY: SITE
<222> LOCATION: (142)
<223> OTHER INFORMATION: Xaa is unknown or other amino acid
<221> NAME/KEY: SITE
<222> LOCATION: (197)
<223> OTHER INFORMATION: Xaa is unknown or other amino acid
<221> NAME/KEY: SITE
<222> LOCATION: (436)
<223> OTHER INFORMATION: Xaa is unknown or other amino acid
<221> NAME/KEY: SITE
<222> LOCATION: (438)
<223> OTHER INFORMATION: Xaa is unknown or other amino acid
<221> NAME/KEY: SITE
<222> LOCATION: (474)
<223> OTHER INFORMATION: Xaa is unknown or other amino acid
<221> NAME/KEY: SITE
<222> LOCATION: (536)
<223> OTHER INFORMATION: Xaa is unknown or other amino acid
<221> NAME/KEY: SITE
<222> LOCATION: (558)
<223> OTHER INFORMATION: Xaa is unknown or other amino acid
<221> NAME/KEY: SITE
<222> LOCATION: (589)
<223> OTHER INFORMATION: Xaa is unknown or other amino acid
<221> NAME/KEY: SITE
<222> LOCATION: (602)
<223> OTHER INFORMATION: Xaa is unknown or other amino acid
<221> NAME/KEY: SITE
<222> LOCATION: (617)
<223> OTHER INFORMATION: Xaa is unknown or other amino acid

<400> SEQUENCE: 1

Ile Glu Arg Arg Gly Ser Ser Arg Ile Met Lys Arg Glu Tyr Gln Asp
 1               5                  10                  15

Ala Gly Gly Ser Gly Gly Gly Gly Gly Met Gly Ser Glu Asp Lys
            20                  25                  30

Met Met Val Ser Ala Ala Ala Gly Glu Gly Glu Glu Val Asp Glu Leu
        35                  40                  45

Leu Ala Ala Leu Gly Tyr Lys Val Arg Ala Ser Asp Met Ala Asp Val
    50                  55                  60

Ala Gln Lys Leu Glu Lys Leu Glu Met Ala Met Gly Met Gly Gly Val
65                  70                  75                  80

Gly Ala Gly Ala Ala Pro Asp Arg Gln Val Xaa His Pro Xaa Ala Ala
                85                  90                  95

```
Asp Thr Val Xaa Tyr Asn Pro Thr Asp Xaa Ser Ser Trp Val Glu Ser
            100                 105                 110

Met Leu Ser Glu Leu Xaa Glu Pro Xaa Pro Leu Pro Pro Ala Pro
        115                 120                 125

Gln Leu Asn Ala Ser Thr Val Thr Gly Ser Gly Gly Tyr Xaa Asp Leu
        130                 135                 140

Pro Pro Ser Val Asp Ser Ser Ser Ile Tyr Ala Leu Arg Pro Ile
145                 150                 155                 160

Pro Ser Pro Ala Gly Ala Thr Ala Pro Ala Asp Leu Ser Ala Asp Ser
                165                 170                 175

Val Arg Asp Pro Lys Arg Met Arg Thr Gly Ser Ser Thr Ser Ser
            180                 185                 190

Ser Ser Ser Ser Xaa Ser Ser Leu Gly Gly Ala Arg Ser Ser Val
            195                 200                 205

Val Glu Ala Ala Pro Pro Val Ala Ala Ala Asn Ala Thr Pro Ala
    210                 215                 220

Leu Pro Val Val Val Asp Thr Gln Glu Ala Gly Ile Arg Leu Val
225                 230                 235                 240

His Ala Leu Leu Ala Cys Ala Glu Ala Val Gln Gln Glu Asn Leu Ser
                245                 250                 255

Ala Ala Glu Ala Leu Val Lys Gln Ile Pro Leu Leu Ala Ala Ser Gln
            260                 265                 270

Gly Gly Ala Met Arg Lys Val Ala Ala Tyr Phe Gly Glu Ala Leu Ala
            275                 280                 285

Arg Arg Val Phe Arg Phe Arg Pro Gln Pro Asp Ser Ser Leu Leu Asp
        290                 295                 300

Ala Ala Phe Ala Asp Leu Leu His Ala His Phe Tyr Glu Ser Cys Pro
305                 310                 315                 320

Tyr Leu Lys Phe Ala His Phe Thr Ala Asn Gln Ala Ile Leu Glu Ala
                325                 330                 335

Phe Ala Gly Cys Arg Arg Val His Val Val Asp Phe Gly Ile Lys Gln
            340                 345                 350

Gly Met Gln Trp Pro Ala Leu Leu Gln Ala Leu Ala Leu Arg Pro Gly
        355                 360                 365

Gly Pro Pro Ser Phe Arg Leu Thr Gly Val Gly Pro Pro Gln Pro Asp
    370                 375                 380

Glu Thr Asp Ala Leu Gln Gln Val Gly Trp Lys Leu Ala Gln Phe Ala
385                 390                 395                 400

His Thr Ile Arg Val Asp Phe Gln Tyr Arg Gly Leu Val Ala Ala Thr
            405                 410                 415

Leu Ala Asp Leu Glu Pro Phe Met Leu Gln Pro Glu Gly Glu Glu Asp
            420                 425                 430

Pro Asn Glu Xaa Pro Xaa Val Ile Ala Val Asn Ser Val Phe Glu Met
        435                 440                 445

His Arg Leu Leu Ala Gln Pro Gly Ala Leu Glu Lys Val Leu Gly His
        450                 455                 460

Arg Ala Pro Pro Cys Gly Pro Glu Phe Xaa Thr Val Val Glu Thr Gln
465                 470                 475                 480

Glu Ala Asn His Asn Ser Gly Thr Phe Leu Asp Arg Phe Thr Glu Ser
                485                 490                 495

Leu His Tyr Tyr Ser Thr Met Phe Asp Ser Leu Glu Gly Gly Ser Ser
            500                 505                 510

Gly Gly Gly Pro Ser Glu Val Ser Ser Gly Ala Ala Ala Ala Pro Ala
```

```
                515                 520                 525
Ala Ala Gly Thr Asp Gln Val Xaa Ser Glu Val Tyr Leu Gly Arg Gln
    530                 535                 540

Ile Cys Asn Val Val Ala Cys Glu Gly Ala Glu Arg Thr Xaa Arg His
545                 550                 555                 560

Glu Thr Leu Gly Gln Trp Arg Asn Arg Leu Gly Asn Ala Gly Phe Glu
                565                 570                 575

Thr Val His Leu Gly Ser Asn Ala Tyr Lys Gln Ala Xaa Thr Leu Leu
            580                 585                 590

Ala Leu Phe Ala Gly Gly Glu Arg Leu Xaa Val Glu Glu Lys Glu Gly
        595                 600                 605

Cys Leu Thr Leu Gly Leu His Thr Xaa Pro Leu Ile Ala Thr Ser Ala
    610                 615                 620

Trp Arg Leu Ala Gly Pro
625                 630

<210> SEQ ID NO 2
<211> LENGTH: 532
<212> TYPE: PRT
<213> ORGANISM: Arabidopsis thaliana

<400> SEQUENCE: 2

Met Lys Arg Asp His His His His Gln Asp Lys Lys Thr Met Met
  1               5                  10                  15

Met Asn Glu Glu Asp Asp Gly Asn Gly Met Asp Glu Leu Leu Ala Val
             20                  25                  30

Leu Gly Tyr Lys Val Arg Ser Ser Glu Met Ala Asp Val Ala Gln Lys
         35                  40                  45

Leu Glu Gln Leu Glu Val Met Met Ser Asn Val Gln Glu Asp Asp Leu
     50                  55                  60

Ser Gln Leu Ala Thr Glu Thr Val His Tyr Asn Pro Ala Glu Leu Tyr
 65                  70                  75                  80

Thr Trp Leu Asp Ser Met Leu Thr Asp Leu Asn Pro Ser Ser Asn
                 85                  90                  95

Ala Glu Tyr Asp Leu Lys Ala Ile Pro Gly Asp Ala Ile Leu Asn Gln
            100                 105                 110

Phe Ala Ile Asp Ser Ala Ser Ser Asn Gln Gly Gly Gly Asp
        115                 120                 125

Thr Tyr Thr Thr Asn Lys Arg Leu Lys Cys Ser Asn Gly Val Val Glu
    130                 135                 140

Thr Thr Thr Ala Thr Ala Glu Ser Thr Arg His Val Val Leu Val Asp
145                 150                 155                 160

Ser Gln Glu Asn Gly Val Arg Leu Val His Ala Leu Leu Ala Cys Ala
                165                 170                 175

Glu Ala Val Gln Lys Glu Asn Leu Thr Val Ala Glu Ala Leu Val Lys
            180                 185                 190

Gln Ile Gly Phe Leu Ala Val Ser Gln Ile Gly Ala Met Arg Lys Val
        195                 200                 205

Ala Thr Tyr Phe Ala Glu Ala Leu Ala Arg Arg Ile Tyr Arg Leu Ser
    210                 215                 220

Pro Ser Gln Ser Pro Ile Asp His Ser Leu Ser Asp Thr Leu Gln Met
225                 230                 235                 240

His Phe Tyr Glu Thr Cys Pro Tyr Leu Lys Phe Ala His Phe Thr Ala
                245                 250                 255
```

```
Asn Gln Ala Ile Leu Glu Ala Phe Gln Gly Lys Lys Arg Val His Val
                260                 265                 270

Ile Asp Phe Ser Met Ser Gln Gly Leu Gln Trp Pro Ala Leu Met Gln
            275                 280                 285

Ala Leu Ala Leu Arg Pro Gly Gly Pro Val Phe Arg Leu Thr Gly
        290                 295                 300

Ile Gly Pro Pro Ala Pro Asp Asn Phe Asp Tyr Leu His Glu Val Gly
305                 310                 315                 320

Cys Lys Leu Ala His Leu Ala Glu Ala Ile His Val Glu Phe Glu Tyr
                325                 330                 335

Arg Gly Phe Val Ala Asn Thr Leu Ala Asp Leu Asp Ala Ser Met Leu
            340                 345                 350

Glu Leu Arg Pro Ser Glu Ile Glu Ser Val Ala Val Asn Ser Val Phe
        355                 360                 365

Glu Leu His Lys Leu Leu Gly Arg Pro Gly Ala Ile Asp Lys Val Leu
    370                 375                 380

Gly Val Val Asn Gln Ile Lys Pro Glu Ile Phe Thr Val Val Glu Gln
385                 390                 395                 400

Glu Ser Asn His Asn Ser Pro Ile Phe Leu Asp Arg Phe Thr Glu Ser
                405                 410                 415

Leu His Tyr Tyr Ser Thr Leu Phe Asp Ser Leu Glu Gly Val Pro Ser
            420                 425                 430

Gly Gln Asp Lys Val Met Ser Glu Val Tyr Leu Gly Lys Gln Ile Cys
        435                 440                 445

Asn Val Val Ala Cys Asp Gly Pro Asp Arg Val Glu Arg His Glu Thr
    450                 455                 460

Leu Ser Gln Trp Arg Asn Arg Phe Gly Ser Ala Gly Phe Ala Ala Ala
465                 470                 475                 480

His Ile Gly Ser Asn Ala Phe Lys Gln Ala Ser Met Leu Leu Ala Leu
                485                 490                 495

Phe Asn Gly Gly Glu Gly Tyr Arg Val Glu Glu Ser Asp Gly Cys Leu
            500                 505                 510

Met Leu Gly Trp His Thr Arg Pro Leu Ile Ala Thr Ser Ala Trp Lys
        515                 520                 525

Leu Ser Thr Asn
    530

<210> SEQ ID NO 3
<211> LENGTH: 2709
<212> TYPE: DNA
<213> ORGANISM: Triticum aestivum
<220> FEATURE:
<221> NAME/KEY: misc_feature
<222> LOCATION: (6)
<223> OTHER INFORMATION: n is any nucleotide
<221> NAME/KEY: misc_feature
<222> LOCATION: (11)
<223> OTHER INFORMATION: n is any nucleotide
<221> NAME/KEY: misc_feature
<222> LOCATION: (46)
<223> OTHER INFORMATION: n is any nucleotide
<221> NAME/KEY: misc_feature
<222> LOCATION: (85)
<223> OTHER INFORMATION: n is any nucleotide
<221> NAME/KEY: misc_feature
<222> LOCATION: (107)
<223> OTHER INFORMATION: n is any nucleotide
<221> NAME/KEY: misc_feature
<222> LOCATION: (407)
<223> OTHER INFORMATION: n is any nucleotide
<221> NAME/KEY: misc_feature
```

```
<222> LOCATION: (417)
<223> OTHER INFORMATION: n is any nucleotide
<221> NAME/KEY: misc_feature
<222> LOCATION: (430)
<223> OTHER INFORMATION: n is any nucleotide
<221> NAME/KEY: misc_feature
<222> LOCATION: (436)
<223> OTHER INFORMATION: n is any nucleotide
<221> NAME/KEY: misc_feature
<222> LOCATION: (448)
<223> OTHER INFORMATION: n is any nucleotide
<221> NAME/KEY: misc_feature
<222> LOCATION: (452)
<223> OTHER INFORMATION: n is any nucleotide
<221> NAME/KEY: misc_feature
<222> LOCATION: (490)
<223> OTHER INFORMATION: n is any nucleotide
<221> NAME/KEY: misc_feature
<222> LOCATION: (498)
<223> OTHER INFORMATION: n is any nucleotide
<221> NAME/KEY: misc_feature
<222> LOCATION: (556)
<223> OTHER INFORMATION: n is any nucleotide
<221> NAME/KEY: misc_feature
<222> LOCATION: (562)
<223> OTHER INFORMATION: n is any nucleotide
<221> NAME/KEY: misc_feature
<222> LOCATION: (727)
<223> OTHER INFORMATION: n is any nucleotide
<221> NAME/KEY: misc_feature
<222> LOCATION: (769)
<223> OTHER INFORMATION: n is any nucleotide
<221> NAME/KEY: misc_feature
<222> LOCATION: (1444)
<223> OTHER INFORMATION: n is any nucleotide
<221> NAME/KEY: misc_feature
<222> LOCATION: (1450)
<223> OTHER INFORMATION: n is any nucleotide
<221> NAME/KEY: misc_feature
<222> LOCATION: (1556)
<223> OTHER INFORMATION: n is any nucleotide
<221> NAME/KEY: misc_feature
<222> LOCATION: (1742)
<223> OTHER INFORMATION: n is any nucleotide
<221> NAME/KEY: misc_feature
<222> LOCATION: (1808)
<223> OTHER INFORMATION: n is any nucleotide
<221> NAME/KEY: misc_feature
<222> LOCATION: (1900)
<223> OTHER INFORMATION: n is any nucleotide
<221> NAME/KEY: misc_feature
<222> LOCATION: (1940)
<223> OTHER INFORMATION: n is any nucleotide
<221> NAME/KEY: misc_feature
<222> LOCATION: (1982)
<223> OTHER INFORMATION: n is any nucleotide
<221> NAME/KEY: misc_feature
<222> LOCATION: (2438)
<223> OTHER INFORMATION: n is any nucleotide
<221> NAME/KEY: misc_feature
<222> LOCATION: (2604)
<223> OTHER INFORMATION: n is any nucleotide
<221> NAME/KEY: misc_feature
<222> LOCATION: (2638)
<223> OTHER INFORMATION: n is any nucleotide
<221> NAME/KEY: misc_feature
<222> LOCATION: (2681)
<223> OTHER INFORMATION: n is any nucleotide
<221> NAME/KEY: misc_feature
<222> LOCATION: (2689)
<223> OTHER INFORMATION: n is any nucleotide
<221> NAME/KEY: misc_feature
<222> LOCATION: (2706)
<223> OTHER INFORMATION: n is any nucleotide

<400> SEQUENCE: 3
tttcantttc ntccttttt  cttcttttc  caacccccgg  cccccngacc  cttggatcca    60
```

-continued

| | |
|---|---|
| aatcccgaac cgcccccag aaccnggaac cgaggccaag caaaagnttt gcgccaatta | 120 |
| ttggccagag atagatagag aggcgaggta gctcgcggat catgaagcgg gagtaccagg | 180 |
| acgccgagg gagcggcggc ggcggtggcg gcatgggttc gtccgaggac aagatgatgg | 240 |
| tgtcggcggc ggcgggggag ggggaggagg tggacgagct gctggcggcg ctcgggtaca | 300 |
| aggtgcgcgc ctccgacatg gcggacgtgg cgcagaagct ggagcagctc gagatggcca | 360 |
| tggggatggg cggcgtgggc gctggcgccg cccctgacga caggttngcc acccgcnggc | 420 |
| cgcggacacn gtgcantaca accccacnga cntgtcgtct tgggtcgaga gcatgctgtc | 480 |
| ggagctaaan gagccgcngc cgcccctccc gcccgccccg cagctcaacg cctccaccgt | 540 |
| cacgggcagc ggcggntact tngatctccc gccctcagtc gactcctcca gcagcatcta | 600 |
| cgcgctgcgg ccgatcccct ccccggccgg cgcgacggcg ccggccgacc tgtccgccga | 660 |
| ctccgtgcgg gatcccaagc ggatgcgcac tggcgggagc agcacctcgt cgtcatcctc | 720 |
| ctcatantcg tctctcggtg ggggcgccag gagctctgtg gtggaggcng ccccgccggt | 780 |
| cgcggccgcg gccaacgcga cgcccgcgct gccggtcgtc gtggtcgaca cgcaggaggc | 840 |
| cgggattcgc ctggtgcacg cgctgctggc gtgcgcggag gccgtgcagc aggagaacct | 900 |
| ctccgccgcg gaggcgctgg tgaagcagat acccttgctg gccgcgtccc agggcggcgc | 960 |
| gatgcgcaag gtcgccgcct acttcggcga ggccctcgcc cgccgcgtct tccgcttccg | 1020 |
| cccgcagccg gacagctccc tcctcgacgc cgccttcgcc gacctcctcc acgcgcactt | 1080 |
| ctacgagtcc tgcccctacc tcaagttcgc gcacttcacc gccaaccagg ccatcctgga | 1140 |
| ggcgttcgcc ggctgccgcc gcgtgcacgt cgtcgacttc ggcatcaagc aggggatgca | 1200 |
| gtggcccgca cttctccagg ccctcgccct cgtcccggc ggccctccct cgttccgcct | 1260 |
| caccggcgtc ggcccccgc agccggacga gaccgacgcc ctgcagcagg tgggctggaa | 1320 |
| gctcgcccag ttcgcgcaca ccatccgcgt cgacttccag taccgcgcc tcgtcgccgc | 1380 |
| cacgctcgcg gacctggagc cgttcatgct gcagccggag ggcgaggagg acccgaacga | 1440 |
| aganccccgan gtaatcgccg tcaactcagt cttcgagatg caccggctgc tcgcgcagcc | 1500 |
| cggcgccctg gaaaaggttc ttgggcaccg tgcgcccccg tgcggcccag aattcntcac | 1560 |
| cgtggtggaa acaggaggca aatcacaact ccggcacatt cctggaccgc ttcaccgagt | 1620 |
| ctctgcacta ctactccacc atgttcgatt ccctcgaggg cggcagctcc ggcggcggcc | 1680 |
| catccgaagt ctcatcgggg gctgctgctg ctcctgccgc cgccggcacg gaccaggtca | 1740 |
| tntccgaggt gtacctcggc cggcagatct gcaacgtggt ggcctgcgag ggggcggaac | 1800 |
| gcacagancg ccacgagacg ctgggccagt ggcggaaccg gctgggcaac gccgggttcg | 1860 |
| agaccgtcca cctgggctcc aatgcctaca agcaggcgan cacgctgctg gcgctcttcg | 1920 |
| ccggcggcga acggctacan gtggaagaaa aggaaggctg cctgacgctg gggttgcaca | 1980 |
| cnccccctg attgccacct cggcatggcg cctggccggg ccgtgatctc gcgagttttg | 2040 |
| aacgctgtaa gtacacatcg tgagcatgga ggacaacaca gccccggcgg ccgccccggc | 2100 |
| tctccggcga acgcacgcac gcacgcactt gaagaagaag aagctaaatg tcatgtcagt | 2160 |
| gagcgctgaa ttgcagcgac cggctacgat cgatcgggct acgggtggtt ccgtccgtct | 2220 |
| ggcgtgaaga ggtggatgga cgacgaactc cgagccgacc accaccggca tgtagtaatg | 2280 |
| taatcccttc ttcgttccca gttctccacc gcctccatga tcacccgtaa aactcctaag | 2340 |
| ccctattatt actactatta tgtttaaatg tctattattg ctatgtgtaa ttcctccaac | 2400 |
| cgctcatatc aaaataagca cgggccggac tttgttanca gctccaatga gaatgaaatg | 2460 |

```
aattttgtac gcaaggcacg tccaaaactg ggctgagctt tgttctgttc tgttatgttc    2520
atggtgctca ctgctctgat gaacatgatg gtgcctccaa tggtggcttt gcaattgttg    2580
aaacgtttgg cttgggggac ttgngtgggt gggtgcatgg ggatgaatat tcacatcncc    2640
ggattaaaat taagccatcc cgttggccgt cctttgaata ncttgcccna aacgaaattt    2700 ccccncatc                                                           2709
```

```
<210> SEQ ID NO 4
<211> LENGTH: 10
<212> TYPE: PRT
<213> ORGANISM: Triticum aestivum

<400> SEQUENCE: 4

Asp Val Ala Gln Lys Leu Glu Gln Leu Glu
 1               5                   10

<210> SEQ ID NO 5
<211> LENGTH: 256
<212> TYPE: PRT
<213> ORGANISM: Oryza sativa

<400> SEQUENCE: 5

Arg Pro Thr Arg Pro Glu Ala Gly Gly Ser Gly Gly Gly Ser Ser
 1               5                  10                  15

Ala Asp Met Gly Ser Cys Lys Asp Lys Val Met Ala Gly Ala Ala Gly
                20                  25                  30

Glu Glu Glu Asp Val Asp Glu Leu Leu Ala Ala Leu Gly Tyr Lys Val
            35                  40                  45

Arg Ser Ser Asp Met Ala Asp Val Ala Gln Lys Leu Glu Gln Leu Glu
        50                  55                  60

Met Ala Met Gly Met Gly Gly Val Ser Ala Pro Gly Ala Ala Asp Asp
 65                  70                  75                  80

Gly Phe Val Ser His Leu Ala Thr Asp Thr Val His Tyr Asn Pro Ser
                85                  90                  95

Asp Leu Ser Ser Trp Val Glu Ser Met Leu Ser Glu Leu Asn Ala Pro
            100                 105                 110

Leu Pro Pro Ile Pro Pro Ala Pro Pro Ala Ala Arg His Ala Ser Thr
        115                 120                 125

Ser Ser Thr Val Thr Gly Gly Gly Ser Gly Phe Phe Glu Leu Pro
130                 135                 140

Ala Ala Ala Asp Ser Ser Ser Thr Tyr Ala Leu Arg Pro Ile Ser
145                 150                 155                 160

Leu Pro Val Ala Thr Ala Asp Pro Ser Ala Asp Ser Ala Arg
                165                 170                 175

Asp Thr Lys Arg Met Arg Thr Gly Gly Gly Ser Thr Ser Ser Ser
            180                 185                 190

Ser Ser Ser Ser Leu Gly Gly Gly Ala Ser Arg Gly Ser Val Val
        195                 200                 205

Glu Ala Ala Pro Pro Ala Thr Gln Gly Ala Ala Ala Asn Ala Pro
    210                 215                 220

Ala Val Pro Val Val Val Asp Thr Gln Glu Ala Gly Ile Arg Leu
225                 230                 235                 240

Val His Ala Leu Leu Ala Cys Ala Glu Ala Val Gln Gln Glu Asn Phe
                245                 250                 255
```

```
<210> SEQ ID NO 6
<211> LENGTH: 425
<212> TYPE: PRT
<213> ORGANISM: Triticum aestivum

<400> SEQUENCE: 6

Ala Arg Ser Ser Val Val Glu Ala Pro Pro Val Ala Ala Ala
 1               5                  10                  15

Asn Ala Thr Pro Ala Leu Pro Val Val Val Asp Thr Gln Glu Ala
                20                  25                  30

Gly Ile Arg Leu Val His Ala Leu Leu Ala Cys Ala Glu Ala Val Gln
             35                  40                  45

Gln Glu Asn Leu Ser Ala Ala Glu Ala Leu Val Lys Gln Ile Pro Leu
         50                  55                  60

Leu Ala Ala Ser Gln Gly Gly Ala Met Arg Lys Val Ala Ala Tyr Phe
 65                  70                  75                  80

Gly Glu Ala Leu Ala Arg Arg Val Phe Arg Phe Arg Pro Gln Pro Asp
                 85                  90                  95

Ser Ser Leu Leu Asp Ala Ala Phe Ala Asp Leu Leu His Ala His Phe
            100                 105                 110

Tyr Glu Ser Cys Pro Tyr Leu Lys Phe Ala His Phe Thr Ala Asn Gln
        115                 120                 125

Ala Ile Leu Glu Ala Phe Ala Gly Cys Arg Arg Val His Val Val Asp
    130                 135                 140

Phe Gly Ile Lys Gln Gly Met Gln Trp Pro Ala Leu Leu Gln Ala Leu
145                 150                 155                 160

Ala Leu Arg Pro Gly Gly Pro Pro Ser Phe Arg Leu Thr Gly Val Gly
                165                 170                 175

Pro Pro Gln Pro Asp Glu Thr Asp Ala Leu Gln Gln Val Gly Trp Lys
            180                 185                 190

Leu Ala Gln Phe Ala His Thr Ile Arg Val Asp Phe Gln Tyr Arg Gly
        195                 200                 205

Leu Val Ala Ala Thr Leu Ala Asp Leu Glu Pro Phe Met Leu Gln Pro
    210                 215                 220

Glu Gly Glu Glu Asp Pro Asn Glu Glu Pro Glu Val Ile Ala Val Asn
225                 230                 235                 240

Ser Val Phe Glu Met His Arg Leu Leu Ala Gln Pro Gly Ala Leu Glu
                245                 250                 255

Lys Val Leu Gly Thr Val Arg Ala Val Arg Pro Arg Ile Val Thr Val
            260                 265                 270

Val Glu Gln Glu Ala Asn His Asn Ser Gly Thr Phe Leu Asp Arg Phe
        275                 280                 285

Thr Glu Ser Leu His Tyr Tyr Ser Thr Met Phe Asp Ser Leu Glu Gly
    290                 295                 300

Gly Ser Ser Gly Gly Pro Ser Glu Val Ser Ser Gly Ala Ala Ala
305                 310                 315                 320

Ala Pro Ala Ala Ala Gly Thr Asp Gln Val Met Ser Glu Val Tyr Leu
                325                 330                 335

Gly Arg Gln Ile Cys Asn Val Ala Cys Glu Gly Ala Glu Arg Thr
            340                 345                 350

Glu Arg His Glu Thr Leu Gly Gln Trp Arg Asn Arg Leu Gly Asn Ala
        355                 360                 365

Gly Phe Glu Thr Val His Leu Gly Ser Asn Ala Tyr Lys Gln Ala Ser
    370                 375                 380
```

```
Thr Leu Leu Ala Leu Phe Ala Gly Gly Asp Gly Tyr Lys Val Glu Glu
385                 390                 395                 400

Lys Glu Gly Cys Leu Thr Leu Gly Trp His Thr Arg Pro Leu Ile Ala
                405                 410                 415

Thr Ser Ala Trp Arg Leu Ala Gly Pro
            420                 425

<210> SEQ ID NO 7
<211> LENGTH: 623
<212> TYPE: PRT
<213> ORGANISM: Triticum aestivum

<400> SEQUENCE: 7

Met Lys Arg Glu Tyr Gln Asp Ala Gly Gly Ser Gly Gly Gly Gly Gly
1               5                   10                  15

Gly Met Gly Ser Ser Glu Asp Lys Met Met Val Ser Ala Ala Ala Gly
                20                  25                  30

Glu Gly Glu Val Asp Glu Leu Leu Ala Ala Leu Gly Tyr Lys Val
            35                  40                  45

Arg Ala Ser Asp Met Ala Asp Val Ala Gln Lys Leu Glu Gln Leu Glu
    50                  55                  60

Met Ala Met Gly Met Gly Val Gly Ala Ala Pro Asp Asp
65              70                  75                  80

Ser Phe Ala Thr His Leu Ala Thr Asp Thr Val His Tyr Asn Pro Thr
                85                  90                  95

Asp Leu Ser Ser Trp Val Glu Ser Met Leu Ser Glu Leu Asn Ala Pro
                100                 105                 110

Pro Pro Pro Leu Pro Pro Ala Pro Gln Leu Asn Ala Ser Thr Ser Ser
            115                 120                 125

Thr Val Thr Gly Ser Gly Gly Tyr Phe Asp Leu Pro Pro Ser Val Asp
130                 135                 140

Ser Ser Ser Ser Ile Tyr Ala Leu Arg Pro Ile Pro Ser Pro Ala Gly
145                 150                 155                 160

Ala Thr Ala Pro Ala Asp Leu Ser Ala Asp Ser Val Arg Asp Pro Lys
                165                 170                 175

Arg Met Arg Thr Gly Gly Ser Ser Thr Ser Ser Ser Ser Ser Ser Ser
            180                 185                 190

Ser Ser Leu Gly Gly Gly Ala Arg Ser Ser Val Val Glu Ala Ala Pro
        195                 200                 205

Pro Val Ala Ala Ala Ala Asn Ala Thr Pro Ala Leu Pro Val Val Val
    210                 215                 220

Val Asp Thr Gln Glu Ala Gly Ile Arg Leu Val His Ala Leu Leu Ala
225                 230                 235                 240

Cys Ala Glu Ala Val Gln Gln Glu Asn Leu Ser Ala Ala Glu Ala Leu
                245                 250                 255

Val Lys Gln Ile Pro Leu Leu Ala Ala Ser Gln Gly Gly Ala Met Arg
                260                 265                 270

Lys Val Ala Ala Tyr Phe Gly Glu Ala Leu Ala Arg Arg Val Phe Arg
            275                 280                 285

Phe Arg Pro Gln Pro Asp Ser Ser Leu Leu Asp Ala Ala Phe Ala Asp
        290                 295                 300

Leu Leu His Ala His Phe Tyr Glu Ser Cys Pro Tyr Leu Lys Phe Ala
305                 310                 315                 320

His Phe Thr Ala Asn Gln Ala Ile Leu Glu Ala Phe Ala Gly Cys Arg
                325                 330                 335
```

-continued

Arg Val His Val Asp Phe Gly Ile Lys Gln Gly Met Gln Trp Pro
        340             345             350

Ala Leu Leu Gln Ala Leu Ala Leu Arg Pro Gly Gly Pro Pro Ser Phe
            355             360             365

Arg Leu Thr Gly Val Gly Pro Pro Gln Pro Asp Glu Thr Asp Ala Leu
        370             375             380

Gln Gln Val Gly Trp Lys Leu Ala Gln Phe Ala His Thr Ile Arg Val
385             390             395             400

Asp Phe Gln Tyr Arg Gly Leu Val Ala Ala Thr Leu Ala Asp Leu Glu
            405             410             415

Pro Phe Met Leu Gln Pro Glu Gly Glu Glu Asp Pro Asn Glu Glu Pro
            420             425             430

Glu Val Ile Ala Val Asn Ser Val Phe Glu Met His Arg Leu Leu Ala
            435             440             445

Gln Pro Gly Ala Leu Glu Lys Val Leu Gly Thr Val Arg Ala Val Arg
        450             455             460

Pro Arg Ile Val Thr Val Val Glu Gln Glu Ala Asn His Asn Ser Gly
465             470             475             480

Thr Phe Leu Asp Arg Phe Thr Glu Ser Leu His Tyr Tyr Ser Thr Met
            485             490             495

Phe Asp Ser Leu Glu Gly Gly Ser Ser Gly Gly Pro Ser Glu Val
            500             505             510

Ser Ser Gly Ala Ala Ala Ala Pro Ala Ala Ala Gly Thr Asp Gln Val
            515             520             525

Met Ser Glu Val Tyr Leu Gly Arg Gln Ile Cys Asn Val Val Ala Cys
        530             535             540

Glu Gly Ala Glu Arg Thr Glu Arg His Glu Thr Leu Gly Gln Trp Arg
545             550             555             560

Asn Arg Leu Gly Asn Ala Gly Phe Glu Thr Val His Leu Gly Ser Asn
            565             570             575

Ala Tyr Lys Gln Ala Ser Thr Leu Leu Ala Leu Phe Ala Gly Gly Asp
            580             585             590

Gly Tyr Lys Val Glu Glu Lys Glu Gly Cys Leu Thr Leu Gly Trp His
        595             600             605

Thr Arg Pro Leu Ile Ala Thr Ser Ala Trp Arg Leu Ala Gly Pro
        610             615             620

<210> SEQ ID NO 8
<211> LENGTH: 630
<212> TYPE: PRT
<213> ORGANISM: Zea mays

<400> SEQUENCE: 8

Met Lys Arg Glu Tyr Gln Asp Ala Gly Gly Ser Gly Gly Asp Met Gly
1               5               10              15

Ser Ser Lys Asp Lys Met Met Ala Ala Ala Gly Ala Gly Glu Gln
            20              25              30

Glu Glu Glu Asp Val Asp Glu Leu Leu Ala Ala Leu Gly Tyr Lys Val
            35              40              45

Arg Ser Ser Asp Met Ala Asp Val Ala Gln Lys Leu Glu Gln Leu Glu
        50              55              60

Met Ala Met Gly Met Gly Gly Val Gly Gly Ala Gly Ala Thr Ala Asp
65              70              75              80

Asp Gly Phe Val Ser His Leu Ala Thr Asp Thr Val His Tyr Asn Pro

-continued

```
                85                  90                  95
Ser Asp Leu Ser Ser Trp Val Glu Ser Met Leu Ser Glu Leu Asn Ala
            100                 105                 110
Pro Pro Ala Pro Leu Pro Pro Ala Thr Pro Ala Pro Arg Leu Ala Ser
        115                 120                 125
Thr Ser Thr Val Thr Ser Gly Ala Ala Gly Ala Gly Tyr Phe
    130                 135                 140
Asp Leu Pro Pro Ala Val Asp Ser Ser Ser Thr Tyr Ala Leu Lys
145                 150                 155                 160
Pro Ile Pro Ser Pro Val Ala Ala Pro Ser Ala Asp Pro Ser Thr Asp
                165                 170                 175
Ser Ala Arg Glu Pro Lys Arg Met Arg Thr Gly Gly Ser Thr Ser
            180                 185                 190
Ser Ser Ser Ser Ser Ser Ser Met Asp Gly Gly Arg Thr Arg Ser
        195                 200                 205
Ser Val Val Glu Ala Ala Pro Ala Thr Gln Ala Ser Ala Ala Ala
    210                 215                 220
Asn Gly Pro Ala Val Pro Val Val Val Asp Thr Gln Glu Ala Gly
225                 230                 235                 240
Ile Arg Leu Val His Ala Leu Leu Ala Cys Ala Glu Ala Val Gln Gln
                245                 250                 255
Glu Asn Phe Ser Ala Ala Glu Ala Leu Val Lys Gln Ile Pro Met Leu
            260                 265                 270
Ala Ser Ser Gln Gly Gly Ala Met Arg Lys Val Ala Ala Tyr Phe Gly
        275                 280                 285
Glu Ala Leu Ala Arg Arg Val Tyr Arg Phe Arg Pro Pro Asp Ser
    290                 295                 300
Ser Leu Leu Asp Ala Ala Phe Ala Asp Leu Leu His Ala His Phe Tyr
305                 310                 315                 320
Glu Ser Cys Pro Tyr Leu Lys Phe Ala His Phe Thr Ala Asn Gln Ala
                325                 330                 335
Ile Leu Glu Ala Phe Ala Gly Cys Arg Arg Val His Val Val Asp Phe
            340                 345                 350
Gly Ile Lys Gln Gly Met Gln Trp Pro Ala Leu Leu Gln Ala Leu Ala
        355                 360                 365
Leu Arg Pro Gly Gly Pro Pro Ser Phe Arg Leu Thr Gly Val Gly Pro
    370                 375                 380
Pro Gln Pro Asp Glu Thr Asp Ala Leu Gln Gln Val Gly Trp Lys Leu
385                 390                 395                 400
Ala Gln Phe Ala His Thr Ile Arg Val Asp Phe Gln Tyr Arg Gly Leu
                405                 410                 415
Val Ala Ala Thr Leu Ala Asp Leu Glu Pro Phe Met Leu Gln Pro Glu
            420                 425                 430
Gly Asp Asp Thr Asp Asp Glu Pro Glu Val Ile Ala Val Asn Ser Val
        435                 440                 445
Phe Glu Leu His Arg Leu Leu Ala Gln Pro Gly Ala Leu Glu Lys Val
    450                 455                 460
Leu Gly Thr Val Arg Ala Val Arg Pro Arg Ile Val Thr Val Val Glu
465                 470                 475                 480
Gln Glu Ala Asn His Asn Ser Gly Thr Phe Leu Asp Arg Phe Thr Glu
                485                 490                 495
Ser Leu His Tyr Tyr Ser Thr Met Phe Asp Ser Leu Glu Gly Ala Gly
            500                 505                 510
```

```
Ala Gly Ser Gly Gln Ser Thr Asp Ala Ser Pro Ala Ala Gly Gly
            515                 520                 525

Thr Asp Gln Val Met Ser Glu Val Tyr Leu Gly Arg Gln Ile Cys Asn
        530                 535                 540

Val Val Ala Cys Glu Gly Ala Glu Arg Thr Glu Arg His Glu Thr Leu
545                 550                 555                 560

Gly Gln Trp Arg Ser Arg Leu Gly Gly Ser Gly Phe Ala Pro Val His
                565                 570                 575

Leu Gly Ser Asn Ala Tyr Lys Gln Ala Ser Thr Leu Leu Ala Leu Phe
            580                 585                 590

Ala Gly Gly Asp Gly Tyr Arg Val Glu Glu Lys Asp Gly Cys Leu Thr
        595                 600                 605

Leu Gly Trp His Thr Arg Pro Leu Ile Ala Thr Ser Ala Trp Arg Val
    610                 615                 620

Ala Ala Ala Ala Ala Pro
625                 630

<210> SEQ ID NO 9
<211> LENGTH: 100
<212> TYPE: PRT
<213> ORGANISM: Zea mays

<400> SEQUENCE: 9

Tyr Gln Asp Ala Gly Gly Ser Gly Gly Asp Met Gly Ser Ser Lys Asp
  1               5                  10                  15

Lys Met Met Ala Ala Ala Gly Ala Gly Glu Gln Glu Glu Glu Glu Asp
                20                  25                  30

Val Asp Glu Leu Leu Ala Ala Leu Gly Tyr Lys Val Arg Ser Ser Asp
            35                  40                  45

Met Ala Gly Leu Glu Gln Leu Glu Met Ala Met Gly Met Gly Gly Val
        50                  55                  60

Gly Gly Ala Gly Ala Thr Ala Asp Asp Gly Phe Val Ser His Leu Ala
65                  70                  75                  80

Thr Asp Thr Val His Tyr Asn Pro Ser Asp Leu Ser Ser Trp Val Glu
                85                  90                  95

Ser Met Leu Ser
            100

<210> SEQ ID NO 10
<211> LENGTH: 123
<212> TYPE: PRT
<213> ORGANISM: Zea mays

<400> SEQUENCE: 10

Ser Ser Lys Asp Lys Met Met Ala Ala Ala Gly Ala Gly Glu Gln
  1               5                  10                  15

Glu Glu Glu Asp Val Asp Glu Leu Leu Ala Ala Leu Gly Tyr Lys Val
                20                  25                  30

Arg Ser Ser Asp Met Ala Asp Val Ala Gln Lys Leu Glu Gln Leu Glu
            35                  40                  45

Met Ala Met Gly Met Gly Gly Val Gly Ala Gly Ala Thr Ala Asp
        50                  55                  60

Asp Gly Phe Val Ser His Leu Ser Ser Trp Val Glu Ser Met Leu Ser
65                  70                  75                  80

Glu Leu Asn Ala Pro Pro Ala Pro Leu Pro Ala Thr Pro Ala Pro
                85                  90                  95
```

-continued

Arg Leu Ala Ser Thr Ser Ser Thr Val Thr Ser Gly Ala Ala Ala Gly
              100                 105                 110

Ala Gly Tyr Phe Asp Leu Pro Pro Ala Val Asp
        115                 120

<210> SEQ ID NO 11
<211> LENGTH: 138
<212> TYPE: PRT
<213> ORGANISM: Triticum aestivum

<400> SEQUENCE: 11

Ala Ala Leu Gly Tyr Lys Val Arg Ala Ser Asp Met Ala Asp Val Ala
 1               5                  10                  15

Gln Lys Leu Glu Gln Leu Glu Met Ala Met Gly Met Gly Gly Val Gly
            20                  25                  30

Ala Gly Ala Ala Pro Asp Asp Ser Phe Ala Thr His Leu Ala Thr Asp
        35                  40                  45

Thr Val His Tyr Asn Pro Thr Asp Leu Ser Ser Trp Val Glu Ser Met
    50                  55                  60

Leu Ser Glu Leu Asn Ala Ser Thr Ser Ser Thr Val Thr Gly Ser Gly
65                  70                  75                  80

Gly Tyr Phe Asp Leu Pro Pro Ser Val Asp Ser Ser Ser Ile Tyr
                85                  90                  95

Ala Leu Arg Pro Ile Pro Ser Pro Ala Gly Ala Thr Ala Pro Ala Asp
            100                 105                 110

Leu Ser Ala Asp Ser Val Arg Asp Pro Lys Arg Met Arg Thr Gly Gly
        115                 120                 125

Ser Ser Thr Ser Ser Ser Ser Ser Ser
    130                 135

<210> SEQ ID NO 12
<211> LENGTH: 770
<212> TYPE: DNA
<213> ORGANISM: Oryza sativa

<400> SEQUENCE: 12
gtcgacccac gcgtccggaa gccggcggga gcagcggcgg cgggagcagc gccgatatgg      60
ggtcgtgcaa ggacaaggtg atggcggggg cggcggggga ggaggaggac gtcgacgagc     120
tgctggcggc gctcgggtac aaggtgcggt cgtccgacat ggccgacgtc gcgcagaagc     180
tggagcagct ggagatggcc atggggatgg gcggcgtgag cgcccccggc gccgcggatg     240
acgggttcgt gtcgcacctg ccacggacac ccgtgcacta caaccccctcg gacctctcct     300
cctgggtcga gagcatgctt tccgagctca acgccgcgct gccccctatc cgccagcgc     360
cgccggctgc cgccatgctc tccacctcgt ccactgtcac cggcggcggt ggtagcggct     420
tctttgaact cccagccgct gccgactcgt cgagtagcac ctacgccctc aggccgatct     480
ccttaccggt ggtggcgacg gctgacccgt cggctgctga ctcggcgagg gacaccaagc     540
ggatgcgcac tggcggcggc agcacgtcgt cgtcctcatc gtcgtcttcc tctctgggcg     600
gtggggcctc gcggggctct gtggtggagg ctgctccgcc ggcgacgcaa ggggccgcgg     660
cggcgaatgc gcccgccgtg ccggttgtgg tggttgacac gcaggaggct gggatccggc     720
tggtgcacgc gttgctggcg tgcgcggagg ccgtgcagca ggagaacttc                 770

<210> SEQ ID NO 13
<211> LENGTH: 1768

```
<212> TYPE: DNA
<213> ORGANISM: Triticum aestivum

<400> SEQUENCE: 13
gccaggagct ctgtggtgga ggctgccccg ccggtcgcgg ccgcggccaa cgcgacgccc      60
gcgctgccgg tcgtcgtggt cgacacgcag gaggccggga ttcggctggt gcacgcgctg     120
ctggcgtgcg cggaggccgt gcagcaggag aacctctccg ccgcggaggc gctggtgaag     180
cagataccct tgctggccgc gtcccagggc ggcgcgatgc gcaaggtcgc cgcctacttc     240
ggcgaggccc tcgcccgccg cgtcttccgc ttccgcccgc agccggacag ctccctcctc     300
gacgccgcct tcgccgacct cctccacgcg cacttctacg agtcctgccc ctacctcaag     360
ttcgcgcact tcaccgccaa ccaggccatc ctggaggcgt cgccggctg ccgccgcgtg      420
cacgtcgtcg acttcggcat caagcagggg atgcagtggc ccgcacttct ccaggccctc     480
gccctccgtc ccggcggccc tccctcgttc cgcctcaccg gcgtcggccc ccgcagccg      540
gacgagaccg acgccctgca gcaggtgggc tggaagctcg cccagttcgc gcacaccatc     600
cgcgtcgact ccagtaccg cggcctcgtc gccgccacgc tcgcggacct ggagccgttc      660
atgctgcagc cggagggcga ggaggacccg aacgaggagc ccgaggtaat cgccgtcaac     720
tcagtcttcg agatgcaccg gctgctcgcg cagcccggcg ccctggagaa ggtcctgggc     780
accgtgcgcg ccgtgcggcc caggatcgtc accgtggtgg agcaggaggc gaatcacaac     840
tccggcacat tcctgaccg cttcaccgag tctctgcact actactccac catgttcgat      900
tccctcgagg gcggcagctc cggcggcggc ccatccgaag tctcatcggg ggctgctgct     960
gctcctgccg ccgccggcac ggaccaggtc atgtccgagg tgtacctcgg ccggcagatc    1020
tgcaacgtgg tggcctgcga gggggcggag cgcacagagc gccacgagac gctgggccag    1080
tggcggaacc ggctgggcaa cgccgggttc gagaccgtcc acctgggctc caatgcctac    1140
aagcaggcga gcacgctgct ggcgctcttc gccggcggcg acggctacaa ggtggaggag    1200
aaggaaggct gcctgacgct ggggtggcac acgcgcccgc tgatcgccac ctcggcatgg    1260
cgcctggccg ggccgtgatc tcgcgagttt tgaacgctgt aagtacacat cgtgagcatg    1320
gaggacaaca cagccccggc ggccgccccg gctctccggc gaacgcacgc acgcacgcac    1380
ttgaagaaga agaagctaaa tgtcatgtca gtgagcgctg aattgcagcg accggctacg    1440
atcgatcggg ctacgggtgg ttccgtccgt ctggcgtgaa gaggtggatg gacgacgaac    1500
tccgagccga ccaccaccgg catgtagtaa tgtaatccct tcttcgttcc cagttctcca    1560
ccgcctccat gatcacccgt aaaactccta agccctatta ttactactat tatgtttaaa    1620
tgtctattat tgctatgtgt aattcctcca accgctcata tcaaaataag cacgggccgg    1680
aaaaaaaaaa aaaaaaaaaa aaaaaaaaaa aaaaaaaaaa aaaaaaaaaa aaaaaaaaaa    1740
aaaaaaaaaa aaaaaaaaaa aaaaaaaa                                      1768

<210> SEQ ID NO 14
<211> LENGTH: 2125
<212> TYPE: DNA
<213> ORGANISM: Triticum aestivum

<400> SEQUENCE: 14
atagagaggc gaggtagctc gcggatcatg aagcgggagt accaggacgc cggagggagc      60
ggcggcggcg gtggcggcat gggctcgtcc gaggacaaga tgatggtgtc ggcggcggcg     120
ggggaggggg aggaggtgga cgagctgctg cggcgctcg gtacaaggt gcgcgcctcc      180
```

-continued

```
gacatggcgg acgtggcgca gaagctggag cagctcgaga tggccatggg gatgggcggc      240
gtgggcgccg gcgccgcccc cgacgacagc ttcgccaccc acctcgccac ggacaccgtg      300
cactacaacc ccaccgacct gtcgtcttgg gtcgagagca tgctgtcgga gctcaacgcg      360
ccgccgccgc ccctcccgcc cgccccgcag ctcaacgcct ccacctcctc caccgtcacg      420
ggcagcggcg gctacttcga tctcccgccc tccgtcgact cctccagcag catctacgcg      480
ctgcggccga tccctccc ggccggcgcg acggcgccgg ccgacctgtc cgccgactcc      540
gtgcgggatc ccaagcggat gcgcactggc gggagcagca cctcgtcgtc atcctcctcc      600
tcgtcgtctc tcggtggggg cgccaggagc tctgtggtgg aggctgcccc gccggtcgcg      660
gccgcggcca acgcgacgcc cgcgctgccg gtcgtcgtgg tcgacacgca ggaggccggg      720
attcggctgg tgcacgcgct gctggcgtgc gcggaggccg tgcagcagga gaacctctcc      780
gccgcggagg cgctggtgaa gcagataccc ttgctggccg cgtcccaggg cggcgcgatg      840
cgcaaggtcg ccgcctactt cggcgaggcc ctcgcccgcc gcgtcttccg cttccgcccg      900
cagccggaca gctccctcct cgacgccgcc ttcgccgacc tcctccacgc gcacttctac      960
gagtcctgcc cctacctcaa gttcgcgcac ttcaccgcca accaggccat cctggaggcg     1020
ttcgccggct gccgccgcgt gcacgtcgtc gacttcggca tcaagcaggg gatgcagtgg     1080
cccgcacttc tccaggccct cgccctccgt cccggcggcc ctccctcgtt ccgcctcacc     1140
ggcgtcggcc cccgcagcc ggacgagacc gacgccctgc agcaggtggg ctggaagctc     1200
gcccagttcg cgcacaccat ccgcgtcgac ttccagtacc gcggcctcgt cgccgccacg     1260
ctcgcggacc tggagccgtt catgctgcag ccggagggcg aggaagaccc gaacgaggag     1320
cccgaggtaa tcgccgtcaa ctcagtcttc gagatgcacc ggctgctcgc gcagcccggc     1380
gccctggaga aggtcctggg caccgtgcgc gccgtgcggc ccaggatcgt caccgtggtg     1440
gagcaggagg cgaatcacaa ctccggcaca ttcctggacc gcttcaccga gtctctgcac     1500
tactactcca ccatgttcga ttccctcgag ggcggcagct ccggcggcgg cccatccgaa     1560
gtctcatcgg gggctgctgc tgctcctgcc gccgccggca cggaccaggt catgtccgag     1620
gtgtacctcg gccggcagat ctgcaacgtg gtggcctgcg aggggcgga gcgcacagag     1680 cgccacgaga cgctgggcca gtggcggaac cggctgggca acgccgggtt cgagaccgtc     1740
cacctgggct ccaatgccta caagcaggcg agcacgctgc tggcgctctt cgccggcggc     1800
gacggctaca aggtggagga gaaggaaggc tgcctgacgc tggggtggca cacgcgcccg     1860
ctgatcgcca cctcggcatg gcgcctggcc gggccgtgat ctcgcgagtt ttgaacgctg     1920
taagtacaca tcgtgagcat ggaggacaac acagccccgg cggccgcccc ggctctccgg     1980
cgaacgcacg cacgcacgca cttgaagaag aagaagctaa atgtcatgtc agtgagcgct     2040
gaattgcagc gaccggctac gatcgatcgg gctacgggtg gttccgtccg tctggcgtga     2100
agaggtggat ggacgacgaa ctccg                                           2125
```

<210> SEQ ID NO 15
<211> LENGTH: 2255
<212> TYPE: DNA
<213> ORGANISM: Zea mays

<400> SEQUENCE: 15

```
tttcgcctgc cgctgctatt aataattgcc ttcttggttt ccccgttttc gccccagccg       60
cttcccccct cccctaccct ttccttcccc actcgcactt cccaaccctg gatccaaatc      120
ccaagctatc ccagaaccga aaccgaggcg cgcaagccat tattagctgg ctagctaggc      180
```

-continued

```
ctgtagctcc gaaatcatga agcgcgagta ccaagacgcc ggcgggagtg gcggcgacat      240
gggctcctcc aaggacaaga tgatggcggc ggcggcggga gcaggggaac aggaggagga      300
ggacgtggat gagctgctgg ccgcgctcgg gtacaaggtg cgttcgtcgg atatggcgga      360
cgtcgcgcag aagctggagc agctcgagat ggccatgggg atgggcggcg tgggcggcgc      420
cggcgctacc gctgatgacg ggttcgtgtc gcacctcgcc acggacaccg tgcactacaa      480
tccctccgac ctgtcgtcct gggtcgagag catgctgtcc gagctcaacg cgccccagc      540 gccgctcccg cccgcgacgc cggccccaag gctcgcgtcc acatcgtcca ccgtcacaag      600
tggcgccgcc gccggtgctg gctacttcga tctcccgccc gccgtggact cgtccagcag      660
tacctacgct ctgaagccga tcccctcgcc ggtggcggcg ccgtcggccg acccgtccac      720
ggactcggcg cgggagccca gcggatgag gactggcggg ggcagcacgt cgtcctcctc      780
ttcctcgtcg tcatccatgg atggcggtcg cactaggagc tccgtggtcg aagctgcgcc      840
gccggcgacg caagcatccg cggcggccaa cgggcccgcg gtgccggtgg tggtggtgga      900
cacgcaggag gccgggatcc ggctcgtgca cgcgctgctg gcgtgcgcgg aggccgtgca      960
gcaggagaac ttctctgcgg cggaggcgct ggtcaagcag atccccatgc tggcctcgtc     1020
gcagggcggt gccatgcgca aggtcgccgc ctacttcggc gaggcgcttg cccgccgcgt     1080
gtatcgcttc cgcccgccac cggacagctc cctcctcgac gccgcttcg ccgacctctt     1140 gcacgcgcac ttctacgagt cctgccccta cctgaagttc gcccacttca ccgcgaacca     1200
ggccatcctc gaggccttcg ccggctgccg ccgcgtccac gtcgtcgact tcggcatcaa     1260
gcaggggatg cagtggccgg ctcttctcca ggccctcgcc ctccgccctg gcggcccccc     1320
gtcgttccgg ctcaccggcg tcgggccgcc gcagcccgac gagaccgacg ccttgcagca     1380
ggtgggctgg aaacttgccc agttcgcgca caccatccgc gtggacttcc agtaccgtgg     1440
cctcgtcgcg gccacgctcg ccgacctgga gccgttcatg ctgcaaccgg agggcgatga     1500
cacggatgac gagcccgagg tgatcgccgt gaactccgtg ttcgagctgc accggcttct     1560
tgcgcagccc ggtgccctcg agaaggtcct gggcacggtg cgcgcggtgc ggccgaggat     1620
cgtgaccgtg gtcgagcagg aggccaacca caactccggc acgttcctcg accgcttcac     1680
cgagtcgctg cactactact ccaccatgtt cgattctctc gagggcgccg cgccggctc      1740 cggccagtcc accgacgcct cccgggccgc ggccggcggc acggaccagg tcatgtcgga     1800
ggtgtacctc ggccggcaga tctgcaacgt ggtggcgtgc gagggcgcgg agcgcacgga     1860
gcgccacgag acgctgggcc agtggcgcag ccgcctcggc ggctccgggt tcgcgcccgt     1920
gcacctgggc tccaatgcct acaagcaggc gagcacgctg ctggcgctct tcgcggcgg     1980 cgacgggtac agggtggagg agaaggacgg gtgcctgacc ctggggtggc atacgcgccc     2040
gctcatcgcc acctcggcgt ggcgcgtcgc cgccgccgcc gctccgtgat cagggagggg     2100 tggttgggc ttctggacgc cgatcaaggc acacgtacgt cccctggcat ggcgcaccct     2160
ccctcgagct cgccggcacg ggtgaagcta cccgggggat ccactaattc taaaacggcc     2220
ccaccgcggt ggaactccac cttttgttcc cttta                                2255
```

<210> SEQ ID NO 16
<211> LENGTH: 302
<212> TYPE: DNA
<213> ORGANISM: Zea mays

<400> SEQUENCE: 16

```
taccaagacg ccggcgggag tggcggcgac atgggctcct ccaaggacaa gatgatggcg      60
gcggcggcgg gagcagggga acaggaggag gaggacgtgg atgagctgct ggccgcgctc     120
gggtacaagg tgcgttcgtc ggatatggcg gggctggagc agctcgagat ggccatgggg     180
atgggcggcg tgggcggcgc cggcgctacc gctgatgacg ggttcgtgtc gcacctcgcc     240
acggacaccg tgcactacaa tccctccgac ctgtcgtcct gggtcgagag catgctgtcc     300
ga                                                                    302
```

<210> SEQ ID NO 17
<211> LENGTH: 371
<212> TYPE: DNA
<213> ORGANISM: Zea mays

<400> SEQUENCE: 17

```
tcctccaagg acaagatgat ggcggcggcg gcgggagcag gggaacagga ggaggaggac      60
gtggatgagc tgctggccgc gctcgggtac aaggtgcgtt cgtcggatat ggcggacgtc     120
gcgcagaagc tggagcagct cgagatggcc atggggatgg gcggcgtggg cggcgccggc     180
gctaccgctg atgacgggtt cgtgtcgcac ctgtcgtcct gggtcgagag catgctgtcc     240
gagctcaacg cgcccccagc gccgctcccg cccgcgacgc cggccccaag gctcgcgtcc     300
acatcgtcca ccgtcacaag tggcgccgcc gccggtgctg gctacttcga tctcccgccc     360
gccgtggact c                                                          371
```

<210> SEQ ID NO 18
<211> LENGTH: 416
<212> TYPE: DNA
<213> ORGANISM: Triticum aestivum

<400> SEQUENCE: 18

```
gcggcgctcg ggtacaaggt gcgcgcctcc gacatggcgg acgtggcgca gaagctggag      60
cagctcgaga tggccatggg gatgggcggc gtgggcgccg gcgccgcccc cgacgacagc     120
ttcgccaccc acctcgccac ggacaccgtg cactacaacc ccaccgacct gtcgtcttgg     180
gtcgagagca tgctgtcgga gctcaacgcc tccacctcct ccaccgtcac gggcagcggc     240
ggctacttcg atctcccgcc ctccgtcgac tcctccagca gcatctacgc gctgcggccg     300
atcccctccc cggccggcgc gacggcgccg gcgacctgt ccgccgactc cgtgcgggat     360
cccaagcgga tgcgcactgg cgggagcagc acctcgtcgt catcctcctc ctcgtc         416
```

<210> SEQ ID NO 19
<211> LENGTH: 725
<212> TYPE: DNA
<213> ORGANISM: Oryza sativa
<220> FEATURE:
<221> NAME/KEY: misc_feature
<222> LOCATION: (171)
<223> OTHER INFORMATION: n is any nucleotide
<221> NAME/KEY: misc_feature
<222> LOCATION: (302)
<223> OTHER INFORMATION: n is any nucleotide
<221> NAME/KEY: misc_feature
<222> LOCATION: (427)
<223> OTHER INFORMATION: n is any nucleotide
<221> NAME/KEY: misc_feature
<222> LOCATION: (444)
<223> OTHER INFORMATION: n is any nucleotide
<221> NAME/KEY: misc_feature
<222> LOCATION: (459)
<223> OTHER INFORMATION: n is any nucleotide
<221> NAME/KEY: misc_feature
<222> LOCATION: (711)

-continued

<223> OTHER INFORMATION: n is any nucleotide

<400> SEQUENCE: 19

```
acgcgtccgg aagccggcgg gagcagcggc ggcgggagca gcgccgatat gggtcgtgc      60
aaggacaagg tgatggcggg ggcggcgggg gaggaggagg acgtctacga gctgctggcg    120
gcgctcgggt acaaggtgcg gtcgtccgac atggccgacg tcgcgcagaa nctggagcag    180
ctggagatgg ccatggggat gggcggcgtg agcgccccg gcgccgcgga tgacgggttc     240
gtgtcgcacc tggccacgga caccgtgcac tacaacccct cggacctctc ctcctgggtt    300
cngagagcat gctttcggag ttaaaggcgc cgttgccct tatcccgcca ggcgccgccg     360
ggctgcccgc catgctttcc aacttcgtcc actgtcaccg gcggcggtgg tagcggcttc    420
tttgaantcc cagccgctgc cgantcgtcg agtagcacnt acgccctcag gccgatctcc    480
ttaccggtgg tggcgacggc tgacccgtcg gctgctgact cggcgaggga caccaagcgg    540
atgcgcactg gcgccggcag cacgtcgtcg tcctcatcgt cgtcttcctc tctgggcggt    600
gggcctcgc ggggctctgt ggtggaggct gctccgccgg cgacgcaagg ggccgcggcg     660
gcgaatgcgc ccgccgtgcc ggttgtggtg gttgacacgc aggaggctgg natcgggcct    720
ggtgc                                                                725
```

<210> SEQ ID NO 20
<211> LENGTH: 258
<212> TYPE: PRT
<213> ORGANISM: Oryza sativa
<220> FEATURE:
<221> NAME/KEY: SITE
<222> LOCATION: (57)
<223> OTHER INFORMATION: Xaa is unknown or other amino acid
<221> NAME/KEY: SITE
<222> LOCATION: (143)
<223> OTHER INFORMATION: Xaa is unknown or other amino acid
<221> NAME/KEY: SITE
<222> LOCATION: (148)
<223> OTHER INFORMATION: Xaa is unknown or other amino acid
<221> NAME/KEY: SITE
<222> LOCATION: (250)
<223> OTHER INFORMATION: Xaa is unknown or other amino acid

<400> SEQUENCE: 20

```
Thr Arg Pro Glu Ala Gly Gly Ser Ser Gly Gly Gly Ser Ser Ala Asp
  1               5                  10                  15

Met Gly Ser Cys Lys Asp Lys Val Met Ala Gly Ala Ala Gly Glu Glu
                 20                  25                  30

Glu Asp Val Asp Glu Leu Leu Ala Ala Leu Gly Tyr Lys Val Arg Ser
             35                  40                  45

Ser Asp Met Ala Asp Val Ala Gln Xaa Leu Glu Gln Leu Glu Met Ala
         50                  55                  60

Met Gly Met Gly Gly Val Ser Ala Pro Gly Ala Ala Asp Asp Gly Phe
 65                  70                  75                  80

Val Ser His Leu Ala Thr Asp Thr Val His Tyr Asn Pro Ser Asp Leu
                 85                  90                  95

Ser Ser Trp Val Glu Ser Met Leu Ser Glu Leu Lys Ala Pro Leu Pro
            100                 105                 110

Leu Ile Pro Pro Gly Ala Ala Gly Leu Pro Ala Met Leu Ser Pro Thr
        115                 120                 125

Ser Ser Thr Val Thr Gly Gly Gly Ser Gly Phe Phe Glu Xaa Pro
    130                 135                 140

Ala Ala Ala Xaa Ser Ser Ser Ser Thr Tyr Ala Leu Arg Pro Ile Ser
```

```
145                 150                 155                 160
Leu Pro Val Val Ala Thr Ala Asp Pro Ser Ala Ala Asp Ser Ala Arg
                165                 170                 175
Asp Thr Lys Arg Met Arg Thr Gly Gly Gly Ser Thr Ser Ser Ser Ser
            180                 185                 190
Ser Ser Ser Ser Ser Leu Gly Gly Gly Ala Ser Arg Gly Ser Val Val
            195                 200                 205
Glu Ala Ala Pro Pro Ala Thr Gln Gly Ala Ala Ala Asn Ala Pro
        210                 215                 220
Ala Val Pro Val Val Val Asp Thr Gln Glu Glu Glu Ala Gly Ile
225                 230                 235                 240
Arg Leu Val His Ala Leu Leu Ala Cys Xaa Glu Ala Val Gln Gln Glu
                245                 250                 255
Asn Phe

<210> SEQ ID NO 21
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 21
tttgcgccaa ttattggcca gagatagata gagag                        35

<210> SEQ ID NO 22
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 22
gtggcggcat gggttcgtcc gaggacaaga tgatg                        35

<210> SEQ ID NO 23
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 23
catggaggcg gtggagaact gggaacgaag aaggg                        35

<210> SEQ ID NO 24
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 24
cccggccagg cgccatgccg aggtggcaat caggg                        35

<210> SEQ ID NO 25
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 25
```
ggtatctgct tcaccagcgc ctccgcggcg gagag                                    35

<210> SEQ ID NO 26
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 26
atcggccgca gcgcgtagat gctgctggag gagtc                                    35

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 27
ctggtgaagc agatacccct gc                                                  22

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 28
ctggttggcg gtgaagtgcg                                                     20

<210> SEQ ID NO 29
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 29
gcaagggtat ctgcttcacc agc                                                 23

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 30
cgcacttcac cgccaaccag                                                     20

<210> SEQ ID NO 31
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 31
ttgtgatttg cctcctgttt cc                                                  22

<210> SEQ ID NO 32
<211> LENGTH: 23
<212> TYPE: DNA

```
<213> ORGANISM: Artificial Sequence
<220> FEATURE:
<223> OTHER INFORMATION: Description of Artificial Sequence: Primer

<400> SEQUENCE: 32
ccgtgcgccc ccgtgcggcc cag                                              23

<210> SEQ ID NO 33
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 33
aggctgcctg acgctggggt tgc                                              23

<210> SEQ ID NO 34
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 34
gatcggccgc agcgcgtaga tgc                                              23

<210> SEQ ID NO 35
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 35
gatcccgcac ggagtcggcg gacag                                            25

<210> SEQ ID NO 36
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 36
tccgacagca tgctctcgac ccaag                                            25

<210> SEQ ID NO 37
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 37
ttccgtccgt ctggcgtgaa gagg                                             24

<210> SEQ ID NO 38
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 38
aaatcccgaa cccgccccca gaac                                             24
```

<210> SEQ ID NO 39
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 39
gcgccaatta ttggccagag atag                                          24

<210> SEQ ID NO 40
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 40
ggcatgggtt cgtccgagga caag                                          24

<210> SEQ ID NO 41
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 41
ttgtcctcgg acgaacccat gccg                                          24

<210> SEQ ID NO 42
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 42
gatccaaatc ccgaacccgc cc                                            22

<210> SEQ ID NO 43
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 43
gtagatgctg ctggaggagt cg                                            22

<210> SEQ ID NO 44
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 44
gtcgtccatc cacctcttca cg                                            22

<210> SEQ ID NO 45
<211> LENGTH: 22
<212> TYPE: DNA
<213> ORGANISM: Artificial Sequence
<220> FEATURE:

-continued

```
<223> OTHER INFORMATION: Description of Artificial Sequence: Primer

<400> SEQUENCE: 45
gccagagata gatagagagg cg                                             22

<210> SEQ ID NO 46
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 46
tagggcttag gagttttacg gg                                             22

<210> SEQ ID NO 47
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 47
cggagtcggc ggacaggtcg gc                                             22

<210> SEQ ID NO 48
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 48
cggagaggtt ctcctgctgc acggc                                          25

<210> SEQ ID NO 49
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 49
tgtgcaaccc cagcgtcagg cag                                            23

<210> SEQ ID NO 50
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 50
gcggcctcgt cgccgccacg ctc                                            23

<210> SEQ ID NO 51
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 51
tggcggcgac gaggccgcgg tac                                            23
```

```
<210> SEQ ID NO 52
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 52
aagaataagg aagagatgga gatggttg                                         28

<210> SEQ ID NO 53
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 53
tctgcaacgt ggtggcctgc gag                                              23

<210> SEQ ID NO 54
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 54
cccctcgcag gccaccacgt tgc                                              23

<210> SEQ ID NO 55
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 55
ttgggtcgag agcatgctgt cggag                                            25

<210> SEQ ID NO 56
<211> LENGTH: 27
<212> TYPE: PRT
<213> ORGANISM: Triticum aestivum

<400> SEQUENCE: 56

Asp Glu Leu Leu Ala Ala Leu Gly Tyr Lys Val Arg Ala Ser Asp Met
 1               5                  10                  15

Ala Asp Val Ala Gln Lys Leu Glu Gln Leu Glu
            20                  25

<210> SEQ ID NO 57
<211> LENGTH: 1746
<212> TYPE: DNA
<213> ORGANISM: Triticum aestivum
<220> FEATURE:
<221> NAME/KEY: misc_feature
<222> LOCATION: (674)
<223> OTHER INFORMATION: n is any nucleotide
<221> NAME/KEY: misc_feature
<222> LOCATION: (680)
<223> OTHER INFORMATION: n is any nucleotide
<221> NAME/KEY: misc_feature
<222> LOCATION: (786)
<223> OTHER INFORMATION: n is any nucleotide
<221> NAME/KEY: misc_feature
<222> LOCATION: (972)
<223> OTHER INFORMATION: n is any nucleotide
```

```
<221> NAME/KEY: misc_feature
<222> LOCATION: (1038)
<223> OTHER INFORMATION: n is any nucleotide
<221> NAME/KEY: misc_feature
<222> LOCATION: (1130)
<223> OTHER INFORMATION: n is any nucleotide
<221> NAME/KEY: misc_feature
<222> LOCATION: (1170)
<223> OTHER INFORMATION: n is any nucleotide
<221> NAME/KEY: misc_feature
<222> LOCATION: (1212)
<223> OTHER INFORMATION: n is any nucleotide

<400> SEQUENCE: 57
ccccgacggt cgcggccgcg gccaacgcga cgcccgcgct gccggtcgtc gtggtcgaca      60
cgcaggaggc cgggattcgg ctggtgcacg cgctgctggc gtgcgcggag gccgtgcagc     120
aggagaacct ctccgccgcg gaggcgctgg tgaagcagat acccttgctg gccgcgtccc     180
agggcggcgc gatgcgcaag gtcgccgcct acttcggcga ggccctcgcc cgccgcgtct     240
tccgcttccg cccgcagccg gacagctccc tcctcgacgc cgccttcgcc gacctcctcc     300
acgcgcactt ctacgagtcc tgcccctacc tcaagttcgc gcacttcacc gccaaccagg     360
ccatcctgga ggcgttcgcc ggctgccgcc gcgtgcacgt cgtcgacttc ggcatcaagc     420
agggatgca gtggcccgca cttctccagg ccctcgccct ccgtcccggc ggccctccct     480
cgttccgcct caccggcgtc ggccccccgc agccggacga gaccgacgcc ctgcagcagg     540
tgggctggaa gctcgcccag ttcgcgcaca ccatccgcgt cgacttccag taccgcggcc     600
tcgtcgccgc cacgctcgcg gacctggagc cgttcatgct gcagccggag ggcgaggagg     660
acccgaacga agancccgan gtaatcgccg tcaactcagt cttcgagatg caccggctgc     720
tcgcgcagcc cggcgccctg gaaaaggttc ttgggcaccg tgcgccccg tgcggcccag     780
aattcntcac cgtggtggaa acaggaggca atcacaact ccggcacatt cctggaccgc     840
ttcaccgagt ctctgcacta ctactccacc atgttcgatt ccctcgaggg cggcagctcc     900
ggcggcggcc catccgaagt ctcatcgggg gctgctgctg ctcctgccgc cgccggcacg     960
gaccaggtca tntccgaggt gtacctcggc cggcagatct gcaacgtggt ggcctgcgag    1020
ggggcggaac gcacagancg ccacgagacg ctgggccagt ggcggaaccg gctgggcaac    1080
gccgggttcg agaccgtcca cctgggctcc aatgcctaca agcaggcgan cacgctgctg    1140
gcgctcttcg ccggcggcga acggctacan gtggaagaaa aggaaggctg cctgacgctg    1200
gggttgcaca cnccccccctg attgccacct cggcatggcg cctggccggg ccgtgatctc    1260
gcgagttttg aacgctgtaa gtacacatcg tgagcatgga ggacaacaca gccccggcgg    1320
ccgcccggc tctccggcga acgcacgcac gcacgcactt gaagaagaag aagctaaatg    1380
tcatgtcagt gagcgctgaa ttgcagcgac cggctacgat cgatcgggct acgggtggtt    1440
ccgtccgtct ggcgtgaaga ggtggatgga cgacgaactc cgagccgacc accaccggca    1500
tgtagtaatg taatcccttc ttcgttccca gttctccacc gcctccatga tcacccgtaa    1560
aactcctaag ccctattatt actactatta tgtttaaatg tctattattg ctatgtgtaa    1620
ttcctccaac cgctcatatc aaaataagca cgggccggaa aaaaaaaaaa aaaaaaaa    1680
aaaaaaaaaa aaaaaaaaaa aaaaaaaaaa aaaaaaaaaa aaaaaaaaaa aaaaaaaaaa    1740
aaaaaa                                                              1746

<210> SEQ ID NO 58
<211> LENGTH: 332
<212> TYPE: DNA
```

```
<213> ORGANISM: Triticum aestivum
<220> FEATURE:
<221> NAME/KEY: misc_feature
<222> LOCATION: (19)
<223> OTHER INFORMATION: n is any nucleotide
<221> NAME/KEY: misc_feature
<222> LOCATION: (33)
<223> OTHER INFORMATION: n is any nucleotide
<221> NAME/KEY: misc_feature
<222> LOCATION: (131)
<223> OTHER INFORMATION: n is any nucleotide

<400> SEQUENCE: 58
cgcgcaatgc ttaaggtcnc cgcctacttc ggngcaggcc ctcgcccgcc gcgtcttccg      60
cttccgcccg cagccggaca gctccctcct cgacgccgcc ttcgccgacc tcctccacgc     120
gcacttctac nagtcctgcc cctacctcaa gttcgcgcac ttcaccgcca attaggccat     180
cctggaggcg ttcgccggct gccgccgcgt gcacgtcgtc gacttcggca tcaagcaggg     240
gatgcagtgg cccgcacttc tccaggccct cgccctccgt cccggcggcc ctccctcgtt     300
ccgcctcacc ggcgtcggcc ccccgcagcc gg                                    332

<210> SEQ ID NO 59
<211> LENGTH: 377
<212> TYPE: DNA
<213> ORGANISM: Triticum aestivum
<220> FEATURE:
<221> NAME/KEY: misc_feature
<222> LOCATION: (17)
<223> OTHER INFORMATION: n is any nucleotide
<221> NAME/KEY: misc_feature
<222> LOCATION: (19)
<223> OTHER INFORMATION: n is any nucleotide
<221> NAME/KEY: misc_feature
<222> LOCATION: (20)
<223> OTHER INFORMATION: n is any nucleotide
<221> NAME/KEY: misc_feature
<222> LOCATION: (53)
<223> OTHER INFORMATION: n is any nucleotide
<221> NAME/KEY: misc_feature
<222> LOCATION: (61)
<223> OTHER INFORMATION: n is any nucleotide
<221> NAME/KEY: misc_feature
<222> LOCATION: (77)
<223> OTHER INFORMATION: n is any nucleotide
<221> NAME/KEY: misc_feature
<222> LOCATION: (84)
<223> OTHER INFORMATION: n is any nucleotide
<221> NAME/KEY: misc_feature
<222> LOCATION: (137)
<223> OTHER INFORMATION: n is any nucleotide
<221> NAME/KEY: misc_feature
<222> LOCATION: (142)
<223> OTHER INFORMATION: n is any nucleotide
<221> NAME/KEY: misc_feature
<222> LOCATION: (156)
<223> OTHER INFORMATION: n is any nucleotide
<221> NAME/KEY: misc_feature
<222> LOCATION: (162)
<223> OTHER INFORMATION: n is any nucleotide
<221> NAME/KEY: misc_feature
<222> LOCATION: (167)
<223> OTHER INFORMATION: n is any nucleotide
<221> NAME/KEY: misc_feature
<222> LOCATION: (205)
<223> OTHER INFORMATION: n is any nucleotide
<221> NAME/KEY: misc_feature
<222> LOCATION: (212)
<223> OTHER INFORMATION: n is any nucleotide
<221> NAME/KEY: misc_feature
<222> LOCATION: (221)
<223> OTHER INFORMATION: n is any nucleotide
<221> NAME/KEY: misc_feature
<222> LOCATION: (251)
```

-continued

```
<223> OTHER INFORMATION: n is any nucleotide
<221> NAME/KEY: misc_feature
<222> LOCATION: (259)
<223> OTHER INFORMATION: n is any nucleotide
<221> NAME/KEY: misc_feature
<222> LOCATION: (271)
<223> OTHER INFORMATION: n is any nucleotide
<221> NAME/KEY: misc_feature
<222> LOCATION: (273)
<223> OTHER INFORMATION: n is any nucleotide
<221> NAME/KEY: misc_feature
<222> LOCATION: (277)
<223> OTHER INFORMATION: n is any nucleotide
<221> NAME/KEY: misc_feature
<222> LOCATION: (290)
<223> OTHER INFORMATION: n is any nucleotide
<221> NAME/KEY: misc_feature
<222> LOCATION: (306)
<223> OTHER INFORMATION: n is any nucleotide
<221> NAME/KEY: misc_feature
<222> LOCATION: (321)
<223> OTHER INFORMATION: n is any nucleotide
<221> NAME/KEY: misc_feature
<222> LOCATION: (342)
<223> OTHER INFORMATION: n is any nucleotide
<221> NAME/KEY: misc_feature
<222> LOCATION: (345)
<223> OTHER INFORMATION: n is any nucleotide
<221> NAME/KEY: misc_feature
<222> LOCATION: (362)
<223> OTHER INFORMATION: n is any nucleotide
<221> NAME/KEY: misc_feature
<222> LOCATION: (367)
<223> OTHER INFORMATION: n is any nucleotide
<221> NAME/KEY: misc_feature
<222> LOCATION: (369)
<223> OTHER INFORMATION: n is any nucleotide

<400> SEQUENCE: 59
acctccttcg tcgtctntnn ggtgggggcg ccaggagctt atgtggtgga ggntggcccc      60
nccggtcgcg accgcgncct acgngacgcc cgcgctgccg gtcgtcgtgg tcgacacgca     120
ggaggccggg attcggntgg tncacgcgct gctgggntgc gnggagnccg tgcagcagga     180
gaacctctcc gccgcggagg cgctngtgaa gnagatiaccc ntgctggccg agtcccaggg     240
cggcgagatg ngcaaggtng cagcttactt ngnagangcc ctcgcccgcn gagtgattcc     300
acttancgcc tgcagccgga nagctccgtc ctcgaanccg cnttngccga cctcctccac     360
gngcacntnt acgagtc                                                   377

<210> SEQ ID NO 60
<211> LENGTH: 211
<212> TYPE: DNA
<213> ORGANISM: Triticum aestivum
<220> FEATURE:
<221> NAME/KEY: misc_feature
<222> LOCATION: (3)
<223> OTHER INFORMATION: n is any nucleotide
<221> NAME/KEY: misc_feature
<222> LOCATION: (34)
<223> OTHER INFORMATION: n is any nucleotide
<221> NAME/KEY: misc_feature
<222> LOCATION: (45)
<223> OTHER INFORMATION: n is any nucleotide
<221> NAME/KEY: misc_feature
<222> LOCATION: (142)
<223> OTHER INFORMATION: n is any nucleotide
<221> NAME/KEY: misc_feature
<222> LOCATION: (176)
<223> OTHER INFORMATION: n is any nucleotide
<221> NAME/KEY: misc_feature
<222> LOCATION: (179)
<223> OTHER INFORMATION: n is any nucleotide
<221> NAME/KEY: misc_feature
```

```
<222> LOCATION: (185)
<223> OTHER INFORMATION: n is any nucleotide
<221> NAME/KEY: misc_feature
<222> LOCATION: (186)
<223> OTHER INFORMATION: n is any nucleotide
<221> NAME/KEY: misc_feature
<222> LOCATION: (187)
<223> OTHER INFORMATION: n is any nucleotide
<221> NAME/KEY: misc_feature
<222> LOCATION: (188)
<223> OTHER INFORMATION: n is any nucleotide
<221> NAME/KEY: misc_feature
<222> LOCATION: (189)
<223> OTHER INFORMATION: n is any nucleotide
<221> NAME/KEY: misc_feature
<222> LOCATION: (191)
<223> OTHER INFORMATION: n is any nucleotide
<221> NAME/KEY: misc_feature
<222> LOCATION: (197)
<223> OTHER INFORMATION: n is any nucleotide
<221> NAME/KEY: misc_feature
<222> LOCATION: (198)
<223> OTHER INFORMATION: n is any nucleotide
<221> NAME/KEY: misc_feature
<222> LOCATION: (210)
<223> OTHER INFORMATION: n is any nucleotide

<400> SEQUENCE: 60
tantagtctc tcggtggggg cgccaggagc tctntggtgg aggcngcccc gccggtcgcg      60
gccgcggcca acgcgacgcc cgcgctgccg gtcgtcgtgg tcgacacgca ggaggccggg     120
attcggatgg tgcacgcgct gntggcgtgc gcggaggccg tgaaacagtt gaaggnccnc     180
gcctnnnnnc ncacaanntg aaagccccgn g                                    211

<210> SEQ ID NO 61
<211> LENGTH: 369
<212> TYPE: DNA
<213> ORGANISM: Triticum aestivum
<220> FEATURE:
<221> NAME/KEY: misc_feature
<222> LOCATION: (5)
<223> OTHER INFORMATION: n is any nucleotide
<221> NAME/KEY: misc_feature
<222> LOCATION: (8)
<223> OTHER INFORMATION: n is any nucleotide
<221> NAME/KEY: misc_feature
<222> LOCATION: (11)
<223> OTHER INFORMATION: n is any nucleotide
<221> NAME/KEY: misc_feature
<222> LOCATION: (51)
<223> OTHER INFORMATION: n is any nucleotide
<221> NAME/KEY: misc_feature
<222> LOCATION: (56)
<223> OTHER INFORMATION: n is any nucleotide
<221> NAME/KEY: misc_feature
<222> LOCATION: (59)
<223> OTHER INFORMATION: n is any nucleotide
<221> NAME/KEY: misc_feature
<222> LOCATION: (69)
<223> OTHER INFORMATION: n is any nucleotide
<221> NAME/KEY: misc_feature
<222> LOCATION: (156)
<223> OTHER INFORMATION: n is any nucleotide
<221> NAME/KEY: misc_feature
<222> LOCATION: (210)
<223> OTHER INFORMATION: n is any nucleotide
<221> NAME/KEY: misc_feature
<222> LOCATION: (264)
<223> OTHER INFORMATION: n is any nucleotide
<221> NAME/KEY: misc_feature
<222> LOCATION: (345)
<223> OTHER INFORMATION: n is any nucleotide
<221> NAME/KEY: misc_feature
<222> LOCATION: (350)
<223> OTHER INFORMATION: n is any nucleotide
```

```
<221> NAME/KEY: misc_feature
<222> LOCATION: (360)
<223> OTHER INFORMATION: n is any nucleotide
<221> NAME/KEY: misc_feature
<222> LOCATION: (367)
<223> OTHER INFORMATION: n is any nucleotide

<400> SEQUENCE: 61
ggctnccncc ncgtgcacgt cgtcgacttc ggcatcaagc atgggatgca ntggcncgna      60
cttctccang ccctcgccct ccgtcccggc ggccctccct cgttccgcct caccggcgtc     120 ggcccccgc agccggacga gaccgacgcc ctgcancagg tgggctggaa gctcgcccag      180
ttcgcgcaca ccatccgcgt cgacttccan taccgtggcc tcgtcgccgc cacgctcgcg     240
gacctggagc cgttcatgct gcanccggag ggcgaggagg acccgaacga cggagcccga     300
ggtaatcgcc gtcaactcag tcttcgagat gcaccgggct gctcncgcan cccggcgacn     360 ctggaanaa                                                            369

<210> SEQ ID NO 62
<211> LENGTH: 357
<212> TYPE: DNA
<213> ORGANISM: Triticum aestivum
<220> FEATURE:
<221> NAME/KEY: misc_feature
<222> LOCATION: (6)
<223> OTHER INFORMATION: n is any nucleotide
<221> NAME/KEY: misc_feature
<222> LOCATION: (57)
<223> OTHER INFORMATION: n is any nucleotide
<221> NAME/KEY: misc_feature
<222> LOCATION: (177)
<223> OTHER INFORMATION: n is any nucleotide
<221> NAME/KEY: misc_feature
<222> LOCATION: (235)
<223> OTHER INFORMATION: n is any nucleotide
<221> NAME/KEY: misc_feature
<222> LOCATION: (238)
<223> OTHER INFORMATION: n is any nucleotide
<221> NAME/KEY: misc_feature
<222> LOCATION: (251)
<223> OTHER INFORMATION: n is any nucleotide
<221> NAME/KEY: misc_feature
<222> LOCATION: (286)
<223> OTHER INFORMATION: n is any nucleotide
<221> NAME/KEY: misc_feature
<222> LOCATION: (293)
<223> OTHER INFORMATION: n is any nucleotide
<221> NAME/KEY: misc_feature
<222> LOCATION: (294)
<223> OTHER INFORMATION: n is any nucleotide
<221> NAME/KEY: misc_feature
<222> LOCATION: (295)
<223> OTHER INFORMATION: n is any nucleotide
<221> NAME/KEY: misc_feature
<222> LOCATION: (296)
<223> OTHER INFORMATION: n is any nucleotide
<221> NAME/KEY: misc_feature
<222> LOCATION: (328)
<223> OTHER INFORMATION: n is any nucleotide
<221> NAME/KEY: misc_feature
<222> LOCATION: (331)
<223> OTHER INFORMATION: n is any nucleotide
<221> NAME/KEY: misc_feature
<222> LOCATION: (332)
<223> OTHER INFORMATION: n is any nucleotide
<221> NAME/KEY: misc_feature
<222> LOCATION: (333)
<223> OTHER INFORMATION: n is any nucleotide

<400> SEQUENCE: 62
caagangcta atcacaactc cggcacattc ctggaccgct tcaccgagtc tctgcantac      60
```

-continued

```
tactccacca tgttcgattc cctcgagggc ggcagctccg gcggcggccc atccgaagtc      120
tcatcggggg ctgctgctgc tcctgccgcc gccggcacgg accatgtcat gtccgangtg      180
tacctcggcc ggcagatctg caacgtggtg gcctgcgagg gggcggagcg cacantancg      240
ccacgcagac nctgggccag tggcgtgaac cggctgggca acgccnggtt cannnnccgt      300
ccacctgggc tccaatgcct acaatcangc nnncacgctg ctggcgcctc ttcgccc         357
```

```
<210> SEQ ID NO 63
<211> LENGTH: 511
<212> TYPE: DNA
<213> ORGANISM: Triticum aestivum
<220> FEATURE:
<221> NAME/KEY: misc_feature
<222> LOCATION: (7)
<223> OTHER INFORMATION: n is any nucleotide
<221> NAME/KEY: misc_feature
<222> LOCATION: (17)
<223> OTHER INFORMATION: n is any nucleotide
<221> NAME/KEY: misc_feature
<222> LOCATION: (149)
<223> OTHER INFORMATION: n is any nucleotide
<221> NAME/KEY: misc_feature
<222> LOCATION: (263)
<223> OTHER INFORMATION: n is any nucleotide
<221> NAME/KEY: misc_feature
<222> LOCATION: (361)
<223> OTHER INFORMATION: n is any nucleotide
<221> NAME/KEY: misc_feature
<222> LOCATION: (362)
<223> OTHER INFORMATION: n is any nucleotide
<221> NAME/KEY: misc_feature
<222> LOCATION: (413)
<223> OTHER INFORMATION: n is any nucleotide
<221> NAME/KEY: misc_feature
<222> LOCATION: (438)
<223> OTHER INFORMATION: n is any nucleotide
<221> NAME/KEY: misc_feature
<222> LOCATION: (479)
<223> OTHER INFORMATION: n is any nucleotide
<221> NAME/KEY: misc_feature
<222> LOCATION: (484)
<223> OTHER INFORMATION: n is any nucleotide
<221> NAME/KEY: misc_feature
<222> LOCATION: (491)
<223> OTHER INFORMATION: n is any nucleotide
<221> NAME/KEY: misc_feature
<222> LOCATION: (496)
<223> OTHER INFORMATION: n is any nucleotide
<221> NAME/KEY: misc_feature
<222> LOCATION: (510)
<223> OTHER INFORMATION: n is any nucleotide

<400> SEQUENCE: 63
```

```
tcgccantcg gcatggngcc tggccgggcc gtgatctcgc gagttttgaa cgctgtaagt      60
acacatcgtg agcatggagg acaacacagc cccggcggcc gccccggctc tccggcgaac     120
gcacgcacgc acgcacttgg aagaagaana agctaaatgt catgtcagtg agcgctgaat     180
tgcaacgacc ggctacgatc gatcgggcta cgggtggttc cgtccgtctg gcgtgaagag     240
gtggatggac gacgaactcc ganccgacca ccaccggcat gtagtaatgt aatcccttct     300
tcgttcccag ttctccaccg cctccatgga tcacccgtaa aactcctaag ccctaattat     360
nnactaacta attatgttttt aaaatgttct aattaattgg ctatgttgta atncctccaa    420
accggctcat tttcaaanat taagccacgg gcccggaact tggtttaac aacctcccna     480 ttgnaaaatt naaatngaaa ttttttggttn c                                   511
```

```
<210> SEQ ID NO 64
<211> LENGTH: 309
```

```
<212> TYPE: DNA
<213> ORGANISM: Triticum aestivum
<220> FEATURE:
<221> NAME/KEY: misc_feature
<222> LOCATION: (9)
<223> OTHER INFORMATION: n is any nucleotide
<221> NAME/KEY: misc_feature
<222> LOCATION: (46)
<223> OTHER INFORMATION: n is any nucleotide
<221> NAME/KEY: misc_feature
<222> LOCATION: (50)
<223> OTHER INFORMATION: n is any nucleotide
<221> NAME/KEY: misc_feature
<222> LOCATION: (72)
<223> OTHER INFORMATION: n is any nucleotide
<221> NAME/KEY: misc_feature
<222> LOCATION: (95)
<223> OTHER INFORMATION: n is any nucleotide
<221> NAME/KEY: misc_feature
<222> LOCATION: (131)
<223> OTHER INFORMATION: n is any nucleotide
<221> NAME/KEY: misc_feature
<222> LOCATION: (141)
<223> OTHER INFORMATION: n is any nucleotide
<221> NAME/KEY: misc_feature
<222> LOCATION: (154)
<223> OTHER INFORMATION: n is any nucleotide
<221> NAME/KEY: misc_feature
<222> LOCATION: (160)
<223> OTHER INFORMATION: n is any nucleotide
<221> NAME/KEY: misc_feature
<222> LOCATION: (172)
<223> OTHER INFORMATION: n is any nucleotide
<221> NAME/KEY: misc_feature
<222> LOCATION: (176)
<223> OTHER INFORMATION: n is any nucleotide
<221> NAME/KEY: misc_feature
<222> LOCATION: (214)
<223> OTHER INFORMATION: n is any nucleotide
<221> NAME/KEY: misc_feature
<222> LOCATION: (222)
<223> OTHER INFORMATION: n is any nucleotide

<400> SEQUENCE: 64
gttggtggng gcgatttggg tacaaggtgc gcgcctccga catggnggan gtggggcaga      60
agctggagca gntcgagatg gccatgggga tgggnggcgt gggcgctggc gccgcccctg     120
acgacaggtt ngccacccgc nggccgcgga cacngtgcan tacaacccca cngacntgtc     180
gtcttgggtc gagagcatgc tgtcggagct aaangagccg cngccgcccc tcccgcccgc     240
cccgcagctc aacgcctcca cctcctccac cgtcacgggc agcggcggct acttcgataa     300
ccctccctg                                                             309

<210> SEQ ID NO 65
<211> LENGTH: 399
<212> TYPE: DNA
<213> ORGANISM: Triticum aestivum
<220> FEATURE:
<221> NAME/KEY: misc_feature
<222> LOCATION: (7)
<223> OTHER INFORMATION: n is any nucleotide
<221> NAME/KEY: misc_feature
<222> LOCATION: (13)
<223> OTHER INFORMATION: n is any nucleotide
<221> NAME/KEY: misc_feature
<222> LOCATION: (17)
<223> OTHER INFORMATION: n is any nucleotide
<221> NAME/KEY: misc_feature
<222> LOCATION: (24)
<223> OTHER INFORMATION: n is any nucleotide
<221> NAME/KEY: misc_feature
<222> LOCATION: (37)
<223> OTHER INFORMATION: n is any nucleotide
<221> NAME/KEY: misc_feature
```

```
<222> LOCATION: (45)
<223> OTHER INFORMATION: n is any nucleotide
<221> NAME/KEY: misc_feature
<222> LOCATION: (46)
<223> OTHER INFORMATION: n is any nucleotide
<221> NAME/KEY: misc_feature
<222> LOCATION: (55)
<223> OTHER INFORMATION: n is any nucleotide
<221> NAME/KEY: misc_feature
<222> LOCATION: (60)
<223> OTHER INFORMATION: n is any nucleotide
<221> NAME/KEY: misc_feature
<222> LOCATION: (61)
<223> OTHER INFORMATION: n is any nucleotide
<221> NAME/KEY: misc_feature
<222> LOCATION: (87)
<223> OTHER INFORMATION: n is any nucleotide
<221> NAME/KEY: misc_feature
<222> LOCATION: (108)
<223> OTHER INFORMATION: n is any nucleotide
<221> NAME/KEY: misc_feature
<222> LOCATION: (123)
<223> OTHER INFORMATION: n is any nucleotide
<221> NAME/KEY: misc_feature
<222> LOCATION: (130)
<223> OTHER INFORMATION: n is any nucleotide
<221> NAME/KEY: misc_feature
<222> LOCATION: (135)
<223> OTHER INFORMATION: n is any nucleotide
<221> NAME/KEY: misc_feature
<222> LOCATION: (163)
<223> OTHER INFORMATION: n is any nucleotide
<221> NAME/KEY: misc_feature
<222> LOCATION: (176)
<223> OTHER INFORMATION: n is any nucleotide
<221> NAME/KEY: misc_feature
<222> LOCATION: (233)
<223> OTHER INFORMATION: n is any nucleotide
<221> NAME/KEY: misc_feature
<222> LOCATION: (347)
<223> OTHER INFORMATION: n is any nucleotide
<221> NAME/KEY: misc_feature
<222> LOCATION: (350)
<223> OTHER INFORMATION: n is any nucleotide
<221> NAME/KEY: misc_feature
<222> LOCATION: (370)
<223> OTHER INFORMATION: n is any nucleotide
<221> NAME/KEY: misc_feature
<222> LOCATION: (378)
<223> OTHER INFORMATION: n is any nucleotide
<221> NAME/KEY: misc_feature
<222> LOCATION: (379)
<223> OTHER INFORMATION: n is any nucleotide
<221> NAME/KEY: misc_feature
<222> LOCATION: (383)
<223> OTHER INFORMATION: n is any nucleotide
<221> NAME/KEY: misc_feature
<222> LOCATION: (386)
<223> OTHER INFORMATION: n is any nucleotide
<221> NAME/KEY: misc_feature
<222> LOCATION: (399)
<223> OTHER INFORMATION: n is any nucleotide

<400> SEQUENCE: 65
tgatggnggg agnttangggg ttanaaatgt gggggganttc cgaanngtgg agganatatn      60
ntcagaagtt ggagcagatg agagatngct gatggggata gggtaggngt gggtgccggt     120
gcngcccccn agganagatt ggccacccac ttagcaagtg ganaccgtgg attacnaccc     180
cacagacctg tcgtggttgg gttttgagagc gtggtgtggg agctgaacgg gcngcggcgt     240
gcccctcccg cccgccccgc agctcaacgc ctccacctcc tccaccgtac acgggcagcg     300
gcggctagtt cgatctcccg ccctccgtcg actcctccag cagcatntan gcgctgcggc     360
cgatcccctn cccaagcnng cgnggnccga gccgtgtan                            399
```

<210> SEQ ID NO 66
<211> LENGTH: 453
<212> TYPE: DNA
<213> ORGANISM: Triticum aestivum
<220> FEATURE:
<221> NAME/KEY: misc_feature
<222> LOCATION: (6)
<223> OTHER INFORMATION: n is any nucleotide
<221> NAME/KEY: misc_feature
<222> LOCATION: (11)
<223> OTHER INFORMATION: n is any nucleotide
<221> NAME/KEY: misc_feature
<222> LOCATION: (46)
<223> OTHER INFORMATION: n is any nucleotide
<221> NAME/KEY: misc_feature
<222> LOCATION: (85)
<223> OTHER INFORMATION: n is any nucleotide
<221> NAME/KEY: misc_feature
<222> LOCATION: (107)
<223> OTHER INFORMATION: n is any nucleotide
<221> NAME/KEY: misc_feature
<222> LOCATION: (445)
<223> OTHER INFORMATION: n is any nucleotide
<221> NAME/KEY: misc_feature
<222> LOCATION: (449)
<223> OTHER INFORMATION: n is any nucleotide

<400> SEQUENCE: 66
tttcantttc ntccttttt cttcttttc caaccccgg ccccngacc cttggatcca      60 aatcccgaac ccgcccccag aaccnggaac cgaggccaag caaaagnttt gcgccaatta     120
ttggccagag atagatagag aggcgaggta gctcgcggat catgaagcgg gagtaccagg    180
acgccggagg gagcggcggc ggcggtggcg gcatgggttc gtccgaggac aagatgatgg    240
tgtcggcggc ggcgggggag ggggaggagg tggacgagct gctggcggcg ctcgggtaca    300
aggtgcgcgc ctccgacatg gcggacgtgg cgcagaagct ggagcagctc gagatggcca    360
tggggatggg cggcgtgggc gccggcgccg cccccgacga cagcttcgcc acccacctcg    420
ccacggacac cgtgcagtac aaccncccng acc                                 453

<210> SEQ ID NO 67
<211> LENGTH: 472
<212> TYPE: DNA
<213> ORGANISM: Triticum aestivum
<220> FEATURE:
<221> NAME/KEY: misc_feature
<222> LOCATION: (57)
<223> OTHER INFORMATION: n is any nucleotide
<221> NAME/KEY: misc_feature
<222> LOCATION: (66)
<223> OTHER INFORMATION: n is any nucleotide
<221> NAME/KEY: misc_feature
<222> LOCATION: (127)
<223> OTHER INFORMATION: n is any nucleotide
<221> NAME/KEY: misc_feature
<222> LOCATION: (131)
<223> OTHER INFORMATION: n is any nucleotide
<221> NAME/KEY: misc_feature
<222> LOCATION: (147)
<223> OTHER INFORMATION: n is any nucleotide
<221> NAME/KEY: misc_feature
<222> LOCATION: (201)
<223> OTHER INFORMATION: n is any nucleotide
<221> NAME/KEY: misc_feature
<222> LOCATION: (367)
<223> OTHER INFORMATION: n is any nucleotide
<221> NAME/KEY: misc_feature
<222> LOCATION: (401)
<223> OTHER INFORMATION: n is any nucleotide
<221> NAME/KEY: misc_feature
<222> LOCATION: (444)
<223> OTHER INFORMATION: n is any nucleotide -continued
<221> NAME/KEY: misc_feature
<222> LOCATION: (452)
<223> OTHER INFORMATION: n is any nucleotide
<221> NAME/KEY: misc_feature
<222> LOCATION: (469)
<223> OTHER INFORMATION: n is any nucleotide

<400> SEQUENCE: 67

```
ggacgacgac ctccgagccg accaccaccg gcatgtagta atgtaatccc ttcttcnttc     60
ccagtnctcc accgcctcca tgatcacccg taaaactcct aagcccctatt attactacta  120
ttatgtntaa ntgtctatta ttgctangtg taattcctcc aaccgctcat atcaaaataa  180
gcacgggccg gactttgtta ncagctccaa tgagaatgaa atgaattttg tacgcaaggc  240
acgtccaaaa ctgggctgag ctttgttctg ttctgttatg ttcatggtgc tcactgctct  300
gatgaacatg atggtgcctc caatggtggc tttgcaattg ttgaaacgtt tggcttgggg  360
gacttgngtg ggtgggtgca tgggatgaa tattcacatc nccggattaa aattaagcca  420
tcccgttggc cgtcctttga atancttgcc cnaaacgaaa tttcccccna tc          472
```

<210> SEQ ID NO 68
<211> LENGTH: 233
<212> TYPE: DNA
<213> ORGANISM: Triticum aestivum
<220> FEATURE:
<221> NAME/KEY: misc_feature
<222> LOCATION: (4)
<223> OTHER INFORMATION: n is any nucleotide
<221> NAME/KEY: misc_feature
<222> LOCATION: (9)
<223> OTHER INFORMATION: n is any nucleotide
<221> NAME/KEY: misc_feature
<222> LOCATION: (12)
<223> OTHER INFORMATION: n is any nucleotide
<221> NAME/KEY: misc_feature
<222> LOCATION: (28)
<223> OTHER INFORMATION: n is any nucleotide
<221> NAME/KEY: misc_feature
<222> LOCATION: (31)
<223> OTHER INFORMATION: n is any nucleotide
<221> NAME/KEY: misc_feature
<222> LOCATION: (36)
<223> OTHER INFORMATION: n is any nucleotide
<221> NAME/KEY: misc_feature
<222> LOCATION: (41)
<223> OTHER INFORMATION: n is any nucleotide
<221> NAME/KEY: misc_feature
<222> LOCATION: (42)
<223> OTHER INFORMATION: n is any nucleotide
<221> NAME/KEY: misc_feature
<222> LOCATION: (46)
<223> OTHER INFORMATION: n is any nucleotide
<221> NAME/KEY: misc_feature
<222> LOCATION: (54)
<223> OTHER INFORMATION: n is any nucleotide
<221> NAME/KEY: misc_feature
<222> LOCATION: (56)
<223> OTHER INFORMATION: n is any nucleotide
<221> NAME/KEY: misc_feature
<222> LOCATION: (60)
<223> OTHER INFORMATION: n is any nucleotide
<221> NAME/KEY: misc_feature
<222> LOCATION: (63)
<223> OTHER INFORMATION: n is any nucleotide
<221> NAME/KEY: misc_feature
<222> LOCATION: (92)
<223> OTHER INFORMATION: n is any nucleotide
<221> NAME/KEY: misc_feature
<222> LOCATION: (157)
<223> OTHER INFORMATION: n is any nucleotide
<221> NAME/KEY: misc_feature
<222> LOCATION: (161)
<223> OTHER INFORMATION: n is any nucleotide

```
<221> NAME/KEY: misc_feature
<222> LOCATION: (173)
<223> OTHER INFORMATION: n is any nucleotide
<221> NAME/KEY: misc_feature
<222> LOCATION: (184)
<223> OTHER INFORMATION: n is any nucleotide
<221> NAME/KEY: misc_feature
<222> LOCATION: (195)
<223> OTHER INFORMATION: n is any nucleotide
<221> NAME/KEY: misc_feature
<222> LOCATION: (198)
<223> OTHER INFORMATION: n is any nucleotide
<221> NAME/KEY: misc_feature
<222> LOCATION: (200)
<223> OTHER INFORMATION: n is any nucleotide
<221> NAME/KEY: misc_feature
<222> LOCATION: (205)
<223> OTHER INFORMATION: n is any nucleotide
<221> NAME/KEY: misc_feature
<222> LOCATION: (213)
<223> OTHER INFORMATION: n is any nucleotide

<400> SEQUENCE: 68
aaancctana anatatagag gcgatgtngc nccccnatca nnaacnggat tacngnaacn    60
ccngaaggag cggcggcggc ggtggcagca tnggctcgtc cgatgacaaa tatcatggtg   120
tcggcggcgg cggggganggg ggaggaggtg cacaacnttt nggcgggact cgngtaccac   180
gtgnacggtg ccgcnctngn ggatntggcc ctngaagatg ggccacctcc aaa           233

<210> SEQ ID NO 69
<211> LENGTH: 200
<212> TYPE: DNA
<213> ORGANISM: Triticum aestivum
<220> FEATURE:
<221> NAME/KEY: misc_feature
<222> LOCATION: (37)
<223> OTHER INFORMATION: n is any nucleotide
<221> NAME/KEY: misc_feature
<222> LOCATION: (66)
<223> OTHER INFORMATION: n is any nucleotide
<221> NAME/KEY: misc_feature
<222> LOCATION: (164)
<223> OTHER INFORMATION: n is any nucleotide
<221> NAME/KEY: misc_feature
<222> LOCATION: (172)
<223> OTHER INFORMATION: n is any nucleotide
<221> NAME/KEY: misc_feature
<222> LOCATION: (179)
<223> OTHER INFORMATION: n is any nucleotide
<221> NAME/KEY: misc_feature
<222> LOCATION: (185)
<223> OTHER INFORMATION: n is any nucleotide
<221> NAME/KEY: misc_feature
<222> LOCATION: (188)
<223> OTHER INFORMATION: n is any nucleotide

<400> SEQUENCE: 69
cggcggcccc gtggcggcat gggctcgtcc gaggacnaga tgatggtgtc ggcggcggcg    60
ggggangggg atgatgtgga ctatctgctg gcggcgctcg ggtacaaggt gcgcgcctcc   120
gacaggcgga gcccgcgcat aactggagcc gctcgagatg gccntgggga tnggcggcnt   180
gggcnccngc gcctcccccg                                                 200

<210> SEQ ID NO 70
<211> LENGTH: 230
<212> TYPE: DNA
<213> ORGANISM: Triticum aestivum
<220> FEATURE:
<221> NAME/KEY: misc_feature
<222> LOCATION: (4)
```

```
<223> OTHER INFORMATION: n is any nucleotide
<221> NAME/KEY: misc_feature
<222> LOCATION: (14)
<223> OTHER INFORMATION: n is any nucleotide
<221> NAME/KEY: misc_feature
<222> LOCATION: (202)
<223> OTHER INFORMATION: n is any nucleotide
<221> NAME/KEY: misc_feature
<222> LOCATION: (210)
<223> OTHER INFORMATION: n is any nucleotide
<221> NAME/KEY: misc_feature
<222> LOCATION: (214)
<223> OTHER INFORMATION: n is any nucleotide

<400> SEQUENCE: 70
tggngctcgg gtgncccgtg cgcgcctccg acatggcggg acgtggcgca gaactggagc      60
agctcgagat ggccatgggg atgggcggcg tgggcgccgg cgccgccccc gacgacagct     120
tcgccaccca cctcgccacg gacaccggca cacaacccca ccgacctgtc gtcttgggtc     180
gagagcatgc tgtcggatct cnacgcgccn ccgncgcccc tcccgcccgc                230

<210> SEQ ID NO 71
<211> LENGTH: 377
<212> TYPE: DNA
<213> ORGANISM: Triticum aestivum
<220> FEATURE:
<221> NAME/KEY: misc_feature
<222> LOCATION: (2)
<223> OTHER INFORMATION: n is any nucleotide
<221> NAME/KEY: misc_feature
<222> LOCATION: (3)
<223> OTHER INFORMATION: n is any nucleotide
<221> NAME/KEY: misc_feature
<222> LOCATION: (8)
<223> OTHER INFORMATION: n is any nucleotide
<221> NAME/KEY: misc_feature
<222> LOCATION: (10)
<223> OTHER INFORMATION: n is any nucleotide
<221> NAME/KEY: misc_feature
<222> LOCATION: (11)
<223> OTHER INFORMATION: n is any nucleotide
<221> NAME/KEY: misc_feature
<222> LOCATION: (12)
<223> OTHER INFORMATION: n is any nucleotide
<221> NAME/KEY: misc_feature
<222> LOCATION: (13)
<223> OTHER INFORMATION: n is any nucleotide
<221> NAME/KEY: misc_feature
<222> LOCATION: (25)
<223> OTHER INFORMATION: n is any nucleotide
<221> NAME/KEY: misc_feature
<222> LOCATION: (33)
<223> OTHER INFORMATION: n is any nucleotide
<221> NAME/KEY: misc_feature
<222> LOCATION: (39)
<223> OTHER INFORMATION: n is any nucleotide
<221> NAME/KEY: misc_feature
<222> LOCATION: (365)
<223> OTHER INFORMATION: n is any nucleotide

<400> SEQUENCE: 71
annttgtncn nnntacatcc catgngccgc gcnatgctna aggtcgccgc ctacttcggc      60
gcaggccctc gccgccgcg tcttccgctt ccgcccgcag ccggacagct ccctcctcga     120
cgccgccttc gccgacctcc tccacgcgca cttctacgag tcctgcccct acctcaagtt     180
cgcgcacttc accgccaacc aggccatcct ggaggcgttc gccggctgcc gccgcgtgca     240
cgtcgtcgac ttcggcatca agcaggggat gcagtggccc gcacttctcc aggccctcgc     300
cctccgtccc ggcggccctc cctcgttccg cctcaccggc gttcggcccc cgcagccgg     360 acganaacga cgccctg                                                    377
```

<210> SEQ ID NO 72
<211> LENGTH: 436
<212> TYPE: DNA
<213> ORGANISM: Triticum aestivum
<220> FEATURE:
<221> NAME/KEY: misc_feature
<222> LOCATION: (1)
<223> OTHER INFORMATION: n is any nucleotide
<221> NAME/KEY: misc_feature
<222> LOCATION: (21)
<223> OTHER INFORMATION: n is any nucleotide
<221> NAME/KEY: misc_feature
<222> LOCATION: (54)
<223> OTHER INFORMATION: n is any nucleotide
<221> NAME/KEY: misc_feature
<222> LOCATION: (60)
<223> OTHER INFORMATION: n is any nucleotide
<221> NAME/KEY: misc_feature
<222> LOCATION: (225)
<223> OTHER INFORMATION: n is any nucleotide
<221> NAME/KEY: misc_feature
<222> LOCATION: (267)
<223> OTHER INFORMATION: n is any nucleotide
<221> NAME/KEY: misc_feature
<222> LOCATION: (364)
<223> OTHER INFORMATION: n is any nucleotide
<221> NAME/KEY: misc_feature
<222> LOCATION: (385)
<223> OTHER INFORMATION: n is any nucleotide
<221> NAME/KEY: misc_feature
<222> LOCATION: (394)
<223> OTHER INFORMATION: n is any nucleotide
<221> NAME/KEY: misc_feature
<222> LOCATION: (404)
<223> OTHER INFORMATION: n is any nucleotide
<221> NAME/KEY: misc_feature
<222> LOCATION: (412)
<223> OTHER INFORMATION: n is any nucleotide
<221> NAME/KEY: misc_feature
<222> LOCATION: (415)
<223> OTHER INFORMATION: n is any nucleotide
<221> NAME/KEY: misc_feature
<222> LOCATION: (416)
<223> OTHER INFORMATION: n is any nucleotide
<221> NAME/KEY: misc_feature
<222> LOCATION: (425)
<223> OTHER INFORMATION: n is any nucleotide
<221> NAME/KEY: misc_feature
<222> LOCATION: (426)
<223> OTHER INFORMATION: n is any nucleotide
<221> NAME/KEY: misc_feature
<222> LOCATION: (427)
<223> OTHER INFORMATION: n is any nucleotide
<221> NAME/KEY: misc_feature
<222> LOCATION: (433)
<223> OTHER INFORMATION: n is any nucleotide
<221> NAME/KEY: misc_feature
<222> LOCATION: (436)
<223> OTHER INFORMATION: n is any nucleotide

<400> SEQUENCE: 72

```
nttccccggc agttaaaagc ntccacttct tccaccgtca cgggcagcgg cggntacttn      60
gatctcccgc cctcagtcga ctcctccagc agcatctacg cgctgcggcc gatcccctcc     120
ccggccggcg cgacggcgcc ggccgacctg tccgccgact ccgtgcggga tcccaagcgg     180
atgcgcactg gcgggagcag cacctcgtcg tcatcctcct catantcgtc tctcggtggg     240
ggcgccagga gctctgtggt ggaggcngcc ccgccggtcg cggccgcggc caacgcgacg     300
cccgcgctgc cggtcgtcgt ggtcgacacg caggaggccg ggattcggat ggtgcacgcg     360
ctgntggcgt gcgcggaggc cgtgnaagca gttngaaggg cctncgccgt gnatnncgca     420
acaannngga agnccn                                                     436
```

<210> SEQ ID NO 73
<211> LENGTH: 425
<212> TYPE: DNA
<213> ORGANISM: Triticum aestivum
<220> FEATURE:
<221> NAME/KEY: misc_feature
<222> LOCATION: (3)
<223> OTHER INFORMATION: n is any nucleotide
<221> NAME/KEY: misc_feature
<222> LOCATION: (11)
<223> OTHER INFORMATION: n is any nucleotide
<221> NAME/KEY: misc_feature
<222> LOCATION: (196)
<223> OTHER INFORMATION: n is any nucleotide
<221> NAME/KEY: misc_feature
<222> LOCATION: (274)
<223> OTHER INFORMATION: n is any nucleotide
<221> NAME/KEY: misc_feature
<222> LOCATION: (369)
<223> OTHER INFORMATION: n is any nucleotide
<221> NAME/KEY: misc_feature
<222> LOCATION: (370)
<223> OTHER INFORMATION: n is any nucleotide
<221> NAME/KEY: misc_feature
<222> LOCATION: (371)
<223> OTHER INFORMATION: n is any nucleotide
<221> NAME/KEY: misc_feature
<222> LOCATION: (379)
<223> OTHER INFORMATION: n is any nucleotide
<221> NAME/KEY: misc_feature
<222> LOCATION: (394)
<223> OTHER INFORMATION: n is any nucleotide
<221> NAME/KEY: misc_feature
<222> LOCATION: (402)
<223> OTHER INFORMATION: n is any nucleotide
<221> NAME/KEY: misc_feature
<222> LOCATION: (414)
<223> OTHER INFORMATION: n is any nucleotide
<221> NAME/KEY: misc_feature
<222> LOCATION: (423)
<223> OTHER INFORMATION: n is any nucleotide

<400> SEQUENCE: 73

```
canccgctg ntcgccacct cggcatggcg cctggccggg ccgtgatctc gcgagttttg      60
aacgctgtaa gtacacatcg tgagcatgga ggacaacaca gccccggcgg ccgcccggc     120 tctccggcga acgcacgcac gcacgcactt gaagaagaag aagctaaatg tcatgtcagt    180
gagcgctgaa ttgcancgac cggctacgat cgatcgggct acgggtggtt ccgtccgtct    240
ggcgtgaaga ggtggatgga cgacgaactc cganccgacc accaccggca tgtagtaatg    300
taatcccttc ttcgttccca gtttctccac cgcctccatg atcaccccgt aaaactccta    360
agccctatnn nttactacna ttaatgtttt aaantgttct antaattgct atgntgttta    420 ttncc                                                                425
```

<210> SEQ ID NO 74
<211> LENGTH: 285
<212> TYPE: DNA
<213> ORGANISM: Triticum aestivum
<220> FEATURE:
<221> NAME/KEY: misc_feature
<222> LOCATION: (24)
<223> OTHER INFORMATION: n is any nucleotide
<221> NAME/KEY: misc_feature
<222> LOCATION: (90)
<223> OTHER INFORMATION: n is any nucleotide
<221> NAME/KEY: misc_feature
<222> LOCATION: (121)
<223> OTHER INFORMATION: n is any nucleotide
<221> NAME/KEY: misc_feature
<222> LOCATION: (170)

```
<223> OTHER INFORMATION: n is any nucleotide
<221> NAME/KEY: misc_feature
<222> LOCATION: (173)
<223> OTHER INFORMATION: n is any nucleotide
<221> NAME/KEY: misc_feature
<222> LOCATION: (194)
<223> OTHER INFORMATION: n is any nucleotide
<221> NAME/KEY: misc_feature
<222> LOCATION: (203)
<223> OTHER INFORMATION: n is any nucleotide
<221> NAME/KEY: misc_feature
<222> LOCATION: (229)
<223> OTHER INFORMATION: n is any nucleotide
<221> NAME/KEY: misc_feature
<222> LOCATION: (255)
<223> OTHER INFORMATION: n is any nucleotide
<221> NAME/KEY: misc_feature
<222> LOCATION: (263)
<223> OTHER INFORMATION: n is any nucleotide
<221> NAME/KEY: misc_feature
<222> LOCATION: (273)
<223> OTHER INFORMATION: n is any nucleotide

<400> SEQUENCE: 74
tatcgaagta gccgccgctg cccntgcacg gtggaggagg tggaggcgtt gagctgcggg      60
gcgggcggga ggggcggcgg cggcacgttn agctccgaca gcatgctctc gacccaaaac     120
nacaggtcgg tggggttgta gtgcacggtg tccgtggcga gggggtggcn aanctgtcgt     180 cagggcggc gccngcgccc acnccgccca tccccatggc catctcganc tgctccagct      240
tctgcgccac ttccnccatg tcngatgcgc gcnccttgta cccga                     285

<210> SEQ ID NO 75
<211> LENGTH: 259
<212> TYPE: DNA
<213> ORGANISM: Triticum aestivum
<220> FEATURE:
<221> NAME/KEY: misc_feature
<222> LOCATION: (10)
<223> OTHER INFORMATION: n is any nucleotide
<221> NAME/KEY: misc_feature
<222> LOCATION: (13)
<223> OTHER INFORMATION: n is any nucleotide
<221> NAME/KEY: misc_feature
<222> LOCATION: (17)
<223> OTHER INFORMATION: n is any nucleotide
<221> NAME/KEY: misc_feature
<222> LOCATION: (18)
<223> OTHER INFORMATION: n is any nucleotide
<221> NAME/KEY: misc_feature
<222> LOCATION: (45)
<223> OTHER INFORMATION: n is any nucleotide
<221> NAME/KEY: misc_feature
<222> LOCATION: (48)
<223> OTHER INFORMATION: n is any nucleotide
<221> NAME/KEY: misc_feature
<222> LOCATION: (158)
<223> OTHER INFORMATION: n is any nucleotide
<221> NAME/KEY: misc_feature
<222> LOCATION: (169)
<223> OTHER INFORMATION: n is any nucleotide
<221> NAME/KEY: misc_feature
<222> LOCATION: (205)
<223> OTHER INFORMATION: n is any nucleotide
<221> NAME/KEY: misc_feature
<222> LOCATION: (218)
<223> OTHER INFORMATION: n is any nucleotide
<221> NAME/KEY: misc_feature
<222> LOCATION: (224)
<223> OTHER INFORMATION: n is any nucleotide
<221> NAME/KEY: misc_feature
<222> LOCATION: (231)
<223> OTHER INFORMATION: n is any nucleotide
<221> NAME/KEY: misc_feature
<222> LOCATION: (237)
```

```
<223> OTHER INFORMATION: n is any nucleotide
<221> NAME/KEY: misc_feature
<222> LOCATION: (242)
<223> OTHER INFORMATION: n is any nucleotide
<221> NAME/KEY: misc_feature
<222> LOCATION: (258)
<223> OTHER INFORMATION: n is any nucleotide

<400> SEQUENCE: 75
acggcgcggn ccncgcnngc ttgggagggg atcggccgca gcgcntanat gctgctggag      60
gagtcgacgg agggcgggag atcgaactag ccgccgctgc ccgtgtacgg tggaggaggt     120
ggaggcgttg agctgcgggg cgggcgggag gggcagcngc tgcacgttna gctcccacac     180
cacgtctctc aacccaacca cgacncgtct gtggggtngt aatncacggt ntccctngct     240
angtgggtgg ccaatctnt                                                  259

<210> SEQ ID NO 76
<211> LENGTH: 324
<212> TYPE: DNA
<213> ORGANISM: Triticum aestivum
<220> FEATURE:
<221> NAME/KEY: misc_feature
<222> LOCATION: (158)
<223> OTHER INFORMATION: n is any nucleotide
<221> NAME/KEY: misc_feature
<222> LOCATION: (161)
<223> OTHER INFORMATION: n is any nucleotide
<221> NAME/KEY: misc_feature
<222> LOCATION: (217)
<223> OTHER INFORMATION: n is any nucleotide

<400> SEQUENCE: 76
cacggtgtcc gtggcgaggt gggtggcgaa gctgtcgtcg ggggcggcgc cggcgcccac      60
gccgcccatc cccatggcca tctcgagctg ctccagcttc tgcgccacgt ccgccatgtc     120
ggaggcgcgc accttgtacc cgagcgccgc cagcagcncg nccacctcct cccccctcccc   180 cgccgccgcc gacaccatca tcttgtcctc ggacganccc atgccgccac cgccgccgcc     240
gctccctccg gcgtcctggt actcccgctt catgatccgc gagctacctc gcctctctat     300
ctatctctgg ccaataattg cgca                                            324

<210> SEQ ID NO 77
<211> LENGTH: 408
<212> TYPE: DNA
<213> ORGANISM: Triticum aestivum
<220> FEATURE:
<221> NAME/KEY: misc_feature
<222> LOCATION: (38)
<223> OTHER INFORMATION: n is any nucleotide
<221> NAME/KEY: misc_feature
<222> LOCATION: (108)
<223> OTHER INFORMATION: n is any nucleotide
<221> NAME/KEY: misc_feature
<222> LOCATION: (128)
<223> OTHER INFORMATION: n is any nucleotide
<221> NAME/KEY: misc_feature
<222> LOCATION: (352)
<223> OTHER INFORMATION: n is any nucleotide
<221> NAME/KEY: misc_feature
<222> LOCATION: (353)
<223> OTHER INFORMATION: n is any nucleotide
<221> NAME/KEY: misc_feature
<222> LOCATION: (371)
<223> OTHER INFORMATION: n is any nucleotide
<221> NAME/KEY: misc_feature
<222> LOCATION: (383)
<223> OTHER INFORMATION: n is any nucleotide
<221> NAME/KEY: misc_feature
<222> LOCATION: (385)
```

-continued

```
<223> OTHER INFORMATION: n is any nucleotide

<400> SEQUENCE: 77
gaccaccacc ggcatgtagt aatgtaatcc cttcttcntt cccagttctc caccgcctcc      60
atgatcaccc gtaaaactcc taagccctat tattactact attatgtnta aatgtctatt     120
attgctangt gtaattcctc caaccgctca tatcaaaata agcacgggcc ggactttgtt     180
agcagctcca atgagaatga aatgaatttt gtacgcaagg cacgtccaaa actgggctga     240
gctttgttct gttctgttat gttcatggtg ctcactgctc tgatgaacat gatggtgcct     300
ccaatgggtg gctttgcaat tgttgaacgt tttggcttgg gggacttggt gnntggtgca     360
tgggaatgaa nattccacat ccncnggaat taaaattagc ccatcccg                  408

<210> SEQ ID NO 78
<211> LENGTH: 84
<212> TYPE: PRT
<213> ORGANISM: Arabidopsis thaliana

<400> SEQUENCE: 78

Met Lys Arg Asp His His His His Gln Asp Lys Lys Thr Met Met
 1               5                  10                  15

Met Asn Glu Glu Asp Asp Gly Asn Gly Met Asp Glu Leu Leu Ala Val
                20                  25                  30

Leu Gly Tyr Lys Val Arg Ser Ser Glu Met Ala Asp Val Ala Gln Lys
            35                  40                  45

Leu Glu Gln Leu Glu Val Met Met Ser Asn Val Gln Glu Asp Asp Leu
        50                  55                  60

Ser Gln Leu Ala Thr Glu Thr Val His Tyr Asn Pro Ala Glu Leu Tyr
    65                  70                  75                  80

Thr Trp Leu Asp

<210> SEQ ID NO 79
<211> LENGTH: 87
<212> TYPE: PRT
<213> ORGANISM: Oryza sativa
<220> FEATURE:
<221> NAME/KEY: SITE
<222> LOCATION: (26)
<223> OTHER INFORMATION: Xaa is unknown or other amino acid
<221> NAME/KEY: SITE
<222> LOCATION: (31)
<223> OTHER INFORMATION: Xaa is unknown or other amino acid

<400> SEQUENCE: 79

Glu Ala Gly Gly Ser Ser Gly Gly Gly Ser Ser Ala Asp Met Gly Ser
 1               5                  10                  15

Cys Lys Asp Lys Val Met Ala Gly Ala Xaa Gly Glu Glu Xaa Val
                20                  25                  30

Asp Glu Leu Leu Ala Ala Leu Gly Tyr Lys Val Arg Ser Ser Asp Met
            35                  40                  45

Ala Asp Val Ala Gln Lys Leu Glu Gln Leu Glu Met Ala Met Gly Met
        50                  55                  60

Gly Gly Val Thr Pro Pro Ala Gln Arg Met Thr Gly Ser Cys Arg Thr
    65                  70                  75                  80

Trp Pro Arg Thr Lys Phe Ile
                85

<210> SEQ ID NO 80
<211> LENGTH: 19
```

-continued

```
<212> TYPE: DNA
<213> ORGANISM: Artificial Sequence
<220> FEATURE:
<223> OTHER INFORMATION: Description of Artificial Sequence: Primer

<400> SEQUENCE: 80
ggcgatgaca cggatgacg                                              19

<210> SEQ ID NO 81
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 81
cttgcgcatg gcaccgccct gcgacgaag                                   29

<210> SEQ ID NO 82
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 82
ccagctaata atggcttgcg cgcctcg                                     27

<210> SEQ ID NO 83
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 83
tatcccagaa ccgaaaccga g                                           21

<210> SEQ ID NO 84
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 84
cggcgtcttg gtactcgcgc ttcatg                                      26

<210> SEQ ID NO 85
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 85
tgggctcccg cgccgagtcc gtggac                                      26

<210> SEQ ID NO 86
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 86
```
ctccaagcct cttgcgctga ccgagatcga g            31

<210> SEQ ID NO 87
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 87
tccacaggct caccagtcac caacatcaat c            31

<210> SEQ ID NO 88
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 88
acggtactgg aagtccacgc ggatggtgtg              30

<210> SEQ ID NO 89
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 89
cgcacaccat ccgcgtggac ttccagtac               29

<210> SEQ ID NO 90
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 90
ctcggccggc agatctgcaa cgtggtg                 27

<210> SEQ ID NO 91
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 91
ttgtgacggt ggacgatgtg gacgcgagcc ttg          33

<210> SEQ ID NO 92
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 92
ggacgctgcg acaaaccgtc catcgatcca ac           32

<210> SEQ ID NO 93
<211> LENGTH: 30
<212> TYPE: DNA
<213> ORGANISM: Artificial Sequence

```
<220> FEATURE:
<223> OTHER INFORMATION: Description of Artificial Sequence: Primer

<400> SEQUENCE: 93
tccgaaatca tgaagcgcga gtaccaagac                                        30

<210> SEQ ID NO 94
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 94
tcgggtacaa ggtgcgttcg tcggatatg                                         29

<210> SEQ ID NO 95
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 95
atgaagcgcg agtaccaaga c                                                 21

<210> SEQ ID NO 96
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 96
gtgtgccttg atgcggtcca gaag                                              24

<210> SEQ ID NO 97
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 97
aaccacccct ccctgatcac ggag                                              24

<210> SEQ ID NO 98
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 98
cactaggagc tccgtggtcg aagctg                                            26

<210> SEQ ID NO 99
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 99
gctgcgcaag aagccggtgc agctc                                             25
```

<210> SEQ ID NO 100
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 100
agtacacttc cgacatgact tg                                              22

<210> SEQ ID NO 101
<211> LENGTH: 4
<212> TYPE: PRT
<213> ORGANISM: Zea mays

<400> SEQUENCE: 101

Val Ala Gln Lys
 1

<210> SEQ ID NO 102
<211> LENGTH: 12
<212> TYPE: PRT
<213> ORGANISM: Zea mays

<400> SEQUENCE: 102

Leu Ala Thr Asp Thr Val His Tyr Asn Pro Ser Asp
 1               5                  10

<210> SEQ ID NO 103
<211> LENGTH: 13
<212> TYPE: PRT
<213> ORGANISM: Triticum aestivum

<400> SEQUENCE: 103

Leu Asn Ala Pro Pro Pro Pro Leu Pro Pro Ala Pro Gln
 1               5                  10

<210> SEQ ID NO 104
<211> LENGTH: 17
<212> TYPE: PRT
<213> ORGANISM: Triticum aestivum

<400> SEQUENCE: 104

Asp Glu Leu Leu Ala Ala Leu Gly Tyr Lys Val Arg Ala Ser Asp Met
 1               5                  10                  15
Ala

<210> SEQ ID NO 105
<211> LENGTH: 51
<212> TYPE: DNA
<213> ORGANISM: Triticum aestivum

<400> SEQUENCE: 105
gacgagctgc tggcggcgct cgggtacaag gtgcgcgcct ccgacatggc g              51

<210> SEQ ID NO 106
<211> LENGTH: 17
<212> TYPE: PRT
<213> ORGANISM: Zea mays

<400> SEQUENCE: 106

Asp Glu Leu Leu Ala Ala Leu Gly Tyr Lys Val Arg Ser Ser Asp Met
 1               5                  10                  15

```
Ala

<210> SEQ ID NO 107
<211> LENGTH: 5
<212> TYPE: PRT
<213> ORGANISM: Arabidopsis thaliana

<400> SEQUENCE: 107

Asp Glu Leu Leu Ala
 1               5

<210> SEQ ID NO 108
<211> LENGTH: 4
<212> TYPE: PRT
<213> ORGANISM: Arabidopsis thaliana

<400> SEQUENCE: 108

Glu Gln Leu Glu
 1
```

GENETIC CONTROL OF PLANT GROWTH AND DEVELOPMENT

This is a 371 of PCT/GB98/02383, filed Aug. 7, 1998.

This invention relates to the genetic control of growth and/or development of plants and the cloning and expression of genes involved therein. More particularly, the invention relates to the cloning and expression of the Rht gene of *Triticum Aestivum*, and homologues from other species, and use of the genes in plants.

An understanding of the genetic mechanisms which influence growth and development of plants, including flowering, provides a means for altering the characteristics of a target plant. Species for which manipulation of growth and/or development characteristics may be advantageous includes all crops, with important examples being the cereals, rice and maize, probably the most agronomically important in warmer climatic zones, and wheat, barley, oats and rye in more temperate climates. Important crops for seed products are oil seed rape and canola, maize, sunflower, soyabean and sorghum. Many crops which are harvested for their roots are, of course, grown annually from seed and the production of seed of any kind is very dependent upon the ability of the plant to flower, to be pollinated and to set seed. In horticulture, control of the timing of growth and development, including flowering, is important. Horticultural plants whose flowering may be controlled include lettuce, endive and vegetable brassicas including cabbage, broccoli and cauliflower, and carnations and geraniums. Dwarf plants on the one hand and over-size, taller plants on the other may be advantageous and/or desirable in various horticultural and agricultural contexts, further including trees, plantation crops and grasses.

Recent decades have seen huge increases in wheat grain yields due to the incorporation of semi-dwarfing Rht homeoalleles into breeding programmes. These increases have enabled wheat productivity to keep pace with the demands of the rising world population. Previously, we described the cloning of the *Arabidopsis gai* alleles (International patent application PCT/GB97/00390 filed Feb. 12, 1997 and published as WO97/29123 on Aug. 14, 1998, John Innes Centre Innovations Limited, the full contents of which are incorporated herein by reference) which, like Rht mutant alleles in wheat (a monocot), confers a semi-dominant dwarf phenotype in Arabidopsis (a dicot) and a reduction in responsiveness to the plant growth hormone gibberellin (GA). gai encodes a mutant protein (gai) which lacks a 17 amino acid residue segment found near the N-terminus of the wild-type (GAI) protein. The sequence of this segment is highly conserved in a rice cDNA sequence (EST). Here we show that this cDNA maps to a short section of the overlapping cereal genome maps known to contain the Rht loci, and that we have used the cDNA to isolate the Rht genes of wheat. That genomes as widely diverged as those of Arabidopsis and Triticum should carry a conserved sequence which, when mutated, affects GA responsiveness, indicates a role for that sequence in GA signalling that is conserved throughout the plant kingdom. Furthermore, cloning of Rht permits its transfer to many different crop species, with the aim of yield enhancement as great as that obtained previously with wheat.

The introduction of semi-dwarfing Rht homeoalleles (originally known as Norin 10 genes, derived from a Japanese variety, Norin 10) into elite bread-wheat breeding lines was one of the most significant contributors to the so-called "green revolution" (Gale et al, 1985. Dwarfing genes in wheat. In: Progress in Plant Breeding, G.E. Russell (ed) Butterworths, London pp 1–35). Wheat containing these homeoalleles consistently out-yield wheats lacking them, and now comprise around 80% of the world's wheat crop. The biological basis of this yield-enhancement appears to be two-fold. Firstly, the semi-dwarf phenotype conferred by the Rht alleles causes an increased resistance to lodging (flattening of plants by wind/rain with consequent loss of yield). Secondly, these alleles cause a reallocation of photoassimilate, with more being directed towards the grain, and less towards the stem (Gale et al, 1985). These properties have major effects on wheat yields, as demonstrated by the fact that UK wheat yields increased by over 20% during the years that Rht-containing lines were taken up by farmers.

The rht mutants are dwarfed because they contain a genetically dominant, mutant rht allele which compromises their responses to gibberellin (GA, an endogenous plant growth regulator) (Gale et al, 1976. Heredity 37; 283–289). Thus the coleoptiles of rht mutants, unlike those of wild-type wheat plants, do not respond to GA applications. In addition, rht mutants accumulate biologically active GAs to higher levels than found in wild-type controls (Lenton et al, 1987. Gibberellin insensitivity and depletion in wheat—consequences for development. In: Hormone action in Plant Development—a critical appraisal. G V Haod, J R Lenton, M E Jackson and R K Atkin (eds) Butterworths, London pp 145–160). These properties (genetic dominance, reduced GA-responses, and high endogenous GA levels) are common to the phenotypes conferred by mutations in other species (D8/D9 in maize; gai in Arabidopsis), indicating that these mutant alleles define orthologous genes in these different species, supported further by the observation that D8/D9 and Rht are syntenous loci in the genomes of maize and wheat.

According to a first aspect of the present invention there is provided a nucleic acid molecule comprising a nucleotide sequence encoding a polypeptide with Rht function. The term "Rht function" indicates ability to influence the phenotype of a plant like the Rht gene of Triticum. "Rht function" may be observed phenotypically in a plant as inhibition, suppression, repression or reduction of plant growth which inhibition, suppression, repression or reduction is antagonised by GA. Rht expression tends to confer a dwarf phenotype on a plant which is antagonised by GA.

Overexpression in a plant from a nucleotide sequence encoding a polypeptide with Rht function may be used to confer a dwarf phenotype on a plant which is correctable by treatment with GA.

Also according to an aspect of the present invention there is provided a nucleic acid molecule comprising a nucleotide sequence encoding a polypeptide with ability to confer a rht mutant phenotype upon expression. rht mutant plants are dwarfed compared with wild-type, the dwarfing being GA-insensitive. Herein, "Rht" (capitalised) is used to refer to the wild-type function, while "rht" (uncapitalised) is used to refer to mutant function.

Many plant growth and developmental processes are regulated by specific members of a family of tetracyclic diterpenoid growth factors known as gibberellins (GA) (Hooley, *Plant Mol. Biol.* 26, 1529–1555 (1994)). By gibberellin or GA is meant a diterpenoid molecule with the basic carbon-ring structure shown in FIG. 5 and possessing biological activity, i.e. we refer to biologically active gibberellins.

Biological activity may be defined by one or more of stimulation of cell elongation, leaf senescence or elicitation of the cereal aleurone α-amylase response. There are many standard assays available in the art, a positive result in any one or more of which signals a test gibberellin as biologically active (Hoad et al., *Phytochemistry* 20, 703–713 (1981); Serebryakov et al., *Phytochemistry* 23, 1847–1854 (1984); Smith et al., *Phytochemistry* 33, 17–20 (1993)).

Assays available in the art include the lettuce hypocotyl assay, cucumber hypocotyl assay, and oat first leaf assay, all of which determine biological activity on the basis of ability of an applied gibberellin to cause elongation of the respective tissue. Preferred assays are those in which the test composition is applied to a gibberellin-deficient plant. Such preferred assays include treatment of dwarf GA-deficient Arabidopsis to determine growth, the dwarf pea assay, in which internode elongation is determined, the Tan-ginbozu dwarf rice assay, in which elongation of leaf sheath is determined, and the d5-maize assay, also in which elongation of leaf sheath is determined. The elongation bioassays measure the effects of general cell elongation in the respective organs and are not restricted to particular cell types.

Further available assays include the dock (Rumex) leaf senescence assay and the cereal aleurone α-amylase assay. Aleurone cells which surround the endosperm in grain secrete α-amylase on germination, which digests starch to produce sugars then used by the growing plant. The enzyme production is controlled by GA. Isolated aleurone cells given biologically active GA secrete α-amylase whose activity can then be assayed, for example by measurement of degradation of starch.

Structural features important for high biological activity (exhibited by $GA_1$, $GA_3$, $GA_4$ and $GA_7$) are a carboxyl group on C-6 of B-ring; C-19, C-10 lactone; and β-hydroxylation at C-3. β-hydroxylation at C-2 causes inactivity (exhibited by $GA_8$, $GA_{29}$, $GA_{34}$ and $GA_{51}$). rht mutants do not respond to GA treatment, e.g. treatment with $GA_1$, $GA_3$ or $GA_4$.

Treatment with GA is preferably by spraying with aqueous solution, for example spraying with $10^{-4}$M $GA_3$ or $GA_4$ in aqueous solution, perhaps weekly or more frequently, and may be by placing droplets on plants rather than spraying. GA may be applied dissolved in an organic solvent such as ethanol or acetone, because it is more soluble in these than in water, but this is not preferred because these solvents have a tendency to damage plants. If an organic solvent is to be used, suitable formulations include 24η1 of 0.6, 4.0 or 300 mM $GA_3$ or $GA_4$ dissolved in 80% ethanol. Plants, e.g. Arabidopsis, may be grown on a medium containing GA, such as tissue culture medium (GM) solidified with agar and containing supplementary GA.

Nucleic acid according to the present invention may have the sequence of a wild-type Rht gene of Triticum or be a mutant, derivative, variant or allele of the sequence provided. Preferred mutants, derivatives, variants and alleles are those which encode a protein which retains a functional characteristic of the protein encoded by the wild-type gene, especially the ability for plant growth inhibition, which inhibition is antagonised by GA, or ability to confer on a plant one or more other characteristics responsive to GA treatment of the plant. Other preferred mutants, derivatives, variants and alleles encode a protein which confers a rht mutant phenotype, that is to say reduced plant growth which reduction is insensitive to GA, i.e. not overcome by GA treatment. Changes to a sequence, to produce a mutant, variant or derivative, may be by one or more of addition, insertion, deletion or substitution of one or more nucleotides in the nucleic acid, leading to the addition, insertion, deletion or substitution of one or more amino acids in the encoded polypeptide. Of course, changes to the a nucleic acid which make no difference to the encoded amino acid sequence are included.

A preferred nucleotide sequence for a Rht gene is one which encodes the RHT amino acid sequence shown in FIG. 3b, especially a Rht coding sequence shown in FIG. 3a. A preferred rht mutant lacks part or all of the 17 amino acid sequence underlined in FIG. 3b, and/or part or the sequence DVAQKLEQLE (SEQ ID NO:4), which immediately follows the 17 amino acid sequence underlined in FIG. 3b.

Further preferred nucleotide sequences encode the amino acid sequence shown in any other figure herein, especially a coding sequence shown in a Figure. Further embodiments of the present invention, in all aspects, employ a nucleotide-sequence encoding the amino acid sequence shown in FIG. 6b, 7b, 8b, 9b, 11b, 11d or 12b. Such a coding sequence may be as shown in FIG. 6a, 7a, 8a, 9a, 11a, 11c or 12a.

The present invention also provides a nucleic acid construct or vector which comprises nucleic acid with any one of the provided sequences, preferably a construct or vector from which polypeptide encoded by the nucleic acid sequence can be expressed. The construct or vector is preferably suitable for transformation into a plant cell. The invention further encompasses a host cell transformed with such a construct or vector, especially a plant cell. Thus, a host cell, such as a plant cell, comprising nucleic acid according to the present invention is provided. Within the cell, the nucleic acid may be incorporated within the chromosome. There may be more than one heterologous nucleotide sequence per haploid genome. This, for example, enables increased expression of the gene product compared with endogenous levels, as discussed below.

A construct or vector comprising nucleic acid according to the present invention need not include a promoter or other regulatory sequence, particularly if the vector is to be used to introduce the nucleic acid into cells for recombination into the genome. However, in one aspect the present invention provides a nucleic acid construct comprising a Rht or rht coding sequence (which includes homologues from other than Triticum) joined to a regulatory sequence for control of expression, the regulatory sequence being other than that naturally fused to the coding sequence and preferably of or derived from another gene.

Nucleic acid molecules and vectors according to the present invention may be as an isolate, provided isolated from their natural environment, in substantially pure or homogeneous form, or free or substantially free of nucleic acid or genes of the species of interest or origin other than the sequence encoding a polypeptide able to influence growth and/or development, which may include flowering, eg in *Triticum Aestivum* nucleic acid other than the Rht coding sequence. The term "nucleic acid isolate" encompasses wholly or partially synthetic nucleic acid.

Nucleic acid may of course be double- or single-stranded, cDNA or genomic DNA, RNA, wholly or partially synthetic, as appropriate. Of course, where nucleic acid according to the invention includes RNA, reference to the sequence shown should be construed as encompassing the RNA equivalent, with U substituted for T.

The present invention also encompasses the expression product of any of the nucleic acid sequences disclosed and methods of making the expression product by expression from encoding nucleic acid therefor under suitable conditions in suitable host cells. Those skilled in the art are well able to construct vectors and design protocols for expression and recovery of products of recombinant gene expression. Suitable vectors can be chosen or constructed, containing appropriate regulatory sequences, including promoter sequences, terminator fragments, polyadenylation sequences, enhancer sequences, marker genes and other sequences as appropriate. For further details see, for example, *Molecular Cloning: a Laboratory Manual:* 2nd edition, Sambrook et al, 1989, Cold Spring Harbor Laboratory Press. Transformation procedures depend on the host used, but are well known. Many known techniques and protocols for manipulation of nucleic acid, for example in preparation of nucleic acid constructs, mutagenesis, sequencing, introduction of DNA into cells and gene expression, and analysis of proteins, are described in detail in *Protocols in Molecular Biology*, Second Edition, Ausubel et al. eds., John Wiley & Sons, 1992. Specific procedures and vectors previously used with wide success upon plants are described by Bevan, Nucl. Acids Res. (1984) 12, 8711–8721), and Guerineau and Mullineaux, (1993) Plant transformation and expression vectors. In: Plant Molecular Biology Labfax (Croy RRD ed) Oxford, BIOS Scientific Publishers, pp 121–148. The disclosures of Sambrook et al. and Ausubel et al. and all other documents mentioned herein are incorporated herein by reference.

Expression as a fusion with a polyhistidine tag allows purification of Rht or rht to be achieved using Ni-NTA resin available from QIAGEN Inc. (USA) and DIAGEN GmbH (Germany). See Janknecht et al., *Proc. Natl. Acad. Sci. USA* 88, 8972–8976 (1991) and EP-A-0253303 and EP-A-0282042. Ni-NTA resin has high affinity for histidines with consecutive histidines close to the N- or C-terminus of the protein and so may be used to purifiy histidine-tagged Rht or rht proteins from plants, plant parts or extracts or from recombinant organisms such as yeast or bacteria, e.g. *E. coli*, expressing the protein.

Purified Rht protein, e.g. produced recombinantly by expression from encoding nucleic acid therefor, may be used to raise antibodies employing techniques which are standard in the art. Antibodies and polypeptides comprising antigen-binding fragments of antibodies may be used in identifying homologues from other species as discussed further below.

Methods of producing antibodies include immunising a mammal (eg human, mouse, rat, rabbit, horse, goat, sheep or monkey) with the protein or a fragment thereof. Antibodies may be obtained from immunised animals using any of a variety of techniques known in the art, and might be screened, preferably using binding of antibody to antigen of interest. For instance, Western blotting techniques or immunoprecipitation may be used (Armitage et al, 1992, Nature 357: 80–82). Antibodies may be polyclonal or monoclonal.

As an alternative or supplement to immunising a mammal, antibodies with appropriate binding specificty may be obtained from a recombinantly produced library of expressed immunoglobulin variable domains, eg using lambda bacteriophage or filamentous bacteriophage which display functional immunoglobulin binding domains on their surfaces; for instance see WO92/01047.

Antibodies raised to a Rht, or rht, polypeptide can be used in the identification and/or isolation of homologous polypeptides, and then the encoding genes. Thus, the present invention provides a method of identifying or isolating a polypeptide with Rht function or ability to confer a rht mutant phenotype, comprising screening candidate polypeptides with a polypeptide comprising the antigen-binding domain of an antibody (for example whole antibody or a fragment thereof) which is able to bind an *Triticum Aestivum* Rht or rht polypeptide, or preferably has binding specificity for such a polypeptide, such as having the amino acid sequence shown in FIG. 3b.

Candidate polypeptides for screening may for instance be the products of an expression library created using nucleic acid derived from an plant of interest, or may be the product of a purification process from a natural source.

A polypeptide found to bind the antibody may be isolated and then may be subject to amino acid sequencing. Any suitable technique may be used to sequence the polypeptide either wholly or partially (for instance a fragment of the polypeptide may be sequenced). Amino acid sequence information may be used in obtaining nucleic acid encoding the polypeptide, for instance by designing one or more oligonucleotides (e.g. a degenerate pool of oligonucleotides) for use as probes or primers in hybridisation to candidate nucleic acid, as discussed further below.

A further aspect of the present invention provides a method of identifying and cloning Rht homologues from plant species other than Triticum which method employs a nucleotide sequence derived from any shown in FIG. 2 or FIG. 3a, or other figure herein. Sequences derived from these may themselves be used in identifying and in cloning other sequences. The nucleotide sequence information provided herein, or any part thereof, may be used in a data-base search to find homologous sequences, expression products of which can be tested for Rht function. Alternatively, nucleic acid libraries may be screened using techniques well known to those skilled in the art and homologous sequences thereby identified then tested.

For instance, the present invention also provides a method of identifying and/or isolating a Rht or rht homologue gene, comprising probing candidate (or "target") nucleic acid with nucleic acid which encodes a polypeptide with Rht function or a fragment or mutant, derivative or allele thereof. The candidate nucleic acid (which may be, for instance, cDNA or genomic DNA) may be derived from any cell or organism which may contain or is suspected of containing nucleic acid encoding such a homologue.

In a preferred embodiment of this aspect of the present invention, the nucleic acid used for probing of candidate nucleic acid encodes an amino acid sequence shown in FIG. 3b, a sequence complementary to a coding sequence, or a fragment of any of these, most preferably comprising a nucleotide sequence shown in FIG. 3a.

Alternatively, as discussed, a probe may be designed using amino acid sequence information obtained by sequencing a polypeptide identified as being able to be bound by an antigen-binding domain of an antibody which is able to bind a Rht or rht polypeptide such as one with the Rht amino acid sequence shown in FIG. 3b.

Preferred conditions for probing are those which are stringent enough for there to be a simple pattern with a small number of hybridizations identified as positive which can be investigated further. It is well known in the art to increase stringency of hybridisation gradually until only a few positive clones remain.

As an alternative to probing, though still employing nucleic acid hybridisation, oligonucleotides designed to amplify DNA sequences from Rht genes may be used in PCR or other methods involving amplification of nucleic acid, using routine procedures. See for instance "PCR protocols; A Guide to Methods and Applications", Eds. Innis et al, 1990, Academic Press, New York.

Preferred amino acid sequences suitable for use in the design of probes or PCR primers are sequences conserved (completely, substantially or partly) between Rht genes.

On the basis of amino acid sequence information, oligonucleotide probes or primers may be designed, taking into account the degeneracy of the genetic code, and, where appropriate, codon usage of the organism from which the candidate nucleic acid is derived. In particular, primers and probes may be designed using information on conserved sequences apparent from, for example, FIG. 3 and/or FIG. 4, also FIG. 10.

Where a full-length encoding nucleic acid molecule has not been obtained, a smaller molecule representing part of the full molecule, may be used to obtain full-length clones. Inserts may be prepared for example from partial cDNA clones and used to screen cDNA libraries. The full-length clones isolated may be subcloned into vectors such as expression vectors or vectors suitable for transformation into plants. Overlapping clones may be used to provide a full-length sequence.

The present invention also extends to nucleic acid encoding Rht or a homologue obtainable using a nucleotide sequence derived from FIG. 2 or FIG. 3a, and such nucleic acid obtainable using one or more, e.g. a pair, of primers including a sequence shown in Table 1 (SEQ ID NO:21–SEQ ID NO:55).

Also included within the scope of the present invention are nucleic acid molecules which encode amino acid sequences which are homologues of the polypeptide encoded by Rht of Triticum. A homologue may be from a species other than Triticum.

Homology may be at the nucleotide sequence and/or amino acid sequence level. Preferably, the nucleic acid and/or amino acid sequence shares homology with the sequence encoded by the nucleotide sequence of FIG. 3a, preferably at least about 50%, or 60%, or 70%, or 80% or 85% homology, most preferably at least 90%, 92%, 95% or 97% homology. Nucleic acid encoding such a polypeptide may preferably share with the Triticum Rht gene the ability to confer a particular phenotype on expression in a plant, preferably a phenotype which is GA responsive (i.e. there is a change in a characteristic of the plant on treatment with GA), such as the ability to inhibit plant growth where the inhibition is antagonised by GA. As noted, Rht expression in a plant may affect one or more other characteristics of the plant. A preferred characteristic that may be shared with the Triticum Rht gene is the ability to complement a Rht null mutant phenotype in a plant such as Triticum, such phenotype being resistance to the dwarfing effect of paclobutrazol. The slender mutant of barley maps to a location in the barley genome equivalent to that of Rht in the wheat genome. Such mutant plants are strongly paclobutrazol resistant. The present inventors believe that the slender barley mutant is a null mutant allele of the orthologous gene to wheat Rht, allowing for complementation of the barley mutant with the wheat gene. Ability to complement a slender mutant in barley may be a characteristic of embodiments of the present invention.

Some preferred embodiments of polypeptides according to the present invention (encoded by nucleic acid embodiments according to the present invention) include the 17 amino acid sequence which is underlined in FIG. 3b, or a contiguous sequence of amino acids residues with at least about 10 residues with similarity or identity with the respective corresponding residue (in terms of position) in 17 amino acids which are underlined in FIG. 3b, more preferably 11, 12, 13, 14, 15, 16 or 17 such residues, and/or the sequence DVAQKLEQLE, or a contiguous sequence of amino acids with at least about 5 residues with similarity or identity with the respective corresponding residue (in terms of position) within DVAQKLEQLE, more preferably 6, 7, 8 or 9 such residues. Further embodiments include the 27 amino acid sequence DELLAALGYKVRASDMADVAQKLEQLE (SEQ ID NO:56), or a contiguous sequence of amino acids residues with at least about 15 residues with similarity or identity with the respective corresponding residue (in terms of position) within this sequence, more preferably 16, 17, 18, 19, 20, 21, 22, 23, 24, 25 or 26 such residues.

As is well-understood, homology at the amino acid level is generally in terms of amino acid similarity or identity. Similarity allows for "conservative variation", i.e. substitution of one hydrophobic residue such as isoleucine, valine, leucine or methionine for another, or the substitution of one polar residue for another, such as arginine for lysine, glutamic for aspartic acid, or glutamine for asparagine. Similarity may be as defined and determined by the TBLASTN program, of Altschul et al. (1990) J. Mol. Biol. 215: 403–10, which is in standard use in the art, or more preferably GAP (Program Manual for the Wisconsin Package, Version 8, September 1994, Genetics Computer Group, 575 Science Drive, Madison, USA), which uses the algorithm of Needleman and Wunsch to align sequences. Suitable parameters for GAP include the default parameters, a gap creation penalty=12 and gap extension penalty=4, or gap creation penalty 3.00 and gap extension penalty 0.1. Homology may be over the full-length of the Rht sequence of FIG. 3b, or may more preferably be over a contiguous sequence of 10 amino acids compared with DVAQKLEQLE (SEQ ID NO:4), and/or a contiguous sequence of 17 amino acids, compared with the 17 amino acids underlined in FIG. 3b, and/or a contiguous sequence of 27 amino acids compared with DELLAALGYKVRASDMADVAQKLEQLE (SEQ ID NO:56), or a longer sequence, e.g. about 30, 40, 50 or more amino acids, compared with the amino acid sequence of FIG. 3b and preferably including the underlined 17 amino acids and/or DVAQKLEQLE (SEQ ID NO:4).

At the nucleic acid level, homology may be over the full-length or more preferably by comparison with the 30 nucleotide coding sequence within the sequence of FIG. 3a and encoding the sequence DVAQKLEQLE (SEQ ID NO:4) and/or the 51 nucleotide coding sequence within the sequence of FIG. 3a and encoding the 17 amino acid sequence underlined in FIG. 3b, or a longer sequence, e.g. about, 60, 70, 80, 90, 100, 120, 150 or more nucleotides and preferably including the 51 nucleotide of FIG. 3 which encodes the underlined 17 amino acid sequence of FIG. 3b.

As noted, similarity may be as defined and determined by the TBLASTN program, of Altschul et al. (1990) *J. Mol. Biol.* 215: 403–10, which is in standard use in the art, or the standard program BestFit, which is part of the Wisconsin Package, Version 8, September 1994, (Genetics Computer Group, 575 Science Drive, Madison, Wis., USA, Wisconsin 53711). BestFit makes an optimal alignment of the best segment of similarity between two sequences. Optimal alignments are found by inserting gaps to maximize the number of matches using the local homology algorithm of Smith and Waterman (*Adv. Appl. Math.* (1981) 2: 482–489). Other algorithms include GAP, which uses the Needleman and Wunsch algorithm to align two complete sequences that maximizes the number of matches and minimizes the number of gaps. As with any algorithm, generally the default parameters are used, which for GAP are a gap creation penalty=12 and gap extension penalty=4. The algorithm FASTA (which uses the method of Pearson and Lipman (1988) *PNAS USA* 85: 2444–2448) is a further alternative.

Use of either of the terms "homology" and "homologous" herein does not imply any necessary evolutionary relationship between compared sequences, in keeping for example with standard use of terms such as "homologous recombination" which merely requires that two nucleotide sequences are sufficiently similar to recombine under the appropriate conditions. Further discussion of polypeptides according to the present invention, which may be encoded by nucleic acid according to the present invention, is found below.

The present invention extends to nucleic acid that hybridizes with any one or more of the specific sequences disclosed herein under stringent conditions.

Hybridisation may be determined by probing with nucleic acid and identifying positive hybridisation under suitably stringent conditions (in accordance with known techniques). For probing, preferred conditions are those which are stringent enough for there to be a simple pattern with a small number of hybridisations identified as positive which can be investigated further. It is well known in the art to increase stringency of hybridisation gradually until only a few positive clones remain.

Binding of a probe to target nucleic acid (e.g. DNA) may be measured using any of a variety of techniques at the disposal of those skilled in the art. For instance, probes may be radioactively, fluorescently or enzymatically labelled. Other methods not employing labelling of probe include examination of restriction fragment length polymorphisms, amplification using PCR, RNAase cleavage and allele specific oligonucleotide probing.

Probing may employ the standard Southern blotting technique. For instance DNA may be extracted from cells and digested with different restriction enzymes. Restriction fragments may then be separated by electrophoresis on an agarose gel, before denaturation and transfer to a nitrocellulose filter. Labelled probe may be hybridised to the DNA fragments on the filter and binding determined. DNA for probing may be prepared from RNA preparations from cells by techniques such as reverse-transcriptase-PRC.

Preliminary experiments may be performed by hybridising under low stringency conditions various probes to Southern blots of DNA digested with restriction enzymes. For probing, preferred conditions are those which are stringent enough for there to be a simple pattern with a small number of hybridisations identified as positive which can be investigated further. It is well known in the art to increase stringency of hybridisation gradually until only a few positive clones remain. Suitable conditions would be achieved when a large number of hybridising fragments were obtained while the background hybridisation was low. Using these conditions nucleic acid libraries, e.g. cDNA libraries representative of expressed sequences, may be searched. Those skilled in the art are well able to employ suitable conditions of the desired stringency for selective hybridisation, taking into account factors such as oligonucleotide length and base composition, temperature and so on.

For instance, screening may initially be carried out under conditions, which comprise a temperature of about 37° C. or more, a formamide concentration of less than about 50%, and a moderate to low salt (e.g. Standard Saline Citrate ('SSC')=0.15 M sodium chloride; 0.15 M sodium citrate; pH 7) concentration.

Alternatively, a temperature of about 50° C. or more and a high salt (e.g. 'SSPE'=0.180 mM sodium chloride; 9 mM disodium hydrogen phosphate; 9 mM sodium dihydrogen phosphate; 1 mM sodium EDTA; pH 7.4). Preferably the screening is carried out at about 370° C., a formamide concentration of about 20%, and a salt concentration of about 5×SSC, or a temperature of about 50° C. and a salt concentration of about 2×SSPE. These conditions will allow the identification of sequences which have a substantial degree of homology (similarity, identity) with the probe sequence, without requiring the perfect homology for the identification of a stable hybrid.

Suitable conditions include, e.g. for detection of sequences that are about 80–90% identical, hybridization overnight at 42° C. in 0.25M $Na_2HPO_4$, pH 7.2, 6.5% SDS, 10% dextran sulfate and a final wash at 55° C. in 0.1×SSC, 0.1% SDS. For detection of sequences that are greater than about 90% identical, suitable conditions include hybridization overnight at 65° C. in 0.25M $Na_2HPO_1$ pH 7.2, 6.5% SDS, 10% dextran sulphate and a final wash at 60° C. in 0.1×SSC, 0.1% SDS.

Conditions that may be used to differentiate Rht genes and homologues from others may include the following procedure:

First and second DNA molecules are run on an agarose gel, blotted onto a membrane filter (Sambrook et al, 1989). The filters are incubated in prehybridization solution [6×SSC, 5×Denhart's solution, 20 mM Tris-HCl, 0.1% SDS, 2 mM EDTA, 20 μg/ml Salmon sperm DNA] at 65° C. for 5 hours, with constant shaking. Then, the solution is replaced with 30 ml of the same, containing the radioactively-labelled second DNA (prepared according to standard techniques; see Sambrook et al, 1989), and incubated overnight at 65° C., with constant shaking. The following morning the filters are rinsed (one rinse with 3×SSC-0.1% SDS solution); and then washed: one wash at 65° C., for 25 minutes, with 3×SSC-0.1% SDS solution; and a second wash, at the same temperature and for the same time, with 0.1×SSC-0.1% SDS. Then the radioactive pattern on the filter is recorded using standard techniques (see Sambrook et al, 1989).

If need be, stringency can be increased by increasing the temperature of the washes, and/or reducing or even omitting altogether, the SSC in the wash solution.

(SSC is 150 mM NaCl, 15 mM sodium citrate. 50×Denhart's solution is 1% (w/v) ficoll, 1% polyvinylpyrrolidone, 1% (w/v) bovine serum albumin.)

Homoloques to rht mutants are also provided by the present invention. These may be mutants where the wild-type includes the 17 amino acids underlined in FIG. 3b, or a contiguous sequence of 17 amino acids with at least about 10 (more preferably 11, 12, 13, 14, 15, 16 or 17) which have similarity or identity with the corresponding residue in the 17 amino acid sequence underlined in FIG. 3, but the mutant does not. Similarly, such mutants may be where the wild-type includes DVAQKLEQLE or a contiguous sequence of 10 amino acids with at least about 5 (more preferably 6, 7, 8 or 9) which have similarity or identity with the corresponding residue in the sequence DVAQKLEQLE, but the mutant does not. Nucleic acid encoding such mutant polypeptides may on expression in a plant confer a phenotype which is insensitive or unresponsive to treatment of the plant with GA, that is a mutant phenotype which is not overcome or there is no reversion to wild-type phenotype on treatment of the plant with GA (though there may be some response in the plant on provision or depletion of GA).

A further aspect of the present invention provides a nucleic acid isolate having a nucleotide sequence encoding a polypeptide which includes an amino acid sequence which is a mutant, allele, derivative or variant sequence of the Rht amino acid sequence of the species *Triticum Aestivum* shown in FIG. 3b, or is a homologue of another species or a mutant, allele, derivative or variant thereof, wherein said mutant, allele, derivative, variant or homologue differs from the amino acid sequence shown in FIG. 3b by way of insertion, deletion, addition and/or substitution of one or more amino acids, as obtainable by producing transgenic plants by transforming plants which have a Rht null mutant phenotype, which phenotype is resistance to the dwarfing effect of paclobutrazol, with test nucleic acid, causing or allowing expression from test nucleic acid within the transgenic plants, screening the transgenic plants for those exhibiting complementation of the Rht null mutant phenotype to identify test nucleic acid able to complement the Rht null mutant, deleting from nucleic acid so identified as being able to complement the Rht null mutant a nucleotide sequence encoding the 17 amino acid sequence underlined in FIG. 3b or a contiguous 17 amino acid sequence in which at least 10 residues have similarity or identity with the respective amino acid in the corresponding position in the 17 amino acid sequence underlined in FIG. 3b, more preferably 11, 12, 13, 5 14, 15, 16 or 17, and/or a nucleotide sequence encoding DVAQKLEQLE or a contiguous sequence of 10 amino aicds with at least about 5 (more preferably 6, 7, 8 or 9) which have similarity or identity with the corresponding residue in the sequence DVAQKLEQLE.

A cell containing nucleic acid of the present invention represents a further aspect of the invention, particularly a plant cell, or a bacterial cell.

The cell may comprise the nucleic acid encoding the protein by virtue of introduction into the cell or an ancestor thereof of the nucleic acid, e.g. by transformation using any suitable technique available to those skilled in the art.

Also according to the invention there is provided a plant cell having incorporated into its genome nucleic acid as disclosed.

Where a complete naturally occurring sequence is employed the plant cell may be of a plant other than the natural host of the sequence.

The present invention also provides a plant comprising such a plant cell.

Also according to the invention there is provided a plant cell having incorporated into its genome a sequence of nucleotides as provided by the present invention, under operative control of a regulatory sequence for control of expression. A further aspect of the present invention provides a method of making such a plant cell involving introduction of a vector comprising the sequence of nucleotides into a plant cell and causing or allowing recombination between the vector and the plant cell genome to introduce the sequence of nucleotides into the genome.

A plant according to the present invention may be one which does not breed true in one or more properties. Plant varieties may be excluded, particularly registrable plant varieties according to Plant Breeders' Rights. It is noted that a plant need not be considered a "plant variety" simply because it contains stably within its genome a transgene, introduced into a cell of the plant or an ancestor thereof.

In addition to a plant, the present invention provides any clone of such a plant, seed, selfed or hybrid progeny and descendants, and any part of any of these, such as cuttings, seed. The invention provides any plant propagule, that is any part which may be used in reproduction or propagation, sexual or asexual, including cuttings, seed and so on. Also encompassed by the invention is a plant which is a sexually or asexually propagated off-spring, clone or descendant of such a plant, or any part or propagule of said plant, off-spring, clone or descendant.

The invention further provides a method of influencing the characteristics of a plant comprising expression of a heterologous Rht or rht gene sequence (or mutant, allele, derivative or homologue thereof, as discussed) within cells of the plant. The term "heterologous" indicates that the gene/sequence of nucleotides in question have been introduced into said cells of the plant, or an ancestor thereof, using genetic engineering, that is to say by human intervention, which may comprise transformation. The gene may be on an extra-genomic vector or incorporated, preferably stably, into the genome. The heterologous gene may replace an endogenous equivalent gene, ie one which normally performs the same or a similar function in control of growth and/or development, or the inserted sequence may be additional to an endogenous gene. An advantage of introduction of a heterologous gene is the ability to place expression of the gene under the control of a promoter of choice, in order to be able to influence gene expression, and therefore growth and/or development of the plant according to preference. Furthermore, mutants and derivatives of the wild-type gene may be used in place of the endogenous gene. The inserted gene may be foreign or exogenous to the host cell, e.g. of another plant species.

The principal characteristic which may be altered using the present invention is growth.

According to the model of the Rht gene as a growth repressor, under-expression of the gene may be used to promote growth, at least in plants which have only one endogenous gene conferring Rht function (not for example Arabidopsis which has endogenous homologues which would compensate). This may involve use of anti-sense or sense regulation. Taller plants may be made by knocking out Rht or the relevant homologous gene in the plant of interest. Plants may be made which are resistant to compounds which inhibit GA biosynthesis, such as paclobutrazol, for instance to allow use of a GA biosynthesis inhibitor to keep weeds dwarf but let crop plants grow tall.

Over-expression of a Rht gene may lead to a dwarf plant which is correctable by treatment with GA, as predicted by the Rht repression model.

Since rht mutant genes are dominant on phenotype, they may be used to make GA-insensitive dwarf plants. This may be applied for example to any transformable crop-plant, tree or fruit-tree species. It may provide higher yield/reduced lodging like Rht wheat. In rice this may provide GA-insensitive rice resistant to the Bakane disease, which is a problem in Japan and elsewhere. Dwarf ornamentals may be of value for the horticulture and cut-flower markets. Sequence manipulation may provide for varying degrees of severity of dwarfing, GA-insensitive phenotype, allowing tailoring of the degree of severity to the needs of each crop-plant or the wishes of the manipulator. Over-expression of rht-mutant sequences is potentially the most useful.

A second characteristic that may be altered is plant development, for instance flowering. In some plants, and in certain environmental conditions, a GA signal is required for floral induction. For example, GA-deficient mutant Arabidopsis plants grown under short day conditions will not flower unless treated with GA: these plants do flower normally when grown under long day conditions. *Arabidopsis gai* mutant plants show delayed flowering under short day conditions: severe mutants may not flower at all. Thus, for instance by Rht or rht gene expression or over-expression, plants may be produced which remain vegetative until given GA treatment to induce flowering. This may be useful in horticultural contexts or for spinach, lettuce and other crops where suppression of bolting is desirable.

The nucleic acid according to the invention may be placed under the control of an externally inducible gene promoter to place the Rht or rht coding sequence under the control of the user.

The term "inducible" as applied to a promoter is well understood by those skilled in the art. In essence, expression under the control of an inducible promoter is "switched on" or increased in response to an applied stimulus. The nature of the stimulus varies between promoters. Some inducible promoters cause little or undetectable levels of expression (or no expression) in the absence of the appropriate stimulus. Other inducible promoters cause detectable constitutive expression in the absence of the stimulus. Whatever the level of expression is in the absence of the stimulus, expression from any inducible promoter is increased in the presence of the correct stimulus. The preferable situation is where the level of expression increases upon application of the relevant stimulus by an amount effective to alter a phenotypic characteristic. Thus an inducible (or "switchable") promoter may be used which causes a basic level of expression in the absence of the stimulus which level is too low to bring about a desired phenotype (and may in fact be zero). Upon application of the stimulus, expression is increased (or switched on) to a level which brings about the desired phenotype.

Suitable promoters include the Cauliflower Mosaic Virus 35S (CaMV 35S) gene promoter that is expressed at a high level in virtually all plant tissues (Benfey et al, 1990a and 1990b); the maize glutathione-S-transferase isoform II (GST-II-27) gene promoter which is activated in response to application of exogenous safener (WO93/01294, ICI Ltd); the cauliflower meri 5 promoter that is expressed in the vegetative apical meristem as well as several well localised positions in the plant body, eg inner phloem, flower primordia, branching points in root and shoot (Medford, 1992; Medford et al, 1991) and the *Arabidopsis thaliana* LEAFY promoter that is expressed very early in flower development (Weigel et al, 1992).

The GST-II-27 gene promoter has been shown to be induced by certain chemical compounds which can be applied to growing plants. The promoter is functional in both monocotyledons and dicotyledons. It can therefore be used to control gene expression in a variety of genetically modified plants, including field crops such as canola, sunflower, tobacco, sugarbeet, cotton; cereals such as wheat, barley, rice, maize, sorghum; fruit such as tomatoes, mangoes, peaches, apples, pears, strawberries, bananas, and melons; and vegetables such as carrot, lettuce, cabbage and onion. The GST-II-27 promoter is also suitable for use in a variety of tissues, including roots, leaves, stems and reproductive tissues.

Accordingly, the present invention provides in a further aspect a gene construct comprising an inducible promoter operatively linked to a nucleotide sequence provided by the present invention, such as the Rht gene of Triticum a homologue from another plant species or any mutant, derivative or allele thereof. This enables control of expression of the gene. The invention also provides plants transformed with said gene construct and methods comprising introduction of such a construct into a plant cell and/or induction of expression of a construct within a plant cell, by application of a suitable stimulus, an effective exogenous inducer. The promoter may be the GST-II-27 gene promoter or any other inducible plant promoter.

When introducing a chosen gene construct into a cell, certain considerations must be taken into account, well known to those skilled in the art. The nucleic acid to be inserted should be assembled within a construct which contains effective regulatory elements which will drive transcription. There must be available a method of transporting the construct into the cell. Once the construct is within the cell membrane, integration into the endogenous chromosomal material either will or will not occur. Finally, as far as plants are concerned the target cell type must be such that cells can be regenerated into whole plants.

Selectable genetic markers may be used consisting of chimaeric genes that confer selectable phenotypes such as resistance to antibiotics such as kanamycin, hygromycin, phosphinotricin, chlorsulfuron, methotrexate, gentamycin, spectinomycin, imidazolinones and glyphosate.

An aspect of the present invention is the use of nucleic acid according to the invention in the production of a transgenic plant.

A further aspect provides a method including introducing the nucleic acid into a plant cell and causing or allowing incorporation of the nucleic acid into the genome of the cell.

Any appropriate method of plant transformation may be used to generate plant cells comprising nucleic acid in accordance with the present invention. Following transformation, plants may be regenerated from transformed plant cells and tissue.

Successfully transformed cells and/or plants, i.e. with the construct incorporated into their genome, may be selected following introduction of the nucleic acid into plant cells, optionally followed by regeneration into a plant, e.g. using one or more marker genes such as antibiotic resistance (see above).

Plants transformed with the DNA segment containing the sequence may be produced by standard techniques which are already known for the genetic manipulation of plants. DNA can be transformed into plant cells using any suitable technology, such as a disarmed Ti-plasmid vector carried by Agrobacterium exploiting its natural gene transfer ability (EP-A-270355, EP-A-0116718, NAR 12(22) 8711–87215 1984), particle or microprojectile bombardment (U.S. Pat. No. 5100792, EP-A-444882, EP-A-434616) microinjection (WO 92/09696, WO 94/00583, EP 331083, EP 175966, Green et al. (1987) *Plant Tissue* and *Cell Culture*, Academic Press), electroporation (EP 290395, WO 8706614 Gelvin Debeyser—see attached) other forms of direct DNA uptake (DE 4005152, WO 9012096, U.S. Pat. No. 4,684,611), liposome mediated DNA uptake (e.g. Freeman et al. *Plant Cell Physiol.* 29: 1353 (1984)), or the vortexing method (e.g. Kindle, *PNAS U.S.A.* 87: 1228 (1990d). Physical methods for the transformation of plant cells are reviewed in Oard, 1991, *Biotech. Adv.* 9: 1–11.

Agrobacterium transformation is widely used by those skilled in the art to transform dicotyledonous species. Recently, there has been substantial progress towards the routine production of stable, fertile transgenic plants in almost all economically relevant monocot plants (Toriyama, et al. (1988) *Bio/Technology* 6, 1072–1074; Zhang, et al. (1988) *Plant Cell Rep.* 7, 379–384; Zhang, et al. (1988) *Theor Appl Genet* 76, 835–840; Shimamoto, et al. (1989) *Nature* 338, 274–276; Datta, et al. (1990) *Bio/Technology* 8, 736–740; Christou, et al. (1991) *Bio/Technology* 9, 957–962; Peng, et al. (1991) International Rice Research Institute, Manila, Philippines 563–574; Cao, et al. (1992) *Plant Cell Rep.* 11, 585–591; Li, et al. (1993) *Plant Cell Rep.* 12, 250–255; Rathore, et al. (1993) *Plant Molecular Biology* 21, 871–884; Fromm, et al. (1990) *Bio/Technology* 8, 833–839; Gordon-Kamm, et al. (1990) *Plant Cell* 2, 603–618; D'Halluin, et al. (1992) *Plant Cell* 4, 1495–1505; Walters, et al. (1992) *Plant Molecular Biology* 18, 189–200; Koziel, et al. (1993) *Biotechnology* 11, 194–200; Vasil, I. K. (1994) *Plant Molecular Biology* 25, 925–937; Weeks, et al. (1993) *Plant Physiology* 102, 1077–1084; Somers, et al. (1992) *Bio/Technology* 10, 1589–1594; WO92/14828). In particular, Agrobacterium mediated transformation is now emerging also as an highly efficient transformation method in monocots (Hiei et al. (1994) *The Plant Journal* 6, 271–282).

The generation of fertile transgenic plants has been achieved in the cereals rice, maize, wheat, oat, and barley (reviewed in Shimamoto, K. (1994) *Current Opinion in Biotechnology* 5, 158–162.; Vasil, et al. (1992) *Bio/Technology* 10, 667–674; Vain et al., 1995, *Biotechnology Advances* 13 (4): 653–671; Vasil, 1996, *Nature Biotechnology* 14 page 702).

Microprojectile bombardment, electroporation and direct DNA uptake are preferred where Agrobacterium is inefficient or ineffective. Alternatively, a combination of different techniques may be employed to enhance the efficiency of the transformation process, eg bombardment with Agrobacterium coated microparticles (EP-A-486234) or microprojectile bombardment to induce wounding followed by co-cultivation with Agrobacterium (EP-A-486233).

*Brassica napus* transformation is described in Moloney et al. (1989) *Plant Cell Reports* 8: 238–242.

Following transformation, a plant may be regenerated, e.g. from single cells, callus tissue or leaf discs, as is standard in the art. Almost any plant can be entirely regenerated from cells, tissues and organs of the plant. Available techniques are reviewd in Vasil et al., *Cell Culture and Somatic Cel Genetics of Plants*, Vol I, II and III, *Laboratory Procedures and Their Applications*, Academic Press, 1984, and Weissbach and Weissbach, *Methods for Plant Molecular Biology*, Academic Press, 1989.

The particular choice of a transformation technology will be determined by its efficiency to transform certain plant species as well as the experience and preference of the person practising the invention with a particular methodology of choice. It will be apparent to the skilled person that the particular choice of a transformation system to introduce nucleic acid into plant cells is not essential to or a limitation of the invention, nor is the choice of technique for plant regeneration.

In the present invention, over-expression may be achieved by introduction of the nucleotide sequence in a sense orientation. Thus, the present invention provides a method of influencing a characteristic of a plant, the method comprising causing or allowing expression of nucleic acid according to the invention from that nucleic acid within cells of the plant.

Under-expression of the gene product polypeptide may be achieved using anti-sense technology or "sense regulation". The use of anti-sense genes or partial gene sequences to down-regulate gene expression is now well-established. DNA is placed under the control of a promoter such that transcription of the "anti-sense" strand of the DNA yields RNA which is complementary to normal mRNA transcribed from the "sense" strand of the target gene. For double-stranded DNA this is achieved by placing a coding sequence or a fragment thereof in a "reverse orientation" under the control of a promoter. The complementary anti-sense RNA sequence is thought then to bind with mRNA to form a duplex, inhibiting translation of the endogenous mRNA from the target gene into protein. Whether or not this is the actual mode of action is still uncertain. However, it is established fact that the technique works. See, for example, Rothstein et al, 1987; Smith et al, (1988) *Nature* 334, 724–726; Zhang et al, (1992) *The Plant Cell* 4, 1575–1588, English et al., (1996) *The Plant Cell* 8, 179–188. Antisense technology is also reviewed in reviewed in Bourque, (1995), *Plant Science* 105, 125–149, and Flavell, (1994) *PNAS USA* 91, 3490–3496.

The complete sequence corresponding to the coding sequence in reverse orientation need not be used. For example fragments of sufficient length may be used. It is a routine matter for the person skilled in the art to screen fragments of various sizes and from various parts of the coding sequence to optimise the level of anti-sense inhibition. It may be advantageous to include the initiating methionine ATG codon, and perhaps one or more nucleotides upstream of the initiating codon. A further possibility is to target a regulatory sequence of a gene, e.g. a sequence that is characteristic of one or more genes in one or more pathogens against which resistance is desired. A suitable fragment may have at least about 14–23 nucleotides, e.g. about 15, 16 or 17, or more, at least about 25, at least about 30, at least about 40, at least about 50, or more. Other fragments may be at least about 300 nucleotides, at least about 400 nucleotides, at least about 500 nucleotides, at least about 600 nucleotides, at least about 700 nucleotides or more. Such fragments in the sense orientation may be used in co-suppression (see below).

Total complementarity of sequence is not essential, though may be preferred. One or more nucleotides may differ in the anti-sense construct from the target gene. It may be preferred for there to be sufficient homology for the respective anti-sense and sense RNA molecules to hybridise, particularly under the conditions existing in a plant cell.

Thus, the present invention also provides a method of influencing a characteristic of a plant, the method comprising causing or allowing anti-sense transcription from nucleic acid according to the invention within cells of the plant.

When additional copies of the target gene are inserted in sense, that is the same, orientation as the target gene, a range of phenotypes is produced which includes individuals where over-expression occurs and some where under-expression of protein from the target gene occurs. When the inserted gene is only part of the endogenous gene the number of under-expressing individuals in the transgenic population increases. The mechanism by which sense regulation occurs, particularly down-regulation, is not well-understood. However, this technique is also well-reported in scientific and patent literature and is used routinely for gene control. See, for example, See, for example, van der Krol et al., (1990) *The Plant Cell* 2, 291–299; Napoli et al., (1990) *The Plant Cell* 2, 279–289; Zhang et al., (1992) *The Plant Cell* 4, 1575–1588, and U.S. Pat. No. 5,231,020.

Thus, the present invention also provides a method of influencing a characteristic of a plant, the method comprising causing or allowing expression from nucleic acid according to the invention within cells of the plant. This may be used to influence growth.

Aspects and embodiments of the present invention will now be illustrated, by way of example, with reference to the accompanying figures. Further aspects and embodiments will be apparent to those skilled in the art. All documents mentioned in this text are incorporated herein by reference.

BRIEF DESCRIPTION OF THE DRAWING

FIG. 1: Alignment of N-terminus predicted GAI amino acid sequence (Gai) (SEQ ID NO:78) with rice EST D39460 (0830) (SEQ ID NO:79), with a region of homology outlined in black.

FIGS. 2*a*–2*c*. DNA sequences from C15-1, 14a1 and 5a1:

FIG. 2*a* shows a consensus DNA sequence cDNA C15-1 (obtained via single-pass sequencing) (SEQ ID NO:57).

FIG. 2*b* shows data from original DNA sequencing runs from 14a1 (single-pass) (SEQ ID NO:58–SEQ ID NO:70).

FIG. 2*c* shows data from original DNA sequencing runs from 5a1 (single-pass) (SEQ ID NO:71–SEQ ID NO:77).

FIGS. 3*a* and 3*b*. Rht sequences:

FIG. 3*a* shows a composite DNA sequence of wheat Rht gene derived from data in FIG. 2, including coding sequence (SEQ ID NO:3).

FIG. 3b shows an alignment of the entire predicted Rht protein sequence encoded by the coding sequence of FIG. 2 (rht) with the entire predicted GAI protein sequence of Arabidopsis (Gai) (SEQ ID NO:1 and SEQ ID NO:2). Regions of sequence identity are highlighted in black.

FIGS. 4a and 4b. D39460 sequence:

FIG. 4a shows DNA sequence (single-pass) of rice cDNA D39460 (SEQ ID NO:19). This cDNA is an incomplete, partial clone, missing the 3' end of the mRNA from which it is derived.

FIG. 4b shows alignment of the entire predicted Rht protein sequence (wheat—encoded by the coding sequence of FIG. 2) with that of GAI (Gai) and rice protein sequence predicted from DNA sequence in FIG. 4a (Rice) (SEQ ID NO:20). Regions of amino acid identity are highlighted in black; some conservative substitutions are shaded.

FIGS. 6a and 6b. Rice EST sequence:

FIG. 6a shows the nucleotide sequence of rice EST D39460, as determined by the present inventors (SEQ ID NO:12).

FIG. 6b shows the predicted amino acid sequence (SEQ ID NO:5) encoded by the rice EST sequence of FIG. 6a.

FIGS. 7a and 7b. Wheat C15-1 cDNA:

FIG. 7a shows the nucleotide sequence of the wheat C15-1 cDNA (SEQ ID NO:13).

FIG. 7b shows the predicted amino acid sequence (SEQ ID NO:6) of the wheat C15-1 cDNA of FIG. 7a.

FIGS. 8a and 8b. Wheat 5a1 genomic clone:

FIGS. 9a and 9b. Maize 1a1 genomic clone:

FIG. 9a shows the nucleotide sequence of the 1a1 maize genomic clone, i.e. D8 (SEQ ID NO:15).

FIG. 9b shows the amino acid sequence (SEQ ID NO:8) of the maize 1a1 genomic clone of FIG. 9a.

FIGS. 10a and 10b shows a PRETTYBOX alignment of amino acid sequences of the maize D8 polypeptide with, the wheat Rht polypeptide the rice EST sequence determined by the present inventors and the *Arabidopsis thaliana* Gai polypeptide.

FIGS. 11a–11d. Sequences of maize D8 alleles:

FIG. 11a shows a partial nucleotide sequence of the maize D8-1allele (SEQ ID NO: 16).

FIG. 11b shows a partial amino acid sequence (SEQ ID NO:9) of the maize D8-1 allele.

FIG. 11c shows a partial nucleotide sequence of the maize D8-2023 allele (SEQ ID NO:17).

FIG. 11d shows a partial amino acid sequence (SEQ ID NO:10) of the maize D8-2023 allele.

FIGS. 12a and 12b. Wheat rht-10 allele:

FIG. 12a shows a partial nucleotide sequence of the wheat rht-10 allele (SEQ ID NO:18).

FIG. 12b shows a partial amino acid sequence (SEQ ID NO:11) of the wheat rht-10 allele.

Figure 5:
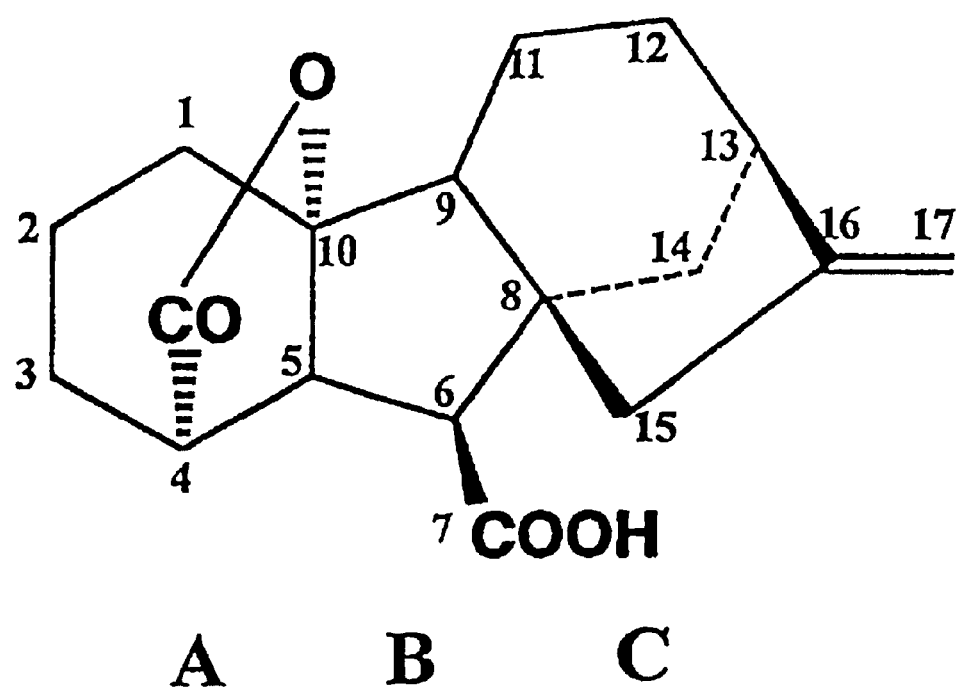
FIG. 5: The basic carbon-ring structure kof gibberellins.

Previously, we cloned the GAI gene of Arabidopsis (PCT/GB97/00390—WO97/29123 published Aug. 14, 1997). Comparison of the DNA sequences of the wild-type (GAI) and mutant (gai) alleles showed that gai encodes a mutant predicted protein product (gai) which lacks a segment of 17 amino acids from close to the N-terminus of the protein. Screening of the DNA sequence databases with the GAI sequence revealed the existence of a rice EST (D39460) which contains a region of sequence very closely related to that of the segment that is deleted from GAI in the gai protein. A comparison of the predicted amino acid sequences from the region DELLA (SEQ ID NO:107) to EQLE (SEQ ID NO:108) are identical in both sequences. The two differences (V/A; E/D) are conservative substitutions, in which one amino acid residue is replaced by another having very similar chemical properties. In addition, the region of identity extends beyond the boundary of the deletion region in the gai protein. The sequence DVAQKLEQLE is not affected by the deletion in gai, and yet is perfectly conserved between the GAI and D39460 sequences (FIG. 1).

An approximately 700 bp SalI-NotI subfragment of D39460 was used in low-stringency hybridization experiments to isolate hybridizing clones from wheat cDNA and genomic libraries (made from DNA from the variety Chinese Spring) and from a maize genomic library (made from line B73N). Several wheat clones were isolated, including C15-1 and C15-10 (cDNAs), and 5a1 and 14a1 (genomic clones). Clone C15-1 has been used in gene mapping experiments. Nullisomic-tetrasomic analysis showed that clone C15-1 hybridizes to genomic DNA fragments derived from wheat chromosomes 4A, 4B and 4D. This is consistent with clone C15-1 containing Rht sequence, since the Rht loci map to the group 4 chromosomes. Furthermore, recombinant analysis using a population segregating for the Rht-D1b (formerly Rht2) allele identified a hybridizing fragment that displayed perfect co-segregation with the mutant allele. This placed the genomic location of the gene encoding the mRNA sequence in cDNA C15-l within a 2 cM segment (that was already known to contain Rht) of the group 4 chromosomes, and provides strong evidence that the cDNA and genomic clones do indeed contain the Rht gene. The maize D8 DNA sequence disclosed herein is from subcloned contiguous 1.8 kb and 3.0 kb SalI fragments (cloned into Bluescript™ SK+) from 1a1. The wheat Rht sequence disclosed herein is from a 5.7 kb DraI subfragment cloned into Bluescript™ SK+) from clone 5a1.

Figure 4B:
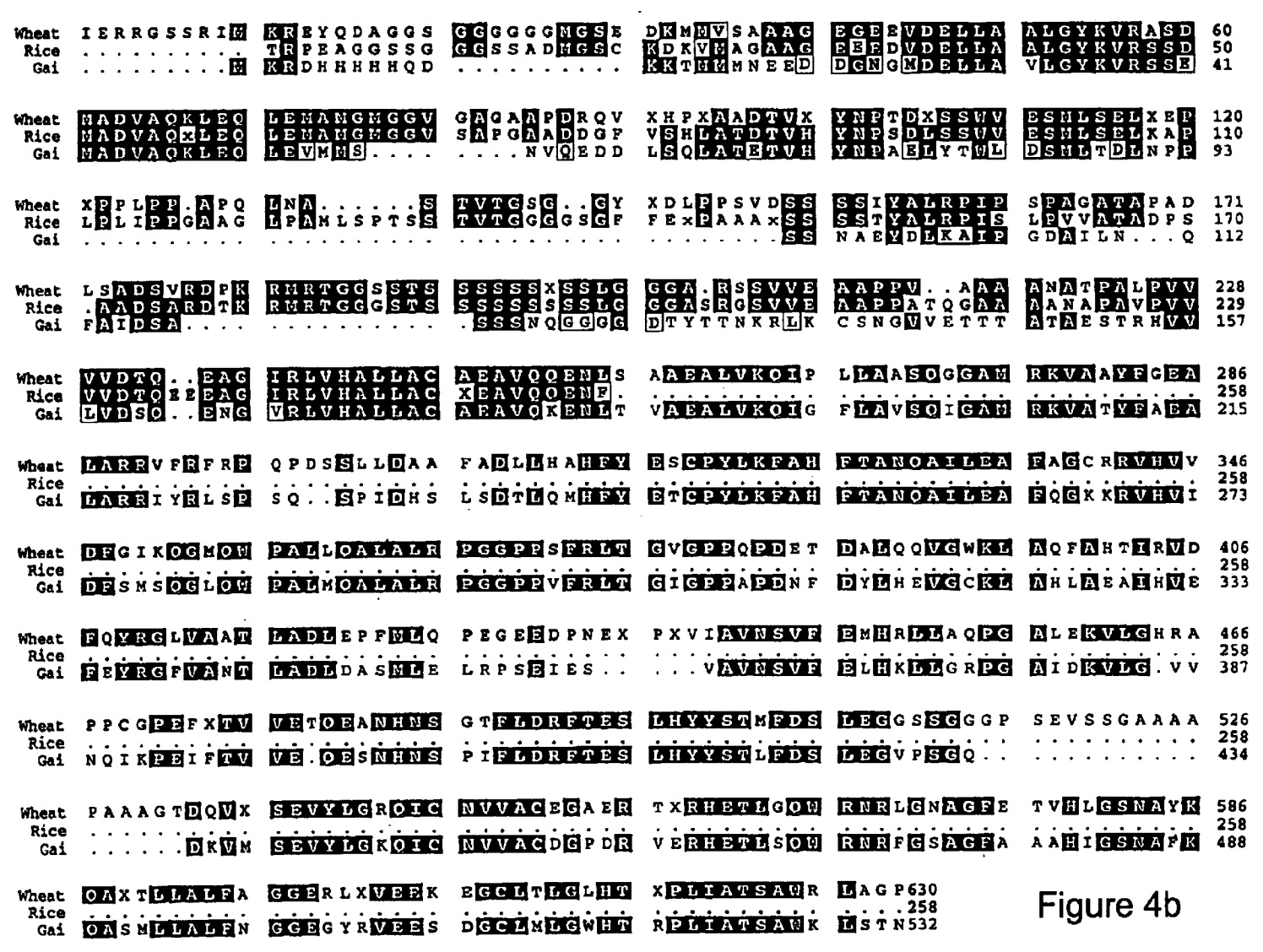

FIG. 2a gives the complete (single-pass) DNA sequence of cDNA C15-1. We have also obtained DNA sequence for C15-10; it is identical with that of C15-1, and is therefore not shown. FIGS. 2b and 2c show original data from individual sequencing runs from clones 14a1 and 5a1. The sequences shown in FIG. 2 can be overlapped to make a composite DNA sequence, shown in FIG. 3a. This sequence displays strong homology with that of Arabidopsis GAI, as revealed by a comparison of the amino acid sequence of a predicted translational product of the wheat sequence (Rht) with that of GAI (GAI), shown in FIG. 3b. In particular, the predicted amino acid sequence of the presumptive Rht reveals a region of near-identity with GAI over the region that is missing in gai (FIG. 4). FIG. 4 reveals that the homology that extends beyond the gai deletion region in the rice EST is also conserved in Rht (DVAQKLEQLE (SEQ ID NO:4)), thus indicating that this region, in addition to that found in the gai deletion, is involved in GA signal-transduction. This region is not found in SCR, another protein that is related in sequence to GAI but which is not involved in GA signalling. The primers used in the above sequencing experiments are shown in Table 1.

Further confirmation that these sequences are indeed the wheat Rht and maize D8 loci has been obtained by analysis of gene sequences from various mutant alleles, as follows.

The present inventors obtained and sequenced the clone identified on the database as the rice EST D39460, and the nucleotide and predicted amino acid sequences resulting from that work are shown in FIG. 6a and FIG. 6b respectively.

Previous work on the GAI gene of Arabidopsis showed that the GAI protein consists of two sections, an N-terminal half displaying no homology with any protein of known function, and a C-terminal half displaying extensive homology with the Arabidopsis SCR candidate transcription factor (Peng et al. (1997) *Genes and Development* 11: 3194–3205; PCT/GB97/00390). As described above, deletion of a portion of the N-terminal half of the protein causes the reduced GA-responses characteristic of the gai mutant allele (Peng et al., 1997; PCT/GB97/00390). The inventors therefore predicted that if D8 and Rht are respectively maize and wheat functional homologues (orthologues) of Arabidopsis GAI, then dominant mutant alleles of D8 and Rht should also contain mutations affecting the N-terminal sections of the proteins that they encode.

Previous reports describe a number of dominant mutant alleles at D8 and at Rht, in particular D8-1, D8-2023 and Rht-D1c (formerly Rht10) (Börner et al. (1996) *Euphytica* 89: 69–75; Harberd and Freeling (1989) *Genetics* 121: 827–838; Winkler and Freeling (1994) *Planta* 193: 341–348). The present inventors therefore cloned the candidate D8/Rht genes from these mutants, and examined by DNA sequencing the portion of the gene that encodes the N-terminal half of the protein.

A fragment of the candidate D8 or Rht genes that encodes a portion of the N-terminal half of the D8/Rht protein was amplified via PCR from genomic DNA of plants containing D8-1, D8-2023 and Rht-D1c, using the following primers for amplification: for D8-1, primers ZM-15 and ZM-24; for D8-2023, primers ZM-9 and ZM-11; for Rht-D1c, nested PCR was performed using Rht-15 and Rht-26 followed by Rht-16 and Rha-2. PCR reactions were performed using a Perkin Elmer geneAmp XL PCR kit, using the following conditions: reactions were incubated at 94° C. for 1 min, then subjected to 13 cycles of 94° C., 15 sec–x° C. for 15 sec–69° C. 5 min (where x is reduced by 1° C. per cycle starting at 64° C. and finishing at 52° C.), then 25 cycles of 94° C., 15 sec–53° C., 15 sec–65° C., 5 min, then 10 min at 70° C. These fragments were then cloned into the pGEM$^R$-T Easy vector (Promega, see Technical Manual), and their DNA sequences were determined.

Figure 10A:
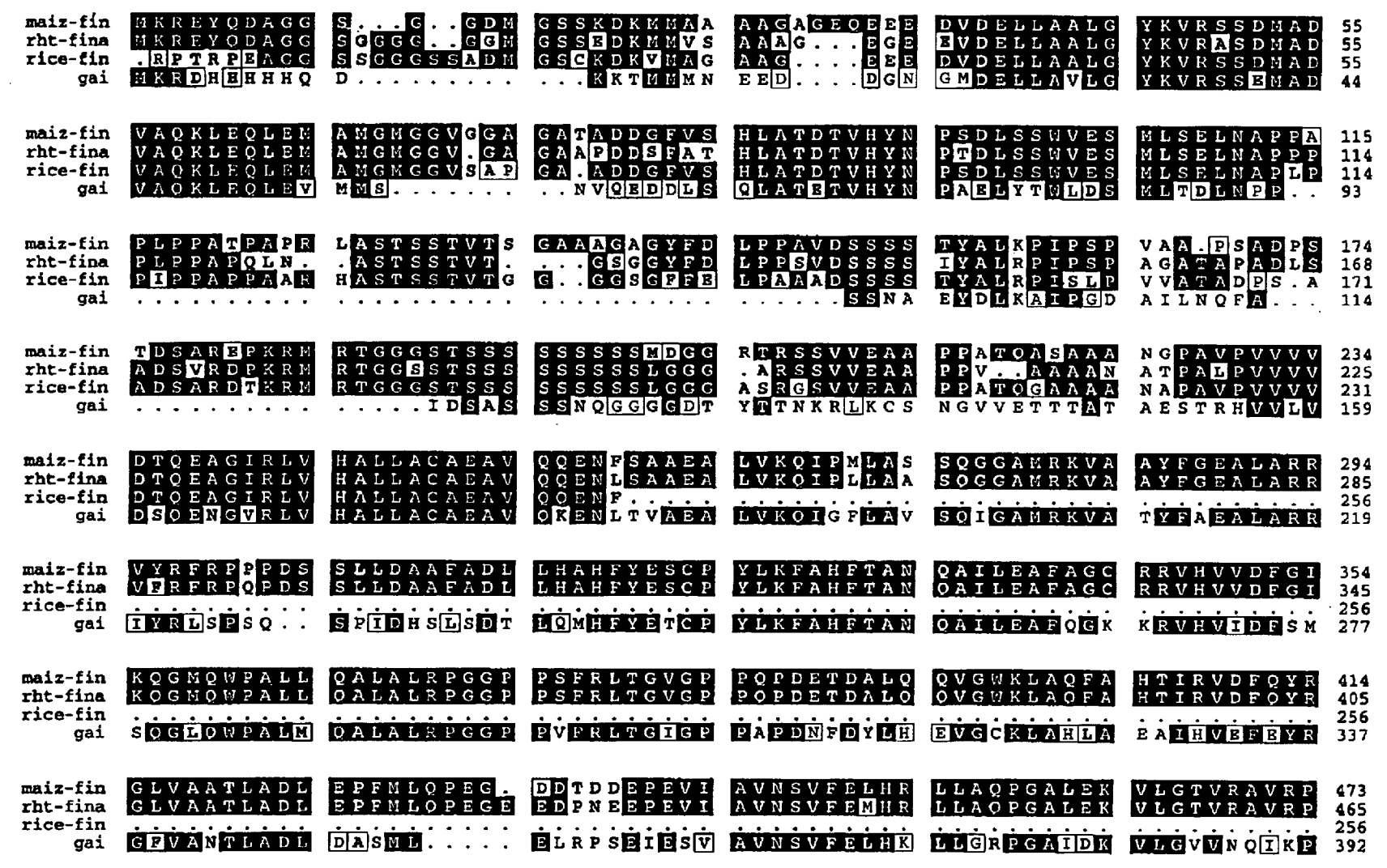
Figure 10B:
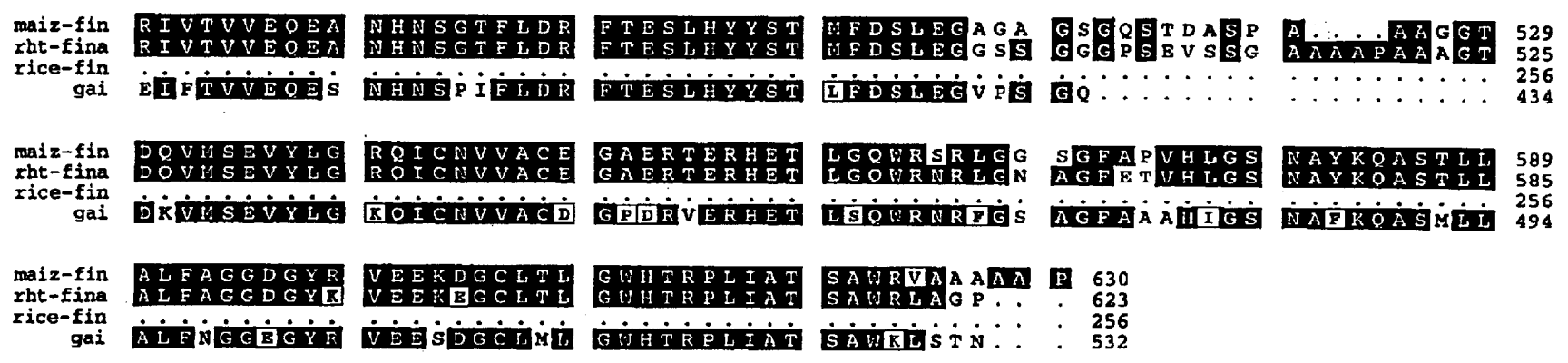

Mutations were found in the candidate D8 and Rht genes in each of the above mutants. The D8-1 mutation is an in-frame deletion which removes amino acids VAQK (SEQ ID NO:101) (55–59) and adds a G (see sequence in FIG. 11a and FIG. 11b). This deletion overlaps with the conserved DVAQKLEQLE homology block described above. D8-2023 is another in-frame deletion mutation that removes amino acids LATDTVHYNPSD (SEQ ID NO:102) (87–98) from the N-terminus of the D8 protein (see FIG. 11c and FIG. 11d). This deletion does not overlap with the deletion in gai or D8-1, but covers another region that is highly conserved between GAI, D8 and Rht (see FIG. 10). Finally, Rht-D1c contains another small in-frame deletion that removes amino acids LNAPPPPLPPAPQ (SEQ ID NO:103) (109–121) in the N-terminal region of the mutant Rht protein that it encodes (see FIG. 12a and FIG. 12b) (LN-P is conserved between GAI, D8 and Rht, see FIG. 10).

Thus all of the above described mutant alleles are dominant, and confer dwarfism associated with reduced GA-response. All three of these alleles contain deletion mutations which remove a portion of the N-terminal half of the protein that they encode. These observations demonstrate that the D8 and Rht genes of maize and wheat have been cloned.

TABLE 1

Primers used in the sequencing of Rht

| Name | Sequence | Sense |
|---|---|---|
| 15-L | TTTGCGCCAATTATTGGCCAGAGATAGA-TAGAGAG | Forward |
| 16-L | GTGGCGGCATGGGTTCGTCCGAGGACAA-GATGATG | Forward |
| 23-L | CATGGAGGCGGTGGAGAACTGGGAACGA-AGAAGGG | Reverse |
| 26-L | CCCGGCCAGGCGCCATGCCGAGGTGGCA-ATCAGGG | Reverse |
| 3-L | GGTATCTGCTTCACCAGCGCCTCCGCGG-CGGAGAG | Reverse |
| 9-L | ATCGGCCGCAGCGCGTAGATGCTGCTGG-AGGAGTC | Reverse |
| RHA-1 | CTGGTGAAGCAGATACCCTTGC | Forward |
| RHA-2 | CTGGTTGGCGGTGAAGTGCG | Reverse |
| RHA-3 | GCAAGGGTATCTGCTTCACCAGC | Reverse |
| RHA-5 | CGCACTTCACCGCCAACCAG | Forward |
| RHA-6 | TTGTGATTTGCCTCCTGTTTCC | Forward |
| RHA-7 | CCGTGCGCCCCCGTGCGGCCCAG | Forward |
| RHA-8 | AGGCTGCCTGACGCTGGGGTTGC | Forward |
| RHT-9 | GATCGGCCGCAGCGCGTAGATGC | Reverse |
| RHT-10 | GATCCCGCACGGAGTCGGCGGACAG | Reverse |
| RHT-12 | TCCGACAGCATGCTCTCGACCCAAG | Reverse |
| RHT-13 | TTCCGTCCGTCTGGICGTGAAGAGG | Forward |
| RHT-14 | AAATCCCGAACCCGCCCCCAGAAC | Forward |
| RHT-15 | GCGCCAATTATTGGCCAGAGATAG | Forward |
| RHT-16 | GGCATGGGTTCGTCCGAGGACAAG | Forward |
| RHT-18 | TTGTCCTCGGACGAACCCATGCCG | Reverse |
| RHT-19 | GATCCAAATCCCGAACCCGCCC | Forward |
| RHT-20 | GTAGATGCTGCTGGAGGAGTCG | Reverse |
| RHT-21 | GTCGTCCATCCACCTCTTCACG | Reverse |
| RHT-22 | GCCAGAGATAGATAGAGAGGCG | Forward |
| RHT-23 | TAGGGCTTAGGAGTTTTACGGG | Reverse |
| RHT-24 | CGGAGTCGGCGGACAGGTCGGC | Reverse |
| RHT-25 | CGGAGAGGTTCTCCTGCTGCACGGC | Reverse |
| RHT-26 | TGTGCAACCCCAGCGTCAGGCAG | Reverse |
| RHT-27 | GCGGCCTCGTCGCCGCCACGCTC | Forward |
| RHT-28 | TGGCGGCGACGAGGCCGCGGTAC | Reverse |
| RHT-29 | AAGAATAAGGAAGAGATGGAGATGGTTG | Reverse |
| RHT-30 | TCTGCAACGTGGTGGCCTGCGAG | Forward |
| RHT-31 | CCCCTCGCAGGCCACCACGTTGC | Reverse |
| RHT-32 | TTGGGTCGAGAGCATGCTGTCGGAG | Forward |

TABLE 2

Primers used in the sequence of D-8 clones (SEQ ID NO:80–SEQ ID NO:100)

| Name | Sequence | Sense |
|---|---|---|
| ZM-8 | GGCGATGACACGGATGACG | Forward |
| ZM-9 | CTTGCGCATGGCACCGCCCTGCGACGAAG | Reverse |
| ZM-10 | CCAAGCTAATAATGGCTTGCGCGCCTCG | Reverse |
| ZM-11 | TATCCAGAACCGAAACCGAG | Forward |
| ZM-12 | CGGCGTCTTGGTACTCGCGCTTCATG | Reverse |
| ZM-13 | TGGGCTCCCGCGCCGAGTCCGTGGAC | Reverse |
| ZM-14 | CTCCAAGCCTCTTGCGCTGACCGAGATCGAG | Forward |
| ZM-15 | TCCACAGGCTCACCAGTCACCAACATCAATC | Forward |
| ZM-16 | ACGGTACTGGAAGTCCACGCGGATGGTGTG | Reverse |
| ZM-17 | CGCACACCATCCGCGTGGACTTCCAGTAC | Forward |
| ZM-18 | CTCGGCCGGCAGATCTGCAACGTGGTG | Forward |
| ZM-19 | TTGTGACGGTGGACGATGTGGACGCG-AGCCTTG | Reverse |
| ZM-20 | GGACGCTGCGACAAACCGTCCATCGATCCAAC | Forward |
| ZM-21 | TCCGAAATCATGAAGCGCGAGTACCAAGAC | Forward |
| ZM-22 | TCGGGTACAAGGTGCGTTCGTCGGATATG | Forward |
| ZM-23 | ATGAAGCGCGAGTACCAAGAC | Forward |
| ZM-24 | GTGTGCCTTGATGCGGTCCAGAAG | Reverse |
| ZM-25 | AACCACCCCTCCCTGATCACGGAG | Reverse |
| ZM-27 | CACTAGGAGCTCCGTGGTCGAAGCTG | Forward |
| ZM-28 | GCTGCGGCAAGAAGCCGGTGCAGCTC | Reverse |
| ZM-29 | AGTACACTTCCGACATGACTTG | Reverse |

What is claimed is:

1. An isolated polynucleotide encoding a polypeptide which comprises the amino acid sequence of a Rht polypeptide obtained from *Triticum aestivum*, said sequence comprising the amino acid sequence

DELLAALGYKVRASDMA (SEQ ID NO:104), and which on expression in a *Triticum aestivum* plant provides inhibition of growth of the plant, which inhibition is antagonised by gibberellin.

2. An isolated polynucleotide according to claim 1 which includes the nucleotide sequence of nucleic acid abtained from *Triticum aestivum* encoding the Rht polypeptide, the nucleotide sequence including

GACGAGCTGCTGGCGGCGCTCGGGTA-CAAGGTGCGCGCCTCCGACATGGCG (SEQ ID NO:105).

3. An isolated polynucleotide encoding a polypeptide which comprises the amino acid sequence shown in FIG. 8b (SEQ ID NO:7).

4. An isolated polynucleotide according to claim 3 which has the coding nucleotide sequence shown in FIG. 8a (SEQ ID NO:14).

5. An isolated polynucleotide encoding a polypeptide which on expression in a plant provides inhibition of growth of the plant, which inhibition is antagonised by gibberellin, wherein said polynucleotide specifically hybridizes to the sequence of FIG. 8A (SEQ ID NO:14) at 65° C. in 0.25M Na$_2$HPO$_4$, pH 7.2, 6.5% SDS, 10% dextran sulphate and a final wash at 60° C. in 0.1×SSC, 0.1% SDS, and;

wherein said polypeptide includes the amino acid sequence shown in FIG. 9b (SEQ ID NO:8) for the maize D8 polypeptide.

6. An isolated polynucleotide according to claim 5 which has the coding nucleotide sequence shown in FIG. 9a (SEQ ID NO:15).

7. An isolated polynucleotide encoding a polypeptide which on expression in a plant provides inhibition of growth of the plant, which inhibition is antagonised by gibberellin, wherein said polynucleotide specifically hybridizes to the sequence of FIG. 8A (SEQ ID NO: 14) at 65° C. in 0.25M Na$_2$HPO$_4$, pH 7.2, 6.5% SDS, 10% dextran sulphate and a final wash at 60° C. in 0.1×SSC, 0.1% SDS, and;

wherein said polypeptide includes the amino acid sequence shown in FIG. 6b (SEQ ID NO: 5).

8. An isolated polynucleotide according to claim 7 which has the coding nucleotide sequence shown in FIG. 6a (SEQ ID NO:12).

9. An isolated polynucleotide encoding a polypeptide which on expression in a plant confers a phenotype on the plant which is gibberellin-unresponsive dwarfism or which on expression in a rht null mutant phenotype plant complements the rht null mutants phenotype, such rht null mutant phenotype being resistant to the dwarfing effect of paclobutrazol, which polynucleotide has the coding nucleotide sequence shown in FIG. 9a (SEQ ID NO: 15) wherein the nucleotides encoding the amino acid sequence DELLAALGYKVRSSDMA (SEQ ID NO: 106) are deleted.

10. An isolated polynucleotide encoding a polypeptide which on expression in a plant confers a phenotype on the plant which is gibberellin-unresponsive dwarfism or which on expression in a rht null mutant phenotype plant complements the rht null mutants phenotype, such rht null mutant phenotype being resistant to the dwarfing effect of paclobutrazol, which polynucleotide has the coding nucleotide sequence shown in FIG. 6a (SEQ ID NO: 12), wherein the nucleotides encoding the amino acid sequence DELLAALGYKVRSSDMA (SEQ ID NO: 106) are deleted.

11. An isolated polynucleotide encoding a polypeptide which comprises the amino acid sequence shown in FIG. 8b (SEQ ID NO:7), with the amino acid sequence DELLAALGYKVRASDMA (SEQ ID NO:104) deleted.

12. An isolated polynucleotide according to claim 11 which has the coding nucleotide sequence shown in FIG. 8a (SEQ ID NO:14), wherein the nucleotides encoding the amino acid sequence DELLAALGYKVRASDMA (SEQ ID NO:104) are deleted.

13. An isolated polynucleotide comprising the isolated polynucleotide according to claim 1 operably linked to a regulatory sequence for expression.

14. An isolated polynucleotide according to claim 13 wherein the regulatory sequence includes an inducible promoter.

15. A nucleic acid vector for transformation of a plant cell and including the polynucleotide according to claim 1.

16. A host cell containing a heterologous polynucleotide or nucleic acid vector each comprising the isolated polynucleotide according to claim 1.

17. A host cell according to claim 16 which is a microbial cell.

18. A host cell according to claim 16 which is a plant cell.

19. A plant cell according to claim 18 having said heterologous polynucleotide in its genome.

20. A plant cell according to claim 19 having more than one said polynucleotide per haploid genome.

21. A plant cell according to claim 18 which is comprised in a plant, a plant part or a plant propagule, or an extract of a plant.

22. A method of producing the host cell according to claim 18, the method including incorporating said heterologous polynucleotide or nucleic acid vector into the cell by means of transformation.

23. The method according to claim 22 which includes recombining the polynucleotide with the cell genome such that it is stably incorporated therein.

24. The method according to claim 22 wherein said host cell is a plant cell and said method further includes regenerating a plant from one or more of said transformed cells.

25. A plant comprising the plant cell according to claim 18.

26. A part or propagule of a plant comprising a plant cell according to claim 18.

27. A method of producing a plant, the method including incorporating a polynucleotide according to claim 1 into a plant cell and regenerating a plant from said plant cell.

28. A method according to claim 27 further including sexually or asexually propagating or growing off-spring or a descendant of the plant regenerated from said plant cell.

29. A method of influencing the growth of a plant, the method including causing or allowing expression from a heterologous polynucleotide comprising the isolated polynucleotide according to claim 1 within cells of the plant, whereby said expression of said heterologous polypeptide influences the growth of said plant.

30. A method of identifying or obtaining a polynucleotide encoding a polypeptide which comprises the amino acid sequence DELLAALGYKVRASDMA (SEQ ID NO:104) and which on expression in a plant provides inhibition of growth of the plant, which inhibition is antagonised by gibberellin, wherein said polynucleotide specifically hybridizes to the sequence of FIG. 8A (SEQ ID NO: 14) at 65° C. in 0.25M $Na_2HPO_4$, pH 7.2, 6.5% SDS, 10% dextran sulphate and a final wash at 60° C. in 0.1×SSC, 0.1% SDS., the method comprising screening candidate nucleic acid by PCR using oligonucleotide primers selected from those shown in Tables 1 (SEQ ID NO: 21–SEQ ID NO:55) and 2 (SEQ ID NO: 80–SEQ ID NO:100).

31. The method according to claim 27 further comprising growing off-spring of or a descendant of the plant regenerated rom said plant cell.

* * * * *